(12) United States Patent
Chen et al.

(10) Patent No.: US 12,049,520 B2
(45) Date of Patent: Jul. 30, 2024

(54) BICYCLIC PEPTIDE LIGANDS SPECIFIC FOR CD137

(71) Applicant: BicycleTx Limited, Cambridge (GB)

(72) Inventors: Liuhong Chen, Cambridge (GB); Rachid Lani, Cambridge (GB); Kevin McDonnell, Lexington, MA (US); Gemma Elizabeth Mudd, Cambridge (GB); Peter Park, Lincoln, MA (US)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 17/648,560

(22) Filed: Jan. 21, 2022

(65) Prior Publication Data

US 2022/0213145 A1   Jul. 7, 2022

Related U.S. Application Data

(62) Division of application No. 16/636,105, filed as application No. PCT/GB2018/052222 on Aug. 3, 2018, now Pat. No. 11,261,214.

(30) Foreign Application Priority Data

Aug. 4, 2017 (GB) .................................... 1712589
Feb. 23, 2018 (GB) .................................... 1802934
Apr. 9, 2018 (GB) .................................... 1805850

(51) Int. Cl.
*A61K 38/00* (2006.01)
*A61K 47/64* (2017.01)
*C07K 7/64* (2006.01)

(52) U.S. Cl.
CPC ................ *C07K 7/64* (2013.01); *A61K 47/64* (2017.08); *A61K 38/00* (2013.01)

(58) Field of Classification Search
CPC ..... G06V 40/12–1324; G06V 40/1335; G06V 40/1365–1376; G06V 40/1347–1376
See application file for complete search history.

(56) References Cited

U.S. PATENT DOCUMENTS

| | | | |
|---|---|---|---|
| 2,642,514 A | 6/1953 | Herkenhoff | |
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,595,756 A * | 1/1997 | Bally | A61K 9/1272 264/4.1 |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,326,144 B1 | 12/2001 | Bawendi et al. | |
| 6,468,808 B1 | 10/2002 | Nie et al. | |
| 6,552,065 B2 | 4/2003 | Remiszewski et al. | |
| 7,151,047 B2 | 12/2006 | Chan et al. | |
| 7,192,785 B2 | 3/2007 | Nie et al. | |
| 7,390,799 B2 | 6/2008 | Bruncko et al. | |
| 8,138,347 B2 | 3/2012 | Adams et al. | |
| 8,680,022 B2 | 3/2014 | Gregory et al. | |
| 8,685,890 B2 | 4/2014 | Winter et al. | |
| 8,778,844 B2 | 7/2014 | Winter et al. | |
| 8,906,682 B2 | 12/2014 | June et al. | |
| 8,986,655 B2 | 3/2015 | Weiss et al. | |
| 9,518,081 B2 | 12/2016 | Winter et al. | |
| 9,644,201 B2 | 5/2017 | Winter et al. | |
| 9,657,288 B2 | 5/2017 | Winter et al. | |
| 9,670,482 B2 | 6/2017 | Winter et al. | |
| 9,670,484 B2 | 6/2017 | Winter et al. | |
| 9,670,521 B2 | 6/2017 | Grabstein et al. | |
| 9,868,767 B2 | 1/2018 | Pei et al. | |
| 9,932,367 B2 | 4/2018 | Stace et al. | |
| 9,994,617 B2 | 6/2018 | Tite et al. | |
| 10,118,947 B2 | 11/2018 | Teufel et al. | |
| 10,294,274 B2 | 5/2019 | Teufel et al. | |
| 10,441,663 B2 | 10/2019 | Bennett et al. | |
| 10,532,106 B2 | 1/2020 | Teufel et al. | |
| 10,624,968 B2 | 4/2020 | Bennett et al. | |
| 10,626,147 B2 | 4/2020 | Pei et al. | |

(Continued)

FOREIGN PATENT DOCUMENTS

| | | |
|---|---|---|
| CN | 101497878 A | 5/2009 |
| CN | 105307686 A | 2/2016 |

(Continued)

OTHER PUBLICATIONS

Zugazagoitia et al., Current Challenges in Cancer Treatment, Clinical Therapies, vol. 38, (2016), pp. 1551-1566 (Year: 2016).*
Sporn et at, "Chemoprevention of Cancer," Carcinogenesis, vol. 21 (2000), 525-530. (Year: 2000).*
Adams et al., "Big Opportunities for Small Molecules in Immuno-oncology," Nature Reviews, 2015, 14:603-622.
Adams, "Molecular control of arterial-venous blood vessel identity," Journal of Anatomy, 2003, 202(1):105-112.
Akanuma et al., "MicroRNA-133a regulates the mRNAs of two invadopodia-related proteins, FSCN1 and MMP14, in esophageal cancer," Br J Cancer. Jan. 7, 2014;110(1), 189-98.
Angelini et al., "Bicyclic peptide inhibitor reveals large contact interface with a protease target." ACS chemical biology 7, No. 5 (2012): 817-821.

(Continued)

*Primary Examiner* — Thomas S Heard
(74) *Attorney, Agent, or Firm* — Dechert LLP; Andrea L. C. Reid; Gang Wang

(57) ABSTRACT

The present invention relates to polypeptides which are covalently bound to molecular scaffolds such that two or more peptide loops are subtended between attachment points to the scaffold. In particular, the invention describes peptides which are high affinity binders of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

24 Claims, 2 Drawing Sheets

Specification includes a Sequence Listing.

(56) References Cited

U.S. PATENT DOCUMENTS

| | | |
|---|---|---|
| 10,792,368 B1 | 10/2020 | Teufel et al. |
| 10,800,813 B2 | 10/2020 | Tite et al. |
| 10,857,196 B2 | 12/2020 | Beswick et al. |
| 10,870,679 B2 | 12/2020 | Teufel et al. |
| 10,875,894 B2 | 12/2020 | Chen et al. |
| 10,894,808 B2 | 1/2021 | Teufel et al. |
| 10,899,798 B2 | 1/2021 | Bennett et al. |
| 10,919,937 B2 | 2/2021 | Beswick et al. |
| 10,994,019 B2 | 5/2021 | Teufel et al. |
| 11,103,591 B2 | 8/2021 | Teufel et al. |
| 11,180,531 B2 | 11/2021 | Beswick et al. |
| 11,484,602 B2 | 1/2022 | Chen et al. |
| 11,241,473 B2 | 2/2022 | Beswick et al. |
| 11,261,214 B2 | 3/2022 | Chen et al. |
| 11,306,123 B2 | 4/2022 | Mudd et al. |
| 11,312,749 B2 | 4/2022 | Mudd et al. |
| 11,332,500 B2 | 5/2022 | Mudd et al. |
| 11,396,530 B2 | 7/2022 | Beswick et al. |
| 11,414,488 B2 | 8/2022 | Bennett et al. |
| 11,433,137 B2 | 9/2022 | Bennett et al. |
| 11,453,702 B2 | 9/2022 | Beswick et al. |
| 11,453,703 B2 | 9/2022 | Keen et al. |
| 11,542,304 B2 | 3/2023 | Chen et al. |
| 11,613,560 B2 | 3/2023 | Stephen et al. |
| 11,746,126 B2 | 5/2023 | Bennett et al. |
| 11,672,868 B2 | 6/2023 | Teufel et al. |
| 11,730,819 B2 | 8/2023 | Teufel et al. |
| 11,623,012 B2 | 11/2023 | Chen et al. |
| 11,696,956 B2 | 11/2023 | Chen et al. |
| 2002/0164788 A1 | 11/2002 | Ellis et al. |
| 2005/0169931 A1 | 8/2005 | Kinch et al. |
| 2009/0222937 A1 | 3/2009 | Arnould et al. |
| 2009/0304721 A1 | 10/2009 | Kinch et al. |
| 2012/0101253 A1 | 4/2012 | Heinis et al. |
| 2012/0172235 A1 | 5/2012 | Winter et al. |
| 2013/0064791 A1 | 3/2013 | Poelstra et al. |
| 2013/0072598 A1 | 3/2013 | Yang et al. |
| 2014/0249292 A1 | 9/2014 | Tite et al. |
| 2014/0274759 A1 | 9/2014 | Walker et al. |
| 2014/0256596 A1 | 11/2014 | Tite et al. |
| 2014/0163201 A1 | 12/2014 | Winter et al. |
| 2015/0087810 A1 | 3/2015 | Moore et al. |
| 2015/0038434 A1 | 5/2015 | Yang et al. |
| 2016/0046721 A1 | 2/2016 | Qian et al. |
| 2016/0031939 A1 | 4/2016 | Stace et al. |
| 2016/0122430 A1 | 5/2016 | Gish et al. |
| 2016/0256579 A1 | 8/2016 | Shalom |
| 2016/0326232 A1 | 10/2016 | Rosa et al. |
| 2017/0067045 A1 | 3/2017 | Winter et al. |
| 2017/0190743 A1 | 7/2017 | Pei et al. |
| 2017/0204150 A1 | 7/2017 | Liu et al. |
| 2017/0306032 A1 | 10/2017 | Gehlsen |
| 2017/0360952 A1 | 12/2017 | Schwartz et al. |
| 2018/0280525 A1 | 4/2018 | Teufel et al. |
| 2018/0169254 A1 | 6/2018 | Bennett et al. |
| 2018/0200378 A1 | 7/2018 | Bennett et al. |
| 2018/0318451 A1 | 8/2018 | Skerra et al. |
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0134213 A1 | 5/2019 | Teufel et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2019/0389907 A1 | 12/2019 | Teufel et al. |
| 2020/0129630 A1 | 4/2020 | Koehler et al. |
| 2020/0131228 A1 | 4/2020 | Beswick et al. |
| 2020/0171161 A1 | 4/2020 | Teufel et al. |
| 2020/0190213 A1 | 6/2020 | Preyer et al. |
| 2020/0215199 A1 | 7/2020 | Bennett et al. |
| 2020/0255477 A1 | 8/2020 | Chen et al. |
| 2020/0289657 A1 | 9/2020 | Teufel et al. |
| 2020/0291096 A1 | 9/2020 | Keen et al. |
| 2020/0283482 A1 | 10/2020 | Keen et al. |
| 2020/0316209 A1 | 10/2020 | Teufel et al. |
| 2020/0338203 A1 | 10/2020 | Chen et al. |
| 2020/0354406 A1 | 11/2020 | Stephen et al. |
| 2020/0354456 A1 | 11/2020 | Bennett et al. |
| 2020/0407709 A1 | 12/2020 | Chen et al. |
| 2021/0040154 A1 | 2/2021 | Mudd et al. |
| 2021/0046145 A1 | 2/2021 | Beswick et al. |
| 2021/0069287 A1 | 3/2021 | Mudd et al. |
| 2021/0079045 A1 | 3/2021 | Bennett et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0122785 A1 | 4/2021 | Teufel et al. |
| 2021/0122804 A1 | 4/2021 | Teufel et al. |
| 2021/0147484 A1 | 5/2021 | Beswick et al. |
| 2021/0147485 A1 | 5/2021 | Teufel et al. |
| 2021/0261620 A1 | 8/2021 | Teufel et al. |
| 2021/0269480 A1 | 9/2021 | Beswick et al. |
| 2021/0299210 A2 | 9/2021 | Keen et al. |
| 2022/0023432 A1 | 1/2022 | Teufel et al. |
| 2022/0024982 A1 | 1/2022 | Chen et al. |
| 2022/0054646 A1 | 2/2022 | Chen et al. |
| 2022/0031858 A1 | 3/2022 | Mcdonnell et al. |
| 2022/0064218 A1 | 3/2022 | Baldassarre et al. |
| 2022/0064221 A1 | 3/2022 | Lani et al. |
| 2022/0088118 A1 | 3/2022 | Baldassarre et al. |
| 2022/0088207 A1 | 3/2022 | Chen et al. |
| 2022/0089643 A1 | 3/2022 | Beswick et al. |
| 2022/0119488 A1 | 4/2022 | Lani et al. |
| 2022/0133732 A1 | 5/2022 | Baldassarre et al. |
| 2022/0133733 A1 | 5/2022 | Baldassarre et al. |
| 2022/0135614 A1 | 5/2022 | Teufel et al. |
| 2022/0184222 A1 | 6/2022 | Bennett et al. |
| 2022/0194983 A1 | 6/2022 | Teufel et al. |
| 2022/0227811 A1 | 7/2022 | Mudd et al. |
| 2022/0242911 A1 | 8/2022 | Mudd et al. |
| 2022/0257784 A1 | 8/2022 | Upadhyaya et al. |
| 2022/0281918 A1 | 8/2022 | Van Rietschoten et al. |
| 2022/0387611 A1 | 8/2022 | Bennett et al. |
| 2022/0275053 A1 | 9/2022 | Upadhyaya et al. |
| 2022/0289792 A1 | 9/2022 | Chen et al. |
| 2022/0306694 A1 | 9/2022 | Mudd et al. |
| 2022/0072140 A1 | 10/2022 | Stace et al. |
| 2022/0362390 A1 | 11/2022 | Stace et al. |
| 2023/0002596 A1 | 1/2023 | Zhang et al. |
| 2023/0008076 A1 | 1/2023 | Keen et al. |
| 2023/0025916 A1 | 1/2023 | Bennett et al. |
| 2023/0025971 A1 | 1/2023 | Bennett et al. |
| 2023/0165966 A1 | 1/2023 | Koehler et al. |
| 2023/0086865 A1 | 3/2023 | Balmford et al. |
| 2023/0106511 A1 | 4/2023 | Balmford et al. |
| 2023/0129258 A1 | 4/2023 | Upadhyaya et al. |
| 2023/0181749 A1 | 6/2023 | Dickson et al. |
| 2023/0220008 A1 | 7/2023 | Chen et al. |
| 2023/0233698 A1 | 7/2023 | Bennett et al. |
| 2023/0287047 A1 | 9/2023 | Beswick et al. |
| 2023/0340020 A1 | 10/2023 | Teufel et al. |
| 2023/0144799 A1 | 11/2023 | Chen et al. |

FOREIGN PATENT DOCUMENTS

| | | |
|---|---|---|
| EP | 2393520 A1 | 12/2011 |
| EP | 2970954 A1 | 1/2016 |
| EP | 3192802 A1 | 7/2017 |
| FR | 2932189 A1 | 11/2009 |
| GB | 1239978 A | 7/1971 |
| JP | 2006514104 A | 4/2006 |
| JP | 2011513298 A | 4/2011 |
| JP | 2011522794 A | 4/2011 |
| WO | WO9708320 A1 | 6/1997 |
| WO | WO9819705 A1 | 5/1998 |
| WO | WO0128683 A1 | 4/2001 |
| WO | WO0142246 A2 | 6/2001 |
| WO | WO0363794 A2 | 8/2003 |
| WO | WO2004005348 A1 | 1/2004 |
| WO | WO2004019973 A1 | 3/2004 |
| WO | WO0288112 A1 | 8/2004 |
| WO | WO-2004077062 A2 | 9/2004 |
| WO | WO2004089925 A1 | 10/2004 |

(56) References Cited

FOREIGN PATENT DOCUMENTS

| | | |
|---|---|---|
| WO | WO2004106328 A1 | 12/2004 |
| WO | WO2005007623 A2 | 1/2005 |
| WO | WO2005103083 A2 | 11/2005 |
| WO | WO2005113554 A2 | 12/2005 |
| WO | WO2006029879 A2 | 3/2006 |
| WO | WO2006078161 A1 | 7/2006 |
| WO | WO2006078846 A1 | 7/2006 |
| WO | WO2006105021 A2 | 10/2006 |
| WO | WO2006122806 A2 | 11/2006 |
| WO | WO2007016176 A2 | 2/2007 |
| WO | WO2007044729 A2 | 4/2007 |
| WO | WO2007053452 A1 | 5/2007 |
| WO | WO2007070514 A1 | 6/2007 |
| WO | WO2007005874 A2 | 7/2007 |
| WO | WO2007084786 A1 | 7/2007 |
| WO | WO2007129161 A2 | 11/2007 |
| WO | WO2008033561 A2 | 3/2008 |
| WO | WO2008039218 A2 | 4/2008 |
| WO | WO2008134761 A2 | 6/2008 |
| WO | WO2008089627 A1 | 7/2008 |
| WO | WO2008109943 A1 | 9/2008 |
| WO | WO2008118802 A1 | 10/2008 |
| WO | WO2008132601 A1 | 11/2008 |
| WO | WO2008157490 A1 | 12/2008 |
| WO | WO2009009116 A2 | 1/2009 |
| WO | WO2009044273 A2 | 4/2009 |
| WO | WO2009073620 A2 | 6/2009 |
| WO | WO2009098450 A2 | 8/2009 |
| WO | WO2009114512 A1 | 9/2009 |
| WO | WO2010019570 A2 | 2/2010 |
| WO | WO2010077634 A1 | 7/2010 |
| WO | WO2010089115 A1 | 8/2010 |
| WO | WO2010089117 A1 | 12/2010 |
| WO | WO2011018227 A2 | 2/2011 |
| WO | WO2011028683 A1 | 3/2011 |
| WO | WO2011056652 A1 | 5/2011 |
| WO | WO2011070024 A1 | 6/2011 |
| WO | WO2011079015 A1 | 6/2011 |
| WO | WO2011090760 A1 | 7/2011 |
| WO | WO2011107553 A1 | 9/2011 |
| WO | WO2011109400 A2 | 9/2011 |
| WO | WO2011131407 A1 | 10/2011 |
| WO | WO2011140249 A2 | 11/2011 |
| WO | WO2012032433 A1 | 3/2012 |
| WO | WO-2012/057624 A1 | 5/2012 |
| WO | WO2012142237 A1 | 10/2012 |
| WO | WO2012145493 A1 | 10/2012 |
| WO | WO2013050615 A1 | 4/2013 |
| WO | WO2013050617 A1 | 4/2013 |
| WO | WO2013079174 A1 | 6/2013 |
| WO | WO2013087699 A1 | 6/2013 |
| WO | WO2013119716 A1 | 8/2013 |
| WO | WO2013132044 A1 | 9/2013 |
| WO | WO2013050616 A1 | 11/2013 |
| WO | WO2013169264 A1 | 11/2013 |
| WO | WO2014008218 A1 | 1/2014 |
| WO | WO2014036357 A1 | 3/2014 |
| WO | WO2014044872 A1 | 3/2014 |
| WO | WO2014063012 A1 | 4/2014 |
| WO | WO2014142237 A1 | 9/2014 |
| WO | WO2014164693 A2 | 10/2014 |
| WO | WO2014167122 A1 | 10/2014 |
| WO | WO2014190257 A2 | 11/2014 |
| WO | WO2015116904 A1 | 6/2015 |
| WO | WO2015171938 A1 | 11/2015 |
| WO | WO2015179691 A2 | 11/2015 |
| WO | WO2016046574 A1 | 3/2016 |
| WO | WO2016067035 A1 | 5/2016 |
| WO | WO2016050361 A1 | 7/2016 |
| WO | WO2016171242 A1 | 10/2016 |
| WO | WO2016171272 A1 | 10/2016 |
| WO | WO2016174103 A1 | 11/2016 |
| WO | WO2017161069 A1 | 9/2017 |
| WO | WO2017173408 A1 | 10/2017 |
| WO | WO2017182672 A1 | 10/2017 |
| WO | WO-2017/191460 A1 | 11/2017 |
| WO | WO2018096365 A1 | 5/2018 |
| WO | WO2018115203 A1 | 6/2018 |
| WO | WO2018115204 A1 | 6/2018 |
| WO | WO2018222987 A1 | 6/2018 |
| WO | WO2018127699 A1 | 7/2018 |
| WO | WO2018156740 A1 | 8/2018 |
| WO | WO2018197509 A1 | 11/2018 |
| WO | WO2018197893 A1 | 11/2018 |
| WO | WO2019002842 A1 | 1/2019 |
| WO | WO-2019/025811 A1 | 2/2019 |
| WO | WO2019034866 A1 | 2/2019 |
| WO | WO2019034868 A1 | 2/2019 |
| WO | WO2019084060 A1 | 2/2019 |
| WO | WO2019094395 A2 | 5/2019 |
| WO | WO2019122860 A1 | 6/2019 |
| WO | WO2019122861 A1 | 6/2019 |
| WO | WO2019122863 A1 | 6/2019 |
| WO | WO-2019/162682 A1 | 8/2019 |
| WO | WO-2019/193328 A1 | 10/2019 |
| WO | WO2019136442 A1 | 11/2019 |
| WO | WO2019226617 A1 | 11/2019 |
| WO | WO2019243313 A1 | 12/2019 |
| WO | WO2019243329 A1 | 12/2019 |
| WO | WO2019243353 A1 | 12/2019 |
| WO | WO2019243455 A1 | 12/2019 |
| WO | WO2019243832 A1 | 12/2019 |
| WO | WO2019243833 A1 | 12/2019 |
| WO | WO2020084305 A1 | 4/2020 |
| WO | WO2020089627 A1 | 5/2020 |
| WO | WO2020120980 A1 | 6/2020 |
| WO | WO2020120981 A1 | 6/2020 |
| WO | WO2020120983 A1 | 6/2020 |
| WO | WO2020120984 A1 | 6/2020 |
| WO | WO2020128526 A1 | 6/2020 |
| WO | WO2020128527 A1 | 6/2020 |
| WO | WO2020148525 A1 | 7/2020 |
| WO | WO2020148526 A1 | 7/2020 |
| WO | WO2020148527 A1 | 7/2020 |
| WO | WO2020148528 A1 | 7/2020 |
| WO | WO2020148529 A1 | 7/2020 |
| WO | WO2020148530 A1 | 7/2020 |
| WO | WO2020165600 A1 | 8/2020 |
| WO | WO2020178574 A1 | 9/2020 |
| WO | WO2020201753 A1 | 10/2020 |
| WO | WO2020225577 A1 | 11/2020 |
| WO | WO2020229803 A1 | 11/2020 |
| WO | WO-2021/019243 A1 | 2/2021 |
| WO | WO2021019244 A1 | 2/2021 |
| WO | WO2021019245 A1 | 2/2021 |
| WO | WO2021019246 A1 | 2/2021 |
| WO | WO2021028686 A1 | 2/2021 |
| WO | WO2021171028 A1 | 2/2021 |
| WO | WO2021171029 A1 | 2/2021 |
| WO | WO-2021/064428 A1 | 4/2021 |
| WO | WO2021038232 A1 | 4/2021 |
| WO | WO2021074622 A1 | 4/2021 |
| WO | WO2021074647 A1 | 4/2021 |
| WO | WO2021105694 A1 | 6/2021 |
| WO | WO2021148974 A1 | 7/2021 |
| WO | WO2021234391 A1 | 11/2021 |
| WO | WO2021250418 A1 | 12/2021 |
| WO | WO2022038158 A1 | 2/2022 |
| WO | WO2022148969 A1 | 7/2022 |
| WO | WO2022148974 A2 | 7/2022 |
| WO | WO2022148975 A1 | 7/2022 |
| WO | WO2022148979 A1 | 7/2022 |
| WO | WO2022029420 A1 | 10/2022 |
| WO | WO2023089308 A1 | 5/2023 |
| WO | WO2023031623 A2 | 9/2023 |

OTHER PUBLICATIONS

Annunziata et al., "Phase 1, open-label study of MED1-547 in patients with relapsed or refractorysolid tumors," Invest New Druas, Feb. 2013, 31(1):77-84.

(56) References Cited

OTHER PUBLICATIONS

Anonymous, "Bicycle Conjugates", URL: https://web.archive.org/web/20210104063050/https://www.bicycletherapeutics.com/programs, 2021, 4 pages.

Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL: https://www.businesswire.com/news/home/20200515005111/en/Bicycle-Therapeutics-to-Present-New-Translational-Research-for-BT5528-and-Preelinical-Data-for-Tumor-targeted-Immune-Cell-Aaonists-at-the-AACR-Virtual-Annual-Meeting-II.

Anonymous, "Constrained Peptides Unconstrained Thinking Forward-Looking Statements", URL: https://investors.bicycletherapeutics.com/static-files/5f7f462f-2417-439d-b829-d723b3fd65f7, Aug. 2019, 26 pages.

Anthony et al., "Recapitulation of IVIG anti-inflammatory activity with a recombinant IgG Fc", Science Apr. 18, 2008;320(5874):373-376.

Arkadash et al., "Development of High Affinity and High Specificity Inhibitors of Matrix Metalloproteinase 14 through Computational Design and Directed Evolution" J. Biol. Chem. 2017, 292(8), 3481-3495.

Arnon et al., "The mechanisms controlling the recognition of tumor- and virus-infected cells by NKp46", Blood, Jan. 15, 2004;103(2):664-672.

Arnould et al., "Trastuzumab-based treatment of HER2-positive breast cancer: an antibody-dependent cellular cytotoxicity mechanism?", Br J Cancer, 2006, 94(2):259-267.

Askoxylakis et al., "A New Peptide Ligand for Targeting Human Carbonic Anhydrase IX, Identified through the Phage Display Technology", Plos ONE, Dec. 2010, 5(12):10 pages.

Augoff et al., "Upregulated expression and activation of membrane-associated proteases in esophageal squamous cell carcinoma." Oncology reports, 2014, 31(6):2820-2826.

Ausiello et al., "Functional topography of discrete domains of human CD38," Tissue Antigens, Dec. 2000, 56(6):539-547.

Baek et al. "Effects of Histidine and Sucrose on the Biophysical Properties of a Monoclonal Antibody," Pharmaceutical Antibody, 2017, 34(3):629-639.

Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).

Banerji et al., "Preliminary pharmacokinetic assessment of BT1718: A phase I/IIa trial of BT1718 (a first in class Bicycle Toxin Conjugate) in patients with advanced solid tumours." In european journal of cancer, 2018, 103:E65-e65.

Barbas III et al., "Semisynthetic combinatorial antibody libraries: a chemical solution to the diversity problem," Proceedings of the National Academy of Sciences of the United States of America, May 1992, 89(10):4457-4461.

Barbolina et al., Microenvironmental regulation of membrane type 1 matrix metalloproteinase activity in ovarian carcinoma cells via collagen-induced EGR1 expression. Journal of Biological Chemistry, 2007, 282(7):4924-4931.

Bardia et al., "Efficacy and safety of anti-trop-2 antibody drug conjugate sacituzumab govitecan (IMMU-132) in heavily pre-treated patients with metastatic triple-negative breast cancer." Journal of Clinical Oncology, 2017, 35(19):2141.

Bech et al., "Chemical Strategies for Half-Life Extension of Biopharmaceuticals: Lipidation and Its Alternatives," ACS Medicinal Chemistry Letters, Jun. 2018, 9(7):577-580.

Bennett et al., "Abstract 4481: BT5528, an EphA2-targeting Bicycle Toxin Conjugate (BTC): Profound efficacy without bleeding and coagulation abnormalities in animal models", Cancer Research, 2019, 79(13 suppl):4481. 2 pages.

Bennett et al., "Abstract 5854: BT5528, a Bicycle Toxin Conjugate targeting EphA2 has potent anti-tumor activity without bleeding or coagulation abnormalities in preclinical models." Cancer Res., 2018, 78(13 suppl):5854.

Bennett et al., "Abstract 5855: Bicycle Drug Conjugates Targeting EphA2 for the Treatment of Solid Tumors: Discovery and Selection of BT5528", Cancer Research, 2018, 78(13 suppl):5855. 2 pages.

Bennett et al., "Development of BT1718, a Bicycle Drug Conjugate® (BDC) targeting MT1-MMP for treatment of solid tumours," European Journal of Cancer, Nov. 2016, 69(1):S21.

Bennett et al., "MMAE Delivery Using the Bicycle Toxin Conjugate BT5528," Mol Cancer Ther., Jul. 2020, 19(7):1385-1394.

Bennett et al., "The Mechanism of Action of BT1718, a Novel Small-Molecule Drug Conjugate for the Treatment of Solid Tumors Expressing MT1-MMP," AACR-NCI-EOrTC International Conference: Molecular Taroets and Cancer Therapeutics, Jan. 26-30, 2018.

Bennett, "BT1718, a Bicycle Drug Conjugate (BTC): Profound Efficacy Without Bleeding and Coagulation Abnormalities in Animal Models," AACR Annual Meeting 2019, 4481, 2 pages.

Ben-Shmuel et al., "Unleashing Natural Killer Cells in the Tumor Microenvironment—The Next Generation of Immunotherapy?", Front Immunol., 2020, 11:275.

Berenson, "Multiple Myeloma," Merck Manual, Retrieved from: https://www.merckmanuals.com/home/blood-disorders/plasma-cell-disorders/multiplemyeloma?query=multiple%20myeloma, Oct. 2022.

Berge et al., "Pharmaceutical Salts," Journal of Pharmaceutical Sciences, Jan. 1977, 66(1):1-19.

Berkel et al. "Binding of (5 S)-penicilloic acid to penicillin binding protein 3." ACS chemical biology 8, No. 10 (2013): 2112-2116.

Bernhagen et al., "Design, synthesis and characterization of different bicyclic peptides with enhanced binding and selectivity for various integrins", Retrieved form: https://ec.europa.eu/research/participants/documents/downloadPublic?documentIds=080166e5acfd6757&appId=PPGMS, Oct. 14, 2016, XP55622035:1-6.

Beswick, Paul, "Bicycles—An entirely new class of therapeutics," accessed on https://www.bicycletherapeutics.com/wp-content/uploads/RSC-02-May 2019.pdf, 2019, 21 pages.

Bicycle Therapeutics, "Bicycle Therapeutics and Cancer Research UK Announce Initiation of First Clinical Study of a Bicyclic Peptide (Bicycle®)," Press Release, Feb. 13, 2018, https://investors.bicycletherapeutics.com/node/6651/pdf.

Bicycle Therapeutics, "Bicycle Therapeutics to Present New BT1718 Data in the "New Drugs on the Horizon" Session at the 2018 American Association for Cancer Research Meeting," Press Release. Apr. 3, 2018.

Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.

BicycleTx Limited, "Study BT5528-100 in Patients with Advanced Solid Tumors Associated with EphA2 Expression," ClinicalTrials.gov Identifier NCT04180371. First Posted Nov. 27, 2019; Accessed Dec. 3, 20220: https://clinicaltrials.gov/ct2/show/NCT04180371.

Bilsky, Mark H., "Gliomas", Merck Manual (https://www.merckmanuals.com/professional/neurologic-disorders/intracranial-and-spinal-tumors/gliomas), May 2023, 8 pages.

Binda et al., "The EphA2 receptor drives self-renewal and tumorigenicity in stem-like tumor-propagating cells from human glioblastomas," Cancer Cell, Dec. 11, 2012, 22(6):765-780.

Biron et al., "Improving oral bioavailability of peptides by multiple N-methylation: somatostatin analogues," Angewandte Chemie International Edition, 2008, 47(14):2595-2599.

Blank et al., "Absence of Programmed Death Receptor 1 Alters Thymic Development and Enhances Generation of CD4/CD8 Double-Negative TCR-Transgenic T Cells" in Journal of Immunology, Nov. 2003, 171(19):4574-4581.

Bogaerts et al., "Individual patient data analysis to assess modifications to the RECIST criteria." European journal of cancer, 2009, 45(2):248-260.

Bolland et al., "Spontaneous autoimmune disease in Fc(gamma)RIIB-deficient mice results from strain-specific epistasis", Immunity, Aug. 2000, 13(2):277-285.

(56) References Cited

OTHER PUBLICATIONS

Booth et al., "Crowd control in the crypt," Nat Med., Dec. 2002, 8(12):1360-1361.
Borghaei et al., "Nivolumab versus docetaxel in advanced non squamous non-small-cell lung cancer." New England Journal of Medicine, 2015, 373(17):1627-1639.
Borrelli et al., "Cell Penetrating Peptides as Molecular Carriers for Anti-Cancer Agents," Molecules, Feb. 2018, 23(2):295. (28 pages).
Boruchov et al., "Activating and inhibitory IgG Fc receptors on human DCs mediate opposing functions", The Journal of Clinical Investigation, 2005, 115(10):2914-2923.
Bouchard et al., "Antibody-drug conjugates—a new wave of cancer drugs." Bioorganic & medicinal chemistry letters, 2014, 24(23):5357-5363.
Brahmer et al., "Nivolumab versus docetaxel in advanced squamous-cell non-small-cell lung cancer." New England Journal of Medicine, 2015, 373(2):123-135.
Brannan et al., "EphA2 in the early pathogenesis and progression of non-small cell lung cancer," Cancer Prev Res (Phila)., Dec. 2009, 2(12):1039-1049.
Brantley-Sieders et al., "Eph receptor tyrosine kinases in tumor and tumor microenvironment", Current Pharmaceutical Design, 2004, 10(27):3431-3442.
Brantley-Sieders et al., "Eph/Ephrin Profiling in Human Breast Cancer Reveals Significant Associations between Expression Level and Clinical Outcome", Plos One, 2011, 6(9):e24426.
Brantley-Sieders et al., "Impaired tumor microenvironment in EphA2-deficient mice inhibits tumor angiogenesis and metastatic progression," FASEB J., Nov. 2005, 19(13):1884-1886.
Bristol-Myers Squibb, "An Investigational Immuno-Therapy Study to Investigate the Safety and Effectiveness of Nivolumab, and Nivolumab Combination Therapy in Virus-Associated Tumors-Full Text View-Clinicaltrials." Gov. [(accessed on Jan. 30, 2021)] (2018).
Brown et al., "Blockade of programmed death-1 ligands on dendritic cells enhances T cell activation and cytokine production", Journal of Immunology, Feb. 2003, 170(3):1257-1266.
Cabanillas et al., "Phase I study of maytansine using a 3-day schedule," Cancer Treat Rep., Mar. 1978, 62(3):425-428.
Cancer Research UK, "Soft tissue sarcomas," Retrieved from: http://aboutcancer.cancerresearchuk.org/about-cancer/soft-tissue-sarcoma, Sep. 2022.
Cancer Research UK, "Triple Negative Breast Cancer," Retrieved from: https://www.cancerresearchuk.org/about-cancer/breast-cancer/stages-types-grades/types/triplenegative-breast-cancer#, Sep. 2022, 6 pages.
Cancer Research UK, "Types of lung cancer," Retrieved form: https://www.cancerresearchuk.org/about-cancer/lung-cancer/stages-types-grades/types#, Sep. 2022.
Cancer Research UK, "Your mouth and cancer drugs," Retrieved form: https://www.cancerresearchuk.org/about-cancer/cancer-in-general/treatment/cancer-drugs/sideeffects/your-mouth, Sep. 2022, 5 pages.
Caratelli et al., "FCγ Chimeric Receptor-Engineered T Cells: Methodology, Advantages, Limitations, and Clinical Relevance", Frontiers in Immunology, Apr. 27, 2017, :8:457, 8 pages.
Center for Pancreatic and Biliary Diseases, "Bile Duct Cancer," University of Southern California, Department of Surgery. Retrieved from https://web.archive.org/web/20171207023733/http://www.surgery.usc.edu:80/divisions/tumor/PancreasDiseases/web%20pages/BILIARY%20SYSTEM/cholangiocarcinoma.html.
Centers for Disease Control and Prevention, "What Can I Do to Reduce My Risk of Ovarian Cancer?", Division of Cancer Prevention and Control, Aug. 31, 2022, 1 page.
Chabner et al., "Initial clinical trials of maytansine, an antitumor plant alkaloid." Cancer Treat Rep., 1978, 62(3):429-433.
Chahinian et al., "Phase I study of weekly maytansine given by iv bolus or 24-hour infusion," Cancer Treat Rep., Nov. 1979, 63(11-12),1953-1960.

Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.
Chan and Nie, "Quantum dot bioconjugates for ultrasensitive nonisotopic detection," Science, Sep. 25, 1998; 281(5385):2016-2018.
Chandrasekar, "Bladder Cancer," Merck Manual; Retrieved form: https://www.merckmanuals.com/professional/genitourinary-disorders/genitourinary-cancers/bladder-cancer, Sep. 2022.
Chandrasekar, "Prostate Cancer," Merck Manual. Retrieved from: https://www.merckmanuals.com/professional/genitourinary-disorders/genitourinary-cancers/prostate-cancer, Sep. 2022.
Chang et al., "Five different anti-prostate-specific membrane antigen (PSMA) antibodies confirm PSMA expression in tumor-associated neo vasculature," Cancer Res., Jul. 1, 1999, 59(13):3192-3198.
Chang et al., "Subtiligase: A Tool for Semisynthesis of Proteins", Proc Natl Acad Sci, 1994, 91(26):12544-12548.
Chemnitz et al., "RNA fingerprints provide direct evidence for the inhibitory role of TGFß and PD-1 on CD4+ T cells in Hodgkin lymphoma", Blood, 2007, 110(9):3226-3233.
Chen and Harrison, "Cell-Penetrating Peptides in Drug Development: Enabling Intracellular Targets," Biochemical Society Transactions, 2007, 35(4):821-825.
Chen et al., "Association of FCGR3A and FCGR3B copy number variations with systemic lupus erythematosus and rheumatoid arthritis in Taiwanese patients", Arthritis & Rheumatology, 2014, 66(11):3113-3121.
Chen et al., "Structurally diverse cyclisation linkers impose different backbone conformations in bicyclic peptides," Chembiochem., May 7, 2012, 13(7):1032-1038.
Chen et al., "The Bicycle Platform: an Efficient Technology to Generate High Affinity, High Selectivity Molecules (Bicycles®) with Unique Drug Like Properties that are Amenable to Conjugation," URL: https://www.bicycletherapeutics.com/wp-content/uploads/16_PEGS-Bicycle-30-04-2017-poster.pdf, Apr. 26, 2017, 1 page.
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.
Cheng et al., "Blockade of EphA receptor tyrosine kinase activation inhibits vascular endothelial cell growth factor-induced angiogenesis," Mol Cancer Res., Nov. 2002, 1(1):2-11.
Cherney et al., "Macrocyclic Amino Carboxylates as Selective MMP-8 Inhibitors," Journal of Medicinal Chemistry, May 1998, 41(11):1749-1751.
Chiche et al., "Hypoxia-inducible carbonic anhydrase IX and XII promote tumor cell growth by counteracting acidosis through the regulation of the intracellular pH," Cancer Res., Jan. 1, 2009, 69(1):358-368.
Chinnery et al., "Viral antigen mediated NKp46 activation of NK cells results in tumor rejection via NK-DC crosstalk", Oncoimmunology, 2012, 1(6):874-883.
Christina Chun, "What are the most curable cancers?", Medical news Today (https://www.medicalnewstoday.com/articles/322700 Accessed May 8, 2020), 2020, 8 pages.
Chung et al., "Bicycle synthesis through peptide macrocyclization using aziridine aldehydes followed by late stage disulfide bond installation." MedChemComm, 2023, 4(7):1124-1128.
Clarkson et al., "Treatment of refractory immune thrombocytopeniaurpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
Clynes et al., "Inhibitory Fc receptors modulate in vivo cytotoxicity against tumor targets", Nature Medicine, Apr. 2000, 6(4):443-446.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013; EMA/749228/2013.

(56) References Cited

OTHER PUBLICATIONS

Connolly et al., "Complexities of TGF-ß Targeted Cancer Therapy", Int'l J. Biological Sciences, 2012, 8(7):964-978.

Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30, Jan. 2019, Page v174.

Cortes et al., "Phase II study of the halichondrin B analog eribulin mesylate in patients with locally advanced or metastatic breast cancer previously treated with an anthracycline, a taxane, and capecitabine." Journal of Clinical Oncology, 2010, 28(25):3922-3928.

Costello et al., "Defective expression and function of natural killer cell-triggering receptors in patients with acute myeloid leukemia", Blood, 2002, 99(10):3661-3667.

Crameri et al., "Construction and evolution of antibody-phage libraries by DNA shuffling," Nature Medicine, Jan. 1996, 2(1):100-102.

Cui, J. Jean., "A New Challenging and Promising Era of Tyrosine Kinase Inhibitors", ACS Med Chem Lett., 2014, 5(4):272-274.

Curiel et al., "Blockade of B7-H1 improves myeloid dendritic cell-mediated antitumor immunity", In Nature medicine, 2003, 9(5):562-567.

Dagher et al., "c-Kit and CD38 are expressed by long-term reconstituting hematopoietic cells present in the murine yolk sac," Biol Blood Marrow Transplant, 1998, 4(2):69-74.

Davies et al., "Antibody VH Domains as Small Recognition Units," Bio/Technology, May 13, 1995, 13(5):475-479.

Davis et al., "Natural killer cells unleashed: Checkpoint receptor blockade and BiKE/TriKE utilization in NK-mediated anti-tumor immunotherapy", Semin Immunol., 2017, 31:64-75.

Dawson et al., "Synthesis of proteins by native chemical ligation," Science, Nov. 1994, 266(5186):776-779.

De Kruif et al., "Selection and Application of Human Single Chain Fv Antibody Fragments from a Semi-synthetic Phage Antibody Display Library with Designed CDR3 Regions," Journal of Molecular Biology, Apr. 1995, 248(1):97-105.

De la Pena et al., "Expression of the matrix metalloproteases 2, 14, 24, and 25 and tissue inhibitor 3 as potential molecular markers in advanced human gastric cancer." Disease markers 2014 (2014).

Deaglio et al., "CD38 is a signaling molecule in B-cell chronic lymphocytic leukemia cells," Blood, Sep. 15, 2003, 102(6):2146-2155.

Debre et al., "Infusion of Fc gamma fragments for treatment of children with acute immune thrombocytopenia purpura", Lancet, 1993, 342(8877):945-949.

Deonarain et al., "Small-Format Drug Conjugates: A Viable Alternative to ADCs for Solid Tumours?", Antibodies (Basel), 2018, 7(2):16.

Derossi et al., "The third helix of the Antennapedia homeodomain translocates through C108lbiological membranes," Journal if Biological Chemistry, Apr. 1994, 269(14):10444-10450.

Deyle et al., "Phage Selection of Cyclic Peptides for Application in Research and Drug Development," Accounts of Chemical Research, 2017, 50(8):1866-1874.

Di, "Strategic Approaches to Optimizing Peptide ADME Properties," AAPS J., Jan. 2015, 17(1):134-143.

Diamantis and Banerji, "Antibody-drug conjugates—an emerging class of cancer treatment." British journal of cancer, 2016, 114(4):362-367.

Diaz-Perlas et al., "Branched BBB-shuttle peptides: chemoselective modification of proteins to enhance blood-brain barrier transport," Chemical Science, Sep. 2018, 9(44):8409-8415.

Dong, et al. "Tumor-associated B7-H1 promotes T-cell apoptosis: a potential mechanism of immune evasion", Nature Medicine, 2002, 8(8):793-800.

Dorfman et al., "Programmed death-1 (PD-1) is a marker of germinal center-associated T cells and angioimmunoblastic T-cell lymphoma." The American journal of surgical pathology, Jul. 2006, 30(7):802-810.

Driggers et al., "The exploration of macrocycles for drug discovery—an underexploited structural class," Nature Reviews Drug Discovery, Jul. 2008, 7(7):608-624.

Dubois et al., "New ways to image and target tumour hypoxia and its molecular responses," Radiotherapy and Oncology, Sep. 2015, 116(3):352-357.

Dufort et al., "789: Generation of a Bicycle NK-TICA(TM), a novel NK cell engaging molecule to enhance targeted tumor cytotoxicity", Nov. 10, 2021, 9(Suppl 2):A824-A824. URL: https://jitc.bmj.com/contenl/jitc/9/Suppl_2/A824.full.pdf.

Dunne et al., "EphA2 Expression Is a Key Driver of Migration and Invasion and a Poor Prognostic Marker in Colorectal Cancer," Clin Cancer Res., Jan. 1, 2016, 22(1):230-242.

Duong and Rodan, "The role of integrins in osteoclast function," J Bone Miner Metab., 1999, 17(1):1-6.

Eagan et al., "Early clinical study of an intermittent schedule for maytansine (NSC-153858): brief communication." Journal of the National Cancer Institute, 1978, 60(1):93-96.

Eisenhauer et al., "New response evaluation criteria in solid tumours: revised RECIST guideline (version 1.1)." European journal of cancer, 2009, 45(2):228-247.

Ellenrieder et al., "Role of MT-MMPs and MMP-2 in pancreatic cancer progression." International Journal of Cancer, 2000, 85(1):14-20.

Elson-Schwab et al., "Guanidinylated neomycin delivers large, bioactive cargo into cells through a heparan sulfate-dependent pathway." Journal of Biological Chemistry, 2007, 282(18):13585-13591.

Fauriat et al., "Deficient expression of NCR in NK cells from acute myeloid leukemia: Evolution during leukemia treatment and impact of leukemia cells in NCRdull phenotype induction", Blood, 2007, 109(1):323-330.

Fehrenbacher et al., "Atezolizumab versus docetaxel for patients with previously treated non-small-cell lung cancer (POPLAR): a multicentre, open-label, phase 2 randomised controlled trial." The Lancet, 2016, 387(10030): 1837-1846.

Felices et al., "Generation of BiKEs and TriKEs to Improve NK Cell-Mediated Targeting of Tumor Cells", Methods Mol Biol., 2016, 1441:333-346.

Felices et al., "Novel CD19-targeted TriKE restores NK cell function and proliferative capacity in CLL", Blood Adv., 2019, 3(6):897-907.

Fiacco et al., "N-Methyl Scanning Mutagenesis Generates Protease-Resistant G Protein Ligands with Improved Affinity and Selectivity," ChemBioChem, Sep. 2008, 9(14):2200-2203.

Figure 3.8 of "Immunobiology: The Immune System in Health and Disease," Garland Science, 2001.

Flaherty et al., "Nonclinical evaluation of GMA161—an antihuman CD16 (FcγRIII) monoclonal antibody for treatment of autoimmune disorders in CD16 transgenic mice", Toxicological Sciences, 2012, 125(1):299-309.

Francis et al., "Bone and Soft Tissue Sarcomas: UK Incidence and Survival: 1996-2010," National Cancer Intelligence Network, Nov. 2013, v2.0.

Fumet et al. "Phase Ib/II trial evaluating the safety, tolerability and immunological activity of durvalumab (MEDI4736) (anti-PD-L1) plus tremelimumab (anti-CTLA-4) combined with FOLFOX in patients with metastatic colorectal cancer." ESMO open, 2018, 3(4):e000375.

Funaro et al., "Human CD38 is associated to distinct molecules which mediate transmembrane signaling in different lineages." European journal of immunology, Oct. 1993, 23(10):2407-2411.

Funaro et al., "Involvement of the multilineage CD38 molecule in a unique pathway of cell activation and proliferation," J Immunol., Oct. 1990, 145(8):2390-2396.

Galsky et al., "Phase I trial of the prostate-specific membrane antigen-directed immunoconjugate MLN2704 in patients with progressive metastatic castration-resistant prostate cancer." Journal of clinical oncology, 2008, 26(13):2147-2154.

Gandhi et al., "MP69-11 Carbonic Anhydrase IX Assay: A Paradigm Shift in Diagnosis of Malignant Cystic Renal Lesions," J Urol., May 18, 2015, 193(4S):e870-e871.

(56) References Cited

OTHER PUBLICATIONS

Garcia-Iglesias et al., "Low NKp30, NKp46 and NKG2D expression and reduced cytotoxic activity on NK cells in cervical cancer and precursor lesions", BMC Cancer, Jun. 16, 2009, 9:186, 8 pages.
Gauthier et al., "Multifunctional Natural Killer Cell Engagers Targeting NKp46 Trigger Protective Tumor Immunity", Cell, 2019, 177(7):1701-1713.
Gelb et al., "Abstract 391: Molecular-based enrichment strategy for Nectin-4 targeted Bicycle toxin conjugate BT8009," Cancer Res., Jul. 1, 2021, 81(13 suppl):391 (poster).
Gelb et al., "Abstract A047: MT1-MMP Immunohistochemistry (IHC) analysis of tumor microarrays (TMAs) using a novel scoring system guides patient selection for BT1718 expansion cohorts," In Molecular Cancer Therapeutics, 2019, 18(12_Suppl):A047.
Gen path diagnostics, "Solid Tumors", Accessed on https://genpathdiagnostics.com/patients/oncology/solid-tumors/, Jun. 30, 2023, 4 pages.
Gentilucci et al., "Chemical Modifications Designed to Improve Peptide Stability: Incorporation of Non-Natural Amino Acids, Pseudo-Peptide Bonds, and Cyclization," Current Pharmaceutical Design, 2010, 16(28):3185-3203.
Gfeller et al., "Current tools for predicting cancer-specific T cell immunity," Oncoimmunology, 2016, 5(7):e1177691.
Gleason et al., "CD16xCD33 bispecific killer cell engager (BiKE) activates NK cells against primary MDS and MDSC CD33+ targets", Blood, 2014, 123(19):3016-3026.
Gokel et al., "Crown Ethers: Sensors for Ions and Molecular Scaffolds for Materials and Biological Models," Chem. Rev., 2004, 104(5):2723-2750.
Gradishar et al., "Significantly longer progression-free survival with nab-paclitaxel compared with docetaxel as first-line therapy for metastatic breast cancer." J Clin Oncol., 2009, 27(22):3611-3619.
Gresh, "Neuroblastoma," Merck Manual., Retrieved form: |https://www.msdmanuals.com/en-in/professional/pediatrics/pediatric-cancers/neuroblastoma, Sep. 2022, 4 pages.
Griffiths et al., "Isolation of high affinity human antibodies directly from large synthetic repertoires," EMBO Journal, Jul. 1994, 13(14):3245-3260.
Grisold et al., "Peripheral neuropathies from chemotherapeutics and targeted agents: diagnosis, treatment, and prevention." Neuro-oncology, 2012, 14(suppl_4):iv45-iv54.
Gu et al., "The influence of the penetrating peptide iRGD on the effect of paclitaxel-loaded MT1-AF7p-conjugated nanoparticles on glioma cells." Biomaterials, 2013, 34(21):5138-5148.
Guo et al., "Prognostic significance of combinations of RNA-dependent protein kinase and EphA2 biomarkers for NSCLC," J Thorac Oncol., Mar. 2013, 8(3):301-308.
Gupta et al., "Intracellular delivery of large molecules and small particles by cell-penetrating proteins and peptides," Advanced Drug Delivery Reviews, Feb. 2005, 57(4):637-651.
Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.
Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018:6248590, 10 pages.
Hanna et al., "Randomized phase III trial of pemetrexed versus docetaxel in patients with non-small-cell lung cancer previously treated with chemotherapy." Journal of clinical oncology, 2004, 22(9):1589-1597.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res., 2017, 77(13 suppl):5144.
Hart, et al., "De novo identification of lipid II binding lipopeptides with antibacterial activity against vancomycin-resistant bacteria." Chemical Science, 2017, 8(12):7991-7997.
Hart, et al., "Cell binding and internalization by filamentous phage displaying a cyclic Arg-Gly-Aspcontaining peptide", J. Biol. Chem., 1994, 269:12468-12474.
Hasmim et al., "Critical Role of Tumor Microenvironment in Shaping NK Cell Functions: Implication of Hypoxic Stress", Frontiers in Immunology, Sep. 23, 2015, 6:482, 9 pages.
He et al., "Matrix metalloproteinase-14 is a negative prognostic marker for patients with gastric cancer." Digestive diseases and sciences, 2013, 58:1264-1270.
Helft et al., "A phase I study of cantuzumab mertansine administered as a single intravenous infusion once weekly in patients with advanced solid tumors." Clinical cancer research, 2004, 10(13):4363-4368.
Henriques et al., "Functional characterization of peripheral blood dendritic cells and monocytes in systemic lupus erythematosus", Rheumatology International, Apr. 2012, 32(4):863-869.
Herbst et al., "Pembrolizumab versus docetaxel for previously treated, PD-L 1-positive, advanced non-small-cell lung cancer (KEY-NOTE-010): a randomised controlled tria", Lancet, Apr. 2016, 387(10027):1540-1550.
Hershman, "Thyroid Cancers," Merck Manual, Retrieved from: https://www.merckmanuals.com/professional/endocrine-and-metabolic-disorders/thyroid-disorders/thyroid-cancers, Sep. 2020.
Hess et al., "Backbone Cyclic Peptidomimetic Melanocortin-4 Receptor Agonist as a Novel Orally Administrated Drug Lead for Treating Obesity," Journal of Medicinal Chemistry, Jan. 26, 2008, 51(4):1026-1034.
Hess et al., "Molecular Regulation of Tumor Cell Vasculogenic Mimicry by Tyrosine Phosphorylation: Role of Epithelial Cell Kinase (Eck/EphA2", Cancer Research, 2001, 61(8):3250-3255.
Hikari et al., "Tags for labeling protein N-termini with subtiligase for proteomics", Bioorganic & Medicinal Chemistry Letters, Nov. 2008, 18 (22):6000-6003.
Hill et al: "Constraining Cyclic Peptides to Mimic Protein Structure Motifs", Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research, Oct. 2019, 23(19):5878-5889.
Hirano et al. "Blockade of B7-H1 and PD-1 by monoclonal antibodies potentiates cancer therapeutic immunity," Cancer Research, 2005, 65(3):1089-1096.
Hoogenboom et al., "By-passing immunisation. Human antibodies from synthetic repertoires of germline VH gene segments rearranged in vitro," Journal of Molecular Biology, Sep. 1992, 227(2):381-388.
Hoshino et al., "Mapping of the catalytic and epitopic sites of human CD38/NAD+ glycohydrolase to a functional domain in the carboxyl terminus," J Immunol., Jan. 15, 1997, 158(2):741-747.
Hsu et al., "Efficacy of plasmin-treated intravenous gamma-globulin for therapy of Kawasaki syndrome", The Pediatric Infectious Disease Journal, Jun. 1993, 12(6):509-512.
Hu-Lieskovan and Ribas, "New Combination Strategies Using Programmed Cell Death 1/Programmed Cell Death Ligand 1 Checkpoint Inhibitors as a Backbone," Cancer J., Jan./Feb. 2017, 23(1):10-22.
Hurov et al., "BT7480, a novel fully synthetic tumor-targeted immune cell agonist (TICA™) induces tumor localized CD137 agonism", Retrieved from the Internet: URL: https://www.bicycletherapeutics.com/wp-content/uploads/2020-06-16-BT7480-AACR-2020-poster-P5552_Final_CD137-in-title-002.pdf, Jun. 20, 2020, 1 page.
Ide et al., "A novel method for artificial lipid-bilayer formation," Biosensors and Bioelectronics, 2005, 21(4):672-677.
Inman et al., "PD-L1 (B7-H1) expression by urothelial carcinoma of the bladder and BCG-induced granulomata: associations with localized stage progression", Cancer, 2007, 109(8):1499-1505.
Ip et al., "Atypical localization of membrane type 1-matrix metalloproteinase in the nucleus is associated with aggressive features of hepatocellular carcinoma." Molecular Carcinogenesis: Published in cooperation with the University of Texas MD Anderson Cancer Center, 2007, 46(3):225-230.

(56) References Cited

OTHER PUBLICATIONS

Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Jackson and Stover, "Using the lessons learned from the clinic to improve the preclinical development of antibody drug conjugates." Pharmaceutical research, 2015, 32(11):3458-3469.
Jackson et al., "A human antibody-drug conjugate targeting EphA2 inhibits tumor growth in vivo", Cancer Research, Nov. 15, 2008, 68(22):9367-9374.
Jespers et al., "Selection of optical biosensors from chemisynthetic antibody libraries," Protein Engineering, Design and Selection, Oct. 2004, 17(10):709-713.
Jin et al., "αVβ3 Integrin-Targeted Radionuclide Therapy with 64Cu-cyclam-RAFT-c(-RGDfK-)4," Mol Cancer Ther., Sep. 2016, 15(9):2076-2085.
Johnson et al., "Melanoma-specific MHC-II expression represents a tumour-autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Jones et al., "Randomized phase III study of docetaxel compared with paclitaxel in metastatic breast cancer." Journal of Clinical Oncology, 2005, 23(24):5542-5551.
Jones et al., "Targeting membrane proteins for antibody discovery using phage display," Scientific Reports, May 18, 2016, 6(1):1-11.
Kamat et al., "The clinical relevance of stromal matrix metalloproteinase expression in ovarian cancer." Clinical Cancer Research, 2006, 12(6):1707-1714.
Kanazawa et al., "Non-obese-diabetic mice: immune mechanisms of pancreatic β-cell destruction," Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)." (2016): 5-5.
Keith, "Lung Carcinoma," Merck Manual, Retrieved on: |https://www.merckmanuals.com/professional/pulmonary-disorders/tumors-of-the-lungs/lung-carcinoma, Sep. 2021, 18 pages.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.
Kellog et al., "Disulfide-linked antibody—maytansinoid conjugates: Optimization of in vivo activity by varying the steric hindrance at carbon atoms adjacent to the disulfide linkage." Bioconjugate chemistry, 2011, 22(4):717-727.
Kemp and McNamara, "Conformationally restricted cyclic nonapeptides derived from L-cysteine and LL-3-amino-2-piperidone-6-carboxylic acid (LL-Acp), a potent.beta.-turn-inducing dipeptide analog." J. Org. Chem., 1985, 50(26):5834-5838.
Kerkela et al., "Differential patterns of stromelysin-2 (MMP-10) and MT1-MMP (MMP-14) expression in epithelial skin cancers." British journal of cancer, 2001, 84(5):659-669.
Kessenbrock et al., "Matrix metalloproteinases: regulators of the tumor microenvironment." Cell, 2010, 141(1):52-67.
Khan et al., "Engineering Lipid Bilayer Membranes for Protein Studies," International Journal of Molecular Sciences, Nov. 2013, 14(11):21561-21597.
Kikuchi et al., "Immunohistochemical detection of membrane-type-1-matrix metalloproteinase in colorectal carcinoma." British journal of cancer, 2000, 83(2):215-218.
Kim et al., "Synergistic signals for natural cytotoxicity are required to overcome inhibition by c-Cbl ubiquitin ligase", Immunity, Feb. 26, 2010, 32(2):175-186.

Kinch et al., "Predictive Value of the EphA2 Receptor Tyrosine Kinase in Lung Cancer Recurrence and Survival", Clin Cancer Res., 2003, 9(2):613-618.
Kitanaka et al., "CD38 ligation in human B cell progenitors triggers tyrosine phosphorylation of CD19 and association of CD19 with lyn and phosphatidylinositol 3-kinase," J Immunol., 1997, 159(1):184-192.
Kitanaka et al., "CD38-mediated signaling events in murine pro-B cells expressing human CD38 with or without its cytoplasmic domain," J Immunol., Feb. 15, 1999, 162(4):1952-1958.
Kleinau et al., "Induction and suppression of collagen-induced arthritis is dependent on distinct fcgamma receptors", J Exp Med., May 2000, 191(9):1611-1616.
Knight et al., "Three genes for lupus nephritis in NZB x NZW mice," Journal of Experimental Medicine, Jun. 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Konopleva et al., "Ligation of cell surface CD38 protein with agonistic monoclonal antibody induces a cell growth signal in myeloid leukemia cells," J Immunol., Nov. 1, 1998, 161(9):4702-4708.
Koo et al., "Reduction of the CD16-CD56bright NK Cell Subset Precedes NK Cell Dysfunction in Prostate Cancer", PLoS One, 2013, 8(11):e78049, 8 pages.
Kreidieh et al., "Overview, prevention and management of chemotherapy extravasation." World journal of clinical oncology, 2016, 7(1):87.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Krop et al., "Trastuzumab emtansine versus treatment of physician's choice for pretreated HER2-positive advanced breast cancer (TH3RESA): a randomised, open-label, phase 3 trial." The Lancet Oncology, 2014, 15(7):689-699.
Kumagai et al., "Ligation of CD38 suppresses human B lymphopoiesis," J Exp Med., Mar. 1, 1995, 181(3):1101-1110.
Kylväjä, et al., "Penicillin binding protein 3 of Staphylococcus aureus NCTC 8325-4 binds and activates human plasminogen." BMC research notes, 2016, 9:1-10.
Landolt et al., "Clear cell renal cell carcinoma is linked to epithelial-to-mesenchymal transition and to fibrosis." Physiological reports, 2017, 5(11):e13305.
Lani et al., "Identification of high affinity, highly selective bicyclic peptides (Bicycles®) to transmembrane proteins using phage display screening on whole cells," Abstract, PEGS Summit, Boston, Massachusetts, May 2017, 1 page.
Lanman et al., "Analytical and Clinical Validation of a Digital Sequencing Panel for Quantitative, Highly Accurate Evaluation of Cell-Free Circulating Tumor DNA", PLoS One, 2015, 10(10):e0140712.
Laudanski et al., "Increased serum level of membrane type 1-matrix metalloproteinase (MT1-MMP/MMP-14) in patients with breast cancer." Folia histochemica et cytobiologica, 2010, 48(1):101-103.
Lea and Simeonov, "Fluorescence polarization assays in small molecule screening," Expert Opinion in Drug Discovery, Jan. 2011, 6(1):17-32.
Lee and Aarhus, "ADP-ribosyl cyclase: an enzyme that cyclizes NAD+ into a calcium-mobilizing metabolite," Cell Regul., Mar. 1991, 2(3):203-209.
Lee et al., "ADP-ribosyl cyclase and CD38. Multi-functional enzymes in Ca+2 signaling," Adv Exp Med Biol., 1997, 419:411-419.
Lee et al., "Structural determination of a cyclic metabolite of NAD+ with intracellular Ca2+-mobilizing activity," J Biol Chem., Jan. 25, 1989, 264(3):1608-1615.
Leighton, "Pharmacology Review: Kadcyla (ado-trastuzumab emtansine)," In Center for Drug Evaluation and Research Application No. 1254270rio1 sOOO., Feb. 2020.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.

(56) References Cited

OTHER PUBLICATIONS

Li et al., "Fluorescent Mu selective opioid ligands from a mixture based cyclic peptide library." ACS combinatorial science, 2012, 14(12):673-679.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated with the progression and prognosis in breast cancer." American Journal of Translational Research, 2015, 7(1):120.
Li et al., "Up-regulation of EphA2 and down-regulation of EphrinA1 are associated with the aggressive phenotype and poor prognosis of malignant glioma", Tomor Biology, 2010, 31(5):477-488.
Li, et al., "A novel strategy for in vitro selection of peptide-drug conjugates." Chemistry & biology, 2003, 10(3):233-239.
Li, et al., "Increasing the antimicrobial activity of nisin-based lantibiotics against Gram-negative pathogens." Applied and environmental microbiology, 2018, 84(12):e00052-18.
Lian at al., Screening Bicyclic Peptide Libraries for Protein-Protein Interaction Inhibitors: Discovery of Journal of the American Chemical Society, Aug. 14, 2013, 135(32):11990-11995.
Lian et al., "Cell-Permeable Bicyclic Peptide Inhibitors against Intracellular Proteins", Journal of the American Chemical Society, Jul. 2014, 136(28):9830-9833.
Lin et al., "EphA2 overexpression is associated with angiogenesis in ovarian cancer," Cancer, Jan. 15, 2007, 109(2):332-340.
Linch et al., "OX40 Agonists and Combination Immunotherapy: Putting the Pedal to the Metal," Frontiers in Oncology, Feb. 16, 2015, 5(34):1-14.
Linde et al., "Structure-Activity Relationship and Metabolic Stability Studies of Backbone Cyclization and N-Methylation of Melanocortin Peptides," Biopolymers, 2008, 90(5):671-682.
Lindstrom et al., "Myasthenia gravis," Advances in Immunology, Dec. 1988, 42:233-284.
Liu et al., "Abstract 3642: Tumor-antigen expression-dependent activation of the CD137 costimulatory pathway by bispecific DART proteins," American Association for Cancer Research, Jul. 2017, 77(supp 13):1-4.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway", Blood, 2007, 110(1): 296-304.
Lopus, Manu. "Antibody-DM1 conjugates as cancer therapeutics." Cancer letters, 2011, 307(2):113-118.
Lovering et al. "Escape from flatland: increasing saturation as an approach to improving clinical success." Journal of medicinal chemistry, 2009, 52(21):6752-6756.
Lovering, "Escape from Flatland 2: complexity and promiscuity," Meducinal Chemistry Communication, Dec. 2012, 4(3):515-519.
Lund et al., "CD38 signaling in B lymphocytes is controlled by its ectodomain but occurs independently of enzymatically generated ADP-ribose or cyclic ADP-ribose," J Immunol., Mar. 1, 1999, 162(5):2693-2702.
M.D. Anderson Cancer Center, "Nivolumab and HPV-16 Vaccination in Patients With HPV-16 Positive Incurable Solid Tumors," In ClinicalTrials.gov Identifier NCT02426892. Retrieved form https://clinicaltrials.gov/ct2/show/study/NCT02426892, 2015.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235.
Macheboeuf et al., "Penicillin binding proteins: key players in bacterial cell cycle and drug resistance processes", FEMS Microbiol Rev., 2006, 30(5):673-691.
Mallone et al., "Signaling through CD38 induces NK cell activation," Int Immunol., Apr. 1, 2001, 13(4):397-409.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., "In vitro mechanisms of action of rituximab on primary non-Hodgkin lymphomas", Blood, 2003, 101(3):949-954.
Mark, "Renal Cell Carcinoma," Merck Manual, Retrieved form: https://www.merckmanuals.com/home/kidney-and-urinary-tract-disorders/cancers-of-the-kidney-and-genitourinary-tract/kidney-cancer, Sep. 2021.
Marks et al., "By-passing immunization. Human antibodies from V-gene libraries displayed on phage," Journal of Molecular Biology, Dec. 1991, 222(3):581-597.
Marme, "VEGFs, angiopoietins, Ephrins and their receptors: putative targets for tumor therapy?" Ann Hematol., 2002, 81(Suppl 2):S66.
Maron et al., "H-2K mutation controls immune response phenotype of autoimmune thyroiditis. Critical expression of mutant gene product in both thymus and thyroid glands," Journal of Experimental Medicine, Oct. 1980, 152(4):1115-1120.
McFarlin et al., "Experimental Allergic Encephalomyelitis in the Rat: Response to Encephalitogenic Proteins and Peptides," Science, Feb. 1973, 179(4072):478-480.
Merck Manual (https://www.merckanuals.com/home/blood-disorders/plasma-celldisorders/multiple-myeloma?query-pancreaticu ltiple%20myeloma accessed Apr. 9, 2021).
Merritt et al., "Analysis of EphA2 expression and mutant p53 in ovarian carcinoma," Cancer Biol Ther., Oct. 2006, 5(10):1357-1360.
Milowsky et al., Phase 1/2 multiple ascending dose trial of the prostate-specific Membrane antigen-targeted antibody drug conjugate MLN2704 in metastatic castration-resistant prostate cancer. In Urologic Oncology: Seminars and Original Investigations, 2016, 34(12):530-e15.
Mitra et al., "Structure-Activity Relationship Analysis of Peptides Targeting the EphA2 Receptor," Biochemistry, 2010, 49(31):6687-6695.
Miyoshi and Takai, "Nectin and nectin-like molecules: biology and pathology," Am J Nephrol., 2007, 27(6):590-604.
Mohammad et al., Prognostic value of membrane type 1 and 2 matrix metalloproteinase expression and gelatinase A activity in bladder cancer. The International journal of biological markers, 2010, 25(2):69-74.
Moore et al., "A novel bispecific antibody format enables simultaneous bivalent and monovalent co-engagement of distinct target antigens", Mabs, 2011, 3(6):546-557.
Moraes et al., "Immune checkpoint inhibitors (anti PD-1 or anti PD-L1) versus chemotherapy for second- or third-line treatment of metastatic non-small cell lung cancer," Cochrane Database Syst Rev., 2017, 2017(4):CD012644.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Morra et al., "CD38 is functionally dependent on the TCR/CD3 complex in human T cells," FASEB J., May 1998, 12(7):581-592.
Mudali et al., "Patterns of EphA2 protein expression in primary and metastatic pancreatic carcinoma and correlation with genetic status", Clinical & Experimental Metastasis, 2006, 23(7-8):357-365.
Mudd et al., "Identification and Optimization of EphA2-Selective Bicycles for the Delivery of Cytotoxic Payloads," J Med Chem., 2020, 63(8):4107-4116.
Mugera and Ward, "Acute toxicity of maytansine in F344 rats." Cancer Treatment Reports, 1977, 61(7):1333-1338.
Mullis et al., "Specific synthesis of DNA in vitro via a polymerase-catalyzed chain reaction," Methods in Enzymology, Jan. 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.

(56) References Cited

OTHER PUBLICATIONS

Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakamoto and Bergemann, "Diverse roles for the Eph family of receptor tyrosine kinases in carcinogenesis," Microsc Res Tech., Oct. 2002, 59(1):58-67.
Nakamura et al., "EPHA2/EFNA1 expression in human gastric cancer", Cancer Science, Jan. 2005, 96(1):42-47.
Nakamura et al., "Involvement of alpha(v)beta3 integrins in osteoclast function," J Bone Miner Metab., 2007, 25(6):337-344.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et al., "The therapeutic potential of 4-1BB (CD137) in cancer", Current cancer drug targets, 2005, 5(5):357-363.
Nan et al., "Dual function glutamate-related ligands: discovery of a novel, potent inhibitor of glutamate carboxypeptidase II possessing mGluR3 agonist activity," J Med Chem., Mar. 9, 2000, 43(5):772-774.
National cancer institute, "Cancer prevention overview", (https://www.cancer.gov/about-cancer/causes-prevention/patient-prevention-overview-pdq accessed May 8, 2020), 2020, 12 pages.
National Cancer Institute, "What is Cancer", (https://www.cancer.gov/about-cancer/understanding/what-is-cancer, accessed Apr. 9, 2021), 10 pages.
National Cancer Institute, Understanding Cancer and Related Topics, (https://www.cancer.gov/about-cancer/understanding/what-is-cancer, accessed Apr. 9, 2021).
Nayyar et al., "Overcoming Resistance to Natural Killer Cell Based Immunotherapies for Solid Tumors", Feb. 11, 2019 ;9:51, 28 pages.
Neri and Supuran, "Interfering with pH regulation in tumours as a therapeutic strategy," Nature Review Drug Discovery, Sep. 2011, 10(10):767-777.
Nestor et al., "The Medicinal Chemistry of Peptides," Curr. Medicinal Chem, 2009, 16(33):4399-4418.
Nguyen, "Colorectal Cancer," Merck Manual, Retrieved from https://www.merckmanuals.com/professional/gastrointestinal-disorders/tumors-of-the-gastrointestinal-tract/colorectal-cancer, 2021.
Nguyen, "Pancreatic Cancer", Merck Manual (https://merckmanuals.com/professional/gastrointestinal-disorders/tumors-of-the-gastrointestinal-tract/pancreatic-cancer?query=adenocarcinomas), Sep. 2022, 4 pages.
NIH National Human Genome Research Institute, "Animal Model," Genome.gov., Jan. 4, 2022.
Nishiwada et al., "Nectin-4 expression contributes to tumor proliferation, angiogenesis and patient prognosis in human pancreatic cancer," Journal of Experimental & Clinical Cancer Research, 2015, 34(1):30. (9 pages.).
Nissim et al., "Antibody fragments from a 'single pot' phage display library as immunochemical reagents," EMBO Journal, Feb. 1994, 13(3):692-698.
Nomi et al., "Clinical Significance and Therapeutic Potential of the Programmed lDeath-1 Ligand/Programmed Death-1 Pathway in Human Pancreatic Cancer", Clin Cancer Res., 2007, 13(7): 2151-2157.
Oehlke et al., "Cellular uptake of an alpha-helical amphipathic model peptide with the potential to deliver polar compounds into the cell interior non-endocytically," Biochimica et Biophysica Acta, Nov. 1998, 1414(1-2):127-139.
Okazaki et al., "A Rheostat for Immune Responses: The Unique Properties of PD-1 and Their Advantages for Clinical Application," Nat. Immunol., 2013, 14(12):1212-1218.
Okuyama et al., "Small-molecule mimics of an a-helix for efficient transport of proteins into cells," Nature Methods, Feb. 2007, 4(2):153-159.

Oliver et al., "Mouse CD38 is down-regulated on germinal center B cells and mature plasma cells," J Immunol., Feb. 1997, 158(3):1108-1115.
Ortiz et al., "Elucidating the interplay between IgG-Fc valency and FcγR activation for the design of immune complex inhibitors", Science Translational Medicine, Nov. 2016, 8(365):365ra158.
Pahwa et al., "Monitoring and inhibiting MT1-MMP during cancer initiation and progression." Cancers, 2014, 6(1):416-435.
Partida-Sanchez et al., "Cyclic ADP-ribose production by CD38 regulates intracellular calcium release, extracellular calcium influx and chemotaxis in neutrophils and is required for bacterial clearance in vivo," Nat Med., Nov. 2001, 7(11):1209-1216.
Partida-Sanchez et al., "Regulation of dendritic cell trafficking by the ADP-ribosyl cyclase CD38: impact on the development of humoral immunity," Immunity, Mar. 2004, 20(3):279-291.
Pasero et al., "Highly effective NK cells are associated with good prognosis in patients with metastatic prostate cancer", Oncotarget 6(16), Jun. 10, 2015, 14360-14373.
Pavlidou et al., "Nanodiscs Allow Phage Display Selection for Ligands to Non-Linear Epitopes on Membrane Proteins," PLoS One, Article No. e72272, Sep. 2013, 8(9):8 pages.
Pavlova et al., "A role for PVRL4-driven cell-cell interactions in tumorigenesis," Elife., Apr. 30, 2013, 2:e00358, 24 pages.
Pearson et al., "High-Level Clonal FGFR Amplification and Response to FGFR Inhibition in a Translational Clinical Trial", Cancer Discovery, 2016, 6(8):838-851.
Peng et al., Combined features based on MT1-MMP expression, CD11b+ immunocytes density and LNR predict clinical outcomes of gastric cancer. Journal of translational medicine, 2013, 11(1):1-11.
Phichith, et al., "Novel peptide inhibiting both TEM-1 β-lactamase and penicillin-binding proteins." The FEBS Journal, 2010, 277(23):4965-4972.
Pietraszek et al., "Lumican: a new inhibitor of matrix metalloproteinase-14 activity," FEBS Lett., Nov. 28, 2014, 588(23):4319-4324.
Pivot et al., "Pooled analyses of eribulin in metastatic breast cancer patients with at least one prior chemotherapy." Annals of Oncology, 2016, 27(8):1525-1531.
Platonova et al., "Profound coordinated alterations of intratumoral NK cell phenotype and function in lung carcinoma", Cancer Res., 2011, 71(16):5412-5422.
Polakis, "Antibody Drug Conjugates for Cancer Therapy," Pharmacol Rev., Jan. 2016, 68(1):3-19.
Poliakov et al., "Diverse roles of eph receptors and ephrins in the regulation of cell migration and tissue assembly", Developmental Cell, Oct. 2004;7(4):465-480.
Poon et al., Preclinical safety profile of trastuzumab emtansine (T-DM1): mechanism of action of its cytotoxic component retained with improved tolerability. Toxicology and applied pharmacology, 2013, 273(2):298-313.
Poreba, "Protease-activated prodrugs: strategies, challenges, and future directions." The FEBS Journal, 2020, 287(10):1936-1969.
Pricop et al., "Differential modulation of stimulatory and inhibitory Fc gamma receptors on human monocytes by Th1 and Th2 cytokines", Journal of Immunology, 2001, 166(1):531-537.
Purdie and Benoiton, "Piperazinedione formation from esters of dipeptides containing glycine, alanine, and sarcosine: the kinetics in aqueous solution." Journal of the Chemical Society, Perkin Transactions 2, 1973, 14: 1845-1852.
Qi et al., "Serial determination of glomerular filtration rate in conscious mice using FITC-inulin clearance," American Journal of Physiology—Renal Physiology, Mar. 2004, 286(3):F590-F596.
Ramirez et al., "Defining causative factors contributing in the activation of hedgehog signaling in diffuse large B-cell lymphoma," Leuk Res., Oct. 2012, 36(10):1267-1273.
Randall et al., "Expression of murine CD38 defines a population of long-term reconstituting hematopoietic stem cells," Blood, May 15, 1996, 87(10):4057-4067.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.

(56) References Cited

OTHER PUBLICATIONS

Ravetch et al., "IgG Fc receptors", Annual Review of Immunology, 2001:19:275-290.
Reagan-Shaw et al., "Dose translation from animal to human studies revisited," FASEB J., Mar. 2008, 22(3):659-661.
Reinertsen et al., "B-Lymphocyte Alloantigens Associated with Systemic Lupus Erythematosus," The New England Journal of Medicine, Sep. 7, 1978, 299(10):515-518.
Remacle et al., "Membrane type I-matrix metalloproteinase (MT1-MMP) is internalised by two different pathways and is recycled to the cell surface." Journal of cell science, 2003, 116(19):3905-3916.
Remacle et al., "Novel MT1-MMP small-molecule inhibitors based on insights into hemopexin domain function in tumor growth," Cancer Res., May 1, 2012, 72(9):2339-2349.
Rhodes and Pei, "Bicyclic Peptides as Next-Generation Therapeutics," Chemistry, Sep. 18, 2017, 23(52):12690-12703.
Ridderstad and Tarlinton, "Kinetics of establishing the memory B cell population as revealed by CD38 expression," J Immunol., May 15, 1998, 160(10):4688-4695.
Riddle et al., "Tumor cell surface display of immunoglobulin heavy chain Fc by gene transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodan and Rodan, "Integrin function in osteoclasts," J Endocrinol., Sep. 1997, 154(Suppl):S47-S56.
Rodon et al., "Cantuzumab mertansine in a three-times a week schedule: a phase I and pharmacokinetic study." Cancer chemotherapy and pharmacology, 2008, 62(5):911-919.
Ross and Christiano, "Nothing but skin and bone," J Clin Invest., May 2006, 116(5):1140-1149.
Ross et al., "Bispecific T Cell Enager (BiTE) Antibody Constructs Can Mediate Bystander Tumor Cell Killing", Plos One, Aug. 24, 2017, 12(8):1-24.
Rostovtsev et al., "A Stepwise Huisgen Cycloaddition Process: Copper(I)-Catalyzed Regioselective "Ligation" of Azides and Terminal Alkynes," Angewandte Chemie, Jul. 2002, 41(14):2596-2599.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007, 25(22):3217-3023.
Rothwell et al., "Utility of ctDNA to support patient selection for early phase clinical trials: the TARGET study", Nature Medicine, 2019, 25(5):738-743.
Rudgers et al., "Binding properties of a peptide derived from beta-lactamase inhibitory protein." Antimicrob Agents Chemother., 2001, 45(12):3279-3286.
Salmon et al., "Human receptors for immunoglobulin G: key elements in the pathogenesis of rheumatic disease", Arthritis & Rheumatology, 2001, 44(4):739-750.
Satoh et al., "Experimental allergic encephalomyelitis mediated by murine encephalitogenic T cell lines specific for myelin proteolipid apoprotein," Journal of Immunology, Jan. 1987, 138(1):179-184.
Sausville and Burger, "Contributions of Human Tumor Xenografts to Anticancer Drug Development," Cancer Res., 2006, 66(7):3351-3354.
Scagliotti et al., "Phase III study comparing cisplatin plus gemcitabine with cisplatin plus pemetrexed in chemotherapy-naive patients with advanced-stage non-small-cell lung cancer." Journal of clinical oncology, 2008, 26(21):3543-3551.
Schiller et al., "Comparison of four chemotherapy regimens for advanced non-small-cell lung cancer." New England Journal of Medicine, 2002, 346(2):92-98.
Schreiber et al., "Rapid, electrostatically assisted association of proteins," Nature Structural & Molecular Biology, May 1996, 3:427-431.
Schulke et al., "The homodimer of prostate-specific membrane antigen is a functional target for cancer therapy," Proc Natl Acad Sci U SA., Oct. 28, 2003, 100(22):12590-12595.
Seely and Frazier, "Regulatory Forum Opinion Piece*: Dispelling Confusing Pathology Terminology: Recognition and Interpretation of Selected Rodent Renal Tubule Lesions," Toxicol Pathol., 2015, 43(4):457-463.
Segal et al., "Results from an Integrated Safety Analysis of Urelumab, an Agonist Anti-CD137 Monoclonal Antibody", clinical Cancer research, 2017, 23(8):1929-1936.
Seiki et al., "Membrane-type 1 matrix metalloproteinase: a key enzyme for tumor invasion." Cancer letters, 2003, 194(1):1-11.
Sepiashvili et al., "Potentially novel candidate biomarkers for head and neck squamous cell carcinoma identified using an integrated cell line-based discovery strategy." Molecular & Cellular Proteomics, 2012, 11(11):1404-1415.
Shaabani et al., "A patent review on PD-1/PD-L 1 antagonists: small molecules, peptides, and macrocycles (2015-2018)," Expert Opinion on Therapeutic Patents, 2018, 28(9):665-678.
Shah et al., "Phase I study of IMGN901, a CD56-targeting antibody-drug conjugate, in patients with CD56-positive solid tumors." Investigational new drugs, 2016, 34:290-299.
Shah, "Update on metastatic gastric and esophageal cancers." Journal of clinical oncology 33, No. 16 (2015): 1760-1769.
Shao et al., "Copy number variation is highly correlated with differential gene expression: a pan-cancer study," BMC Medical Genetics, Nov. 9, 2019, 20(1):175.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shen et al., "Non-clinical disposition and metabolism of DM1, a Component of Trastuzumab Emtansine (T-DM1), in Sprague Dawley Rats." Drug Metabolism Letters, 2015, 9(2):119-131.
Shen, et.al., "Evaluation of phage display discovered peptides as ligands for prostate-specific membrane antigen (PSMA)." PLoS One, 2013, 8(7):e68339.
Shi et al., "One-Bead-Two-Compound Thioether Bridged Macrocyclic (gamma)-AApeptide Screening Library Against EphA2," J Med Chem., Nov. 22, 2017, 60(22):9290-9298.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Sibaud et al., "Pigmentary disorders induced by anticancer agents. Part I: chemotherapy." In Annales de dermatologie et de venereologie, 2013, 140(3):183-196.
Siddharth et al., "Nectin-4 is a breast cancer stem cell marker that induces WNT/β-Catenin signaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Sordo-Bahamonde et al., "Mechanisms of Resistance to NK Cell Immunotherapy", Cancers (Basel). Apr. 7, 2020, 12(4):893.
Sounni et al."MT1-MMP expression promotes tumor growth and angiogenesis through an up-regulation of vascular endothelial growth factor expression" FASEB J., 2002, 16(6):555-564.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood, 2014, 124(21):1760.
Steck et al., "Inside-out red cell membrane vesicles: preparation and purification," Science, Apr. 10, 1970, 168(3928):255-257.

(56) References Cited

OTHER PUBLICATIONS

Stein et al., "Eph receptors discriminate specific ligand oligomers to determine alternative signaling complexes, attachment, and assembly responses", Genes Development, 1998, 12(5):667-678.
Stevenson et al., "Preliminary studies for an immunotherapeutic approach to the treatment of human myeloma using chimeric anti-CD38 antibody," Blood, Mar. 1, 1991, 77(5):1071-1079.
Stojanovic et al., "Natural killer cells and solid tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.
Stuart et al., "Collagen Autoimmune Arthritis," Annual Review of Immunology, 1984, 2:199-218.
Sun et al., "Carbohydrate and protein immobilization onto solid surfaces by sequential Diels-Alder and azide-alkyne cycloadditions," Bioconjugate Chemistry, Jan.-Feb. 2006, 17(1):52-57.
Sun et al., "NK cell receptor imbalance and NK cell dysfunction in HBV infection and hepatocellular carcinoma", Cellular & Molecular Immunology, May 2015, 12(3):292-302.
Suojanen et al., "A novel and selective membrane type-1 matrix metalloproteinase (MT1-MMP) inhibitor reduces cancer cell motility and tumor growth," Cancer Biology & Therapy, Dec. 2009, 8(24):2362-2370.
Supuran, "Carbonic anhydrases: novel therapeutic applications for inhibitors and activators," Nature Reviews Drug Discovery, Feb. 2008, 7(2):168-181.
Tandon et al., "Emerging strategies for EphA2 receptor targeting for cancer therapeutics" Expert Opinion on Therapeutic Targets, 2011, 15(1):31-51.
Tarazona et al., "Current progress in NK cell biology and NK cell-based cancer immunotherapy", Cancer Immunol Immunother, 2020, 69(5):879-899.
Tasch et al., "A unique folate hydrolase, prostate-specific membrane antigen (PSMA): a target for immunotherapy?", Crit Rev Immunol., 2001, 21(1-3):249-261.
Teitelbaum, "Osteoclasts, integrins, and osteoporosis," J Bone Miner Metab., Oct. 2000, 18(6):344-349.
Teitelbaum, "Osteoporosis and Integrins," The Journal of Clinical Endocrinology & Metabolism, Apr. 2005, 90(4):2466-2468.
Teti et al., "The Role of the Alpha Vbeta3 Integrin in the Development of Osteolytic Bone Metastases: A Pharmacological Target for Alternative Therapy?", Calcified Tissue International, Oct. 2002, 71(4):293-299.
Tetu et al., "The influence of MMP-14, TIMP-2 and MMP-2 expression on breast cancer prognosis." Breast Cancer Research, 2006, 8(3):1-9.
Teufel et al., "Backbone-driven collapse in unfolded protein chains," J Mol Biol., Jun. 3, 2011, 409(2):250-262.
Thake et al., "Toxicity of Maytansine (NSC 153858) in dogs and monkeys." PB-US National Technical Information Service (1975), Feb. 1975, 244628.
Thevenard et al., "The YSNSG cyclopeptide derived from tumstatin inhibits tumor angiogenesis by down-regulating endothelial cell migration." International journal of cancer, 2010, 126(5):1055-1066.
Thompson et al., "Costimulatory B7-H1 in renal cell carcinoma patients: Indicator of tumor aggressiveness and potential therapeutic target", Proceedings of the National Academy of Sciences, 2004, 101(49):17174-17179.
Timmerman et al., "Rapid and Quantitative Cyclization of Multiple Peptide Loops onto Synthetic Scaffolds for Structural Mimicry of Protein Surfaces," ChemBioChem, 2005, 6(5):821-824.
Todisco et al., "CD38 ligation inhibits normal and leukemic myelopoiesis," Blood, Jan. 2000, 95(2):535-542.

Tolcher et al., "Cantuzumab mertansine, a maytansinoid immunoconjugate directed to the CanAg antigen: a phase I, pharmacokinetic, and biologic correlative study." Journal of clinical oncology, 2003, 21(2):211-222.
Toogood, "Small Molecule Immuno-oncology Therapeutic Agents," Bioorganic & Medicinal Chemistry Letters, 2018, 28(3):319-329.
Touati et al., "Phage Selection of Bicyclic Peptide Ligands and Development of a New Peptide Cyclisation Method", These No. 5536, Oct. 2012, 117 pages.
Trouche et al., "Small multivalent architectures mimicking homotrimers of the TNF superfamily member CD40L: delineating the relationship between structure and effector function." Journal of the American Chemical Society, 2007, 129(44):13480-13492.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry." Human pathology, 2008, 39(5):731-739.
Tugyi et al., "Partial D-amino acid substitution: Improved enzymatic stability and preserved Ab recognition of a MUC2 epitope peptide," Proceedings of the National Academy of Sciences U.S.A., Jan. 2005, 102(2):413-418.
Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)." Cancer Research, May 2015, 75(9_Suppl):S3-01.
Uckun, "Regulation of human B-cell ontogeny," Blood, Nov. 1990, 76(10):1908-1923.
Ulasov et al., "Inhibition of MMP 14 potentiates the therapeutic effect of temozolomide and radiation in gliomas." Cancer medicine, 2013, 2(4):457-467.
Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.
Upadhyaya, "Activation of CD137 using multivalent and tumor targeted Bicyclic peptides." Cancer Research, Jul. 2019, 79(13 Suppl):3257-3257.
Van Eden et al., "Cloning of the mycobacterial epitope recognized by T lymphocytes in adjuvant arthritis," Nature, Jan. 14, 1988, 331(6152):171-173.
Van Glabbeke et al., "Progression-free rate as the principal endpoint for phase II trials in soft-tissue sarcomas." European Journal of Cancer, 2002, 38(4):543-549.
Vandenbroucke and Libert, "Is there new hope for therapeutic matrix metalloproteinase inhibition?. " Nature reviews Drug discovery, 2014, 13(12):904-927.
Walker-Daniels et al., "Overexpression of the EphA2 tyrosine kinase in prostate cancer", Prostate, 1999, 41(4):275-280.
Wallbrecher et al., "Exploration of the design principles of a cell-penetrating bicylic peptide scaffold," Bioconjug Chem., May 21, 2014, 25(5):955-964.
Wang et al., "Co-expression of MMP-14 and MMP-19 predicts poor survival in human glioma." Clinical and Translational Oncology, 2013, 15:139-145.
Wang et al., "MMP-14 overexpression correlates with poor prognosis in non-small cell lung cancer." Tumor Biology, 2014, 35:9815-9821.
Wang et al., "Probing for Integrin $\alpha v \beta 3$ Binding of RGD Peptides Using Fluorescence Polarization," Bioconjugate Chem., May-Jun. 2005, 16(3):729-734.
Wang, "An exact mathematical expression for describing competitive binding of two different ligands to a protein molecule." FEBS letters, 1995, 360(2):111-114.
Watanabe et al., "NK cell dysfunction with down-regulated CD16 and up-regulated molecules in patients with esophageal squamous cell carcinoma", Diseases of the Esophagus, 2010, 23(8):675-681.
Waterhouse et al., "Safety profile of nivolumab administered as 30-min infusion: analysis of data from CheckMate 153," Cancer Chemother Pharmacol., Apr. 2018, 81(4):679-686.
Watts, "TNF/TNFR family members in costimulation of T cell responses", Annu. Rev, Immunol., Apr. 2005, 23:23-68.

(56) References Cited

OTHER PUBLICATIONS

Weber, J. "Immune Checkpoint Proteins: A New Therapeutic Paradigm for Cancer—Background: CTLA-4 and PD-1 Blockade", Seminars in Oncology, Oct. 2010, 37(5):430-439.
Wei et al., "Discovery of Peptidomimetic Antibody—Drug Conjugate Linkers with Enhanced Protease Specificity," J. Med. Chem., 2018, 61(3):989-1000.
Wind et al., "Measuring carbonic anhydrase IX as a hypoxia biomarker: differences in concentrations in serum and plasma using a commercial enzyme-linked immunosorbent assay due to influences of metal ions," Annals of Clinical Biochemistry, Mar. 2011, 48(2):112-120.
Winter et al., "Making antibodies by phage display technology," Annual Review of Immunology, 1994, 12:433-455.
Wu et al., "Structures of the CXCR4 chemokine GPCR with small-molecule and cyclic peptide antagonists," Science, Nov. 2010, 330(6007):1066-1071.
Wu et al., "A novel polymorphism of FcgammaRIIIa (CD16) alters receptor function and predisposes to autoimmune disease", The Journal of Clinical Investigation, 1997, 100(5):1059-1070.
Wu et al., "Design and Characterization of Novel EphA2 Agonists for Targeted Delivery of Chemotherapy to Cancer Cells," Chem. Biol., 2015, 22(7):876-887.
Wu et al., "Natural killer cells in cancer biology and therapy", Molecular Cancer, Aug. 6, 2020, 19(1):120, 26 pages.
Wu et al., "Immunohistochemical localization of programmed death-1 ligand-1 (PD-L1) in gastric carcinoma and its clinical significance" Acta histochemica, 2006, 108(1):19-24.
Wykosky et al., "EphA2 as a novel molecular marker and target in glioblastoma multiforme", Molecular Cancer Research, Oct. 2005, 3(10):541-551.
Xiong et al., "Crystal structure of the extracellular segment of integrin αVβ3 in complex with an Arg-Gly-Asp Ligand", Science, Apr. 2002, 296(5565):151-155.
Yang et al., "Overexpression of EphA2, MMP-9, and MVD-CD34 in hepatocellular carcinoma: Implications for tumor progression and prognosis," Hepatol Res., 2009, 39(12):1169-1177.
Yardley et al., "EMERGE: a randomized phase II study of the antibody-drug conjugate glembatumumab vedotin in advanced glycoprotein NMB-expressing breast cancer." Journal of clinical oncology: official journal of the American Society of Clinical Oncology, 2015, 33(14):1609.
Yoon et al., "An efficient strategy for cell-based antibody library selection using an integrated vector system," BMC Biotechnology, 2012, 12(62):10 pages.
Yoshihara et al., "Tags for labeling protein N-termini with subtiligase for proteomics," Bioorganic & Medicinal Chemistry Letters, Nov. 2008, 18(22):6000-6003.
Yu and Taylor, "A new strategy applied to the synthesis of an a-helical bicyclic peptide constrained by two overlapping i, i+ 7 side-chain bridges of novel design." Tetrahedron letters, 1996, 37(11):1731-1734.
Yuan et al., "Neuropilin-1 and the development progress of the same as a therapeutic target for malignant tumors," Tumor, 2016, 36:358-364.
Yuan et al., "Over-expression of EphA2 and EphrinA-1 in human gastric adenocarcinoma and its prognostic value for postoperative patients," Dig Dis Sci., Nov. 2009, 54(11):2410-2417.
Zarrabi et al., "Inhibition of matrix metalloproteinase 14 (MMP-14)-mediated cancer cell migration." Journal of Biological Chemistry, 2011, 286(38):33167-33177.
Zelinski et al., "EphA2 Overexpression Causes Tumorigenesis of Mammary Epithelial Cells," Cancer research, Mar. 2001, 61(5):2301-2306.
Zervosen et al., "Development of New Drugs for an Old Target—The Penicillin Binding Proteins." Molecules. 2012:17 (11);12478-12505.
Zhang et al., "A new anti-HER2 antibody that enhances the antitumor efficacy of trastuzumab and pertuzumab with a distinct mechanism of action", Mol Immunol., 2020, 119:48-58.
Zhang et al., "FCGR2A and FCGR3A Polymorphisms Associated with Clinical Outcome of Epidermal Growth Factor Receptor-Expressing Metastatic Colorectal Cancer Patients Treated With Single-Agent Cetuximab", Journal of Clinical Oncology, 2007, 25(24):3712-3718.
Zhao et al., "Structural basis of specificity of a peptidyl urokinase inhibitor, upain-1," Journal of Structural Biology, Oct. 2007, 160(1):1-10.
Zhou et al., "Significance of semaphorin-3A and MMP-14 protein expression in non-small cell lung cancer", Oncology letters, 2014, 7(5):1395-1400.
Zhu et al., "High-affinity peptide against MT1-MMP for in vivo tumor imaging." Journal of controlled release, 2011, 150(3):248-255.
Zhuang et al., "Elevation of receptor tyrosine kinase EphA2 mediates resistance to trastuzumab therapy," Cancer Res., Jan. 1, 2010, 70(1):299-308.
Zilber et al., "CD38 expressed on human monocytes: a coaccessory molecule in the superantigeninduced proliferation," Proc Natl Acad Sci US A., Mar. 14, 2000, 97(6):2840-2845.
Zou et al., "PD-L1 (B7-H1) and PD-1 Pathway Blockade for Cancer Therapy: Mechanisms, Response Biomarkers and Combinations," Sci. Transl. Med., 2016, 8(328):328rv4., 1-14.
Zubiaur et al., "CD38 Ligation Results in Activation of the Raf-1/Mitogen-Activated Protein Kinase and the CD3-zeta/zeta-Associated Protein-70 Signaling Pathways in Jurkat T Lymphocytes," J Immunol., Jul. 1, 1997, 159(1):193-205.
Zupo et al., "CD38 signaling by agonistic monoclonal antibody prevents apoptosis of human germinal center B cells," Eur J Immunol., May 1994, 24(5):1218-1222.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2015/053247, dated May 11, 2017, 8 pages.
PCT International Preliminary Report on Patentability received for PCT/GB2018/050017, dated Jul. 18, 2019, 8 pages.
PCT International Preliminary Report on Patentability received for PCT/GB2018/052222, dated Feb. 13, 2020, 7 pages.
PCT International Preliminary Report on Patentability received for PCT/GB2019/050485, dated Sep. 3, 2020, 8 pages.
PCT International Preliminary Report on Patentability received for PCT/GB2019/053537, dated Jun. 24, 2021, 7 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/052058, dated Mar. 10, 2022, 8 pages.
PCT International Preliminary Report on Patentability received for PCT/GB2020/052590, dated Apr. 28, 2022, 7 pages.

(56) References Cited

OTHER PUBLICATIONS

PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2022/050043, dated Jul. 20, 2023, 13 pages.
PCT International Preliminary Report on Patentability received for PCT/EP2018/060498, dated Nov. 7, 2019. 8 Pages.
PCT International Preliminary Report on Patentability received for PCT/EP2019/065993, dated Dec. 30, 2020, 7 pages.
PCT International Preliminary Report on Patentability received for PCT/GB2017/053560, dated Jun. 6, 2019, 7 pages.
PCT International Preliminary Report on Patentability received for PCT/GB2018/051779, dated Jan. 9, 2020, 6 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053536, dated Jun. 24, 2021, 07 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.
PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022, 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052445, dated Apr. 14, 2022, 26 pages.
PCT International Preliminary Report on Patentability received for PCT/GB2020/052619, dated Apr. 28, 2022, 9 pages.
PCT International Preliminary Report on Patentability received for PCT/GB2020/053026, dated Jun. 9, 2022, 8 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Preliminary Report on Patentability received for PCT/GB2017/051250, dated Nov. 15, 2018, 7 pages.
PCT International Preliminary Report on Patentability received for PCT/GB2018/051118, dated Nov. 7, 2019, 11 pages.
PCT International Search Report and Written Opinion received for PCT/EP2017/083953, dated May 9, 2018, 9 pages.
PCT International Search Report and Written Opinion received for PCT/EP2017/083954, dated May 4, 2018, 9 pages.
PCT International Search Report and Written Opinion received for PCT/EP2018/060498, dated Jul. 5, 2018, 13 pages.
PCT International Search Report and Written Opinion received for PCT/EP2019/065993, dated Sep. 24, 2019, 11 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2019/066273, dated Sep. 27, 2019, 11 pages.
PCT International Search Report and Written Opinion received for PCT/EP2021/072866, dated Dec. 21, 2021, 21 pages.
PCT International Search Report and Written Opinion received for PCT/GB2015/053247, dated Jan. 27, 2016, 12 pages.
PCT International Search Report and Written Opinion received for PCT/GB2017/051250, dated Aug. 4, 2017, 10 pages.
PCT International Search Report and Written Opinion received for PCT/GB2017/053560, dated Jul. 2, 2018, 9 pages.
PCT International Search Report and Written Opinion received for PCT/GB2018/050017, dated Mar. 23, 2018, 12 pages.
PCT International Search Report and Written Opinion received for PCT/GB2018/051118, dated Aug. 3, 2018, 20 pages.
PCT International Search Report and Written Opinion received for PCT/GB2018/051779, dated Sep. 3, 2018, 10 pages.
PCT International Search Report and Written Opinion received for PCT/GB2018/053676, dated Mar. 21, 2019, 12 pages.
PCT International Search Report and Written Opinion received for PCT/GB2018/053678, dated Mar. 20, 2019, 12 pages.
PCT International Search Report and Written Opinion received for PCT/GB2019/050485, dated Jun. 4, 2019, 12 Pages.
PCT International Search Report and Written Opinion received for PCT/GB2019/050951, dated Jul. 4, 2019, 11 pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053080, dated Feb. 7, 2020, 19 pages.
PCT International Search Report and Written Opinion received for PCT/GB2019/053536, dated Mar. 11, 2020, 11 pages.
PCT International Search Report and Written Opinion received for PCT/GB2019/053537, dated Mar. 11, 2020, 10 pages.
PCT International Search Report and Written Opinion received for PCT/GB2019/053539, dated Mar. 11, 2020, 8 pages.
PCT International Search Report and Written Opinion received for PCT/GB2019/053540, dated Mar. 11, 2020, 10 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/050505, dated Apr. 28, 2020, 9 pages.
PCT International Search Report and Written Opinion received for PCT/GB2020/050874, dated Jun. 17, 2020, 15 pages.

(56) References Cited

OTHER PUBLICATIONS

PCT International Search Report and Written Opinion received for PCT/GB2020/051140, dated Aug. 20, 2020, 10 pages.
PCT International Search Report and Written Opinion received for PCT/GB2020/051144, dated Aug. 18, 2020, 12 pages.
PCT International Search Report and Written Opinion received for PCT/GB2020/051827, dated Nov. 3, 2020, 11 pages.
PCT International Search Report and Written Opinion received for PCT/GB2020/051829, dated Oct. 30, 2020, 11 pages.
PCT International Search Report and Written Opinion received for PCT/GB2020/051831, dated Nov. 4, 2020, 13 pages.
PCT International Search Report and Written Opinion received for PCT/GB2020/051923, dated Nov. 17, 2020, 12 pages.
PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/052619, dated Jan. 28, 2021, 12 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2021/051451, dated Sep. 22, 2021, 14 pages.
PCT International Search Report and Written Opinion received for PCT/GB2021/052001, dated Nov. 12, 2021, 11 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.
U.S. Appl. No. 18/313,983, filed May 8, 2023.
U.S. Appl. No. 18/345,506, filed Jun. 30, 2023.
Chen et al., "Peptide Ligands Stabilized by Small Molecules," Angewandte Chemie, vol. 53, No. 6, Feb. 2014 (pp. 1602-1606).
Heinis et al., "Phage-encoded combinatorial chemical libraries based on bicyclic peptides," Nature Chemical Biology 2009; 5(7): 502-507.
Loktev et al., "Multicyclic Peptides as Scaffold for the Development of Tumor Targeting Agents," Current Medicinal Chemistry, 2017, vol. 24, pp. 2141-2155.
Morrison, "Chemical Strategies for Bicyclic Peptide Formation," Univ. of Leeds, Sep. 2015, 160 Pages.
Mulder et al., "Scaffold Optimization in Discontinuous Epitope Containing Protein Mimics of gp120 Using Smart Libraries," Org. Biomol. Chem. 2013, vol. 11, pp. 2676-2684.
Pickens et al., "Practical Considerations, Challenges and Limitations of Bioconjugation via Azide-Alkyne Cycloaddition," Bioconjugate Chem., 2018, vol. 29, pp. 686-701.
Smeenk et al., "Reconstructing the Discontinuous and Confirmational ß1/3ß-Loop Binding Site on hFSH/hCG by Using Highly Constrained Multicyclic Peptides," ChemBioChem 2015, vol. 16, pp. 91-99.
International Search Report and Written Opinion issued by the European Patent Office as International Searching Authority for International Application No. PCT/GB2018/052222, mailed Oct. 11, 2018 (9 pages).
Dharmadhikari, et al., "CD137 and CD137L signals are main drivers of type 1, cell-mediated immune responses," Oncoimmunology 2016;5(4)1-8.
Forsberg, et al., "CD137 Plays Both Pathogenic and Protective Roles in Type 1 Diabetes Development in NOD Mice, "The Journal of Immunology 2017; 198(10):3857-3868.
Kamijo, et al., "Aberrant CD137 ligand expression induced by GATA6 overexpression promotes tumor progression in cutaneous T-cell lymphoma," American Socity of Hematology 2018;132(18):1922-1935.
Kang, et al., "Anti-CD137 Suppresses Tumor Growth by Blocking Reverse Signaling by CD137 Ligang," AACR Journals 2017;77(21)5989-6000.
Kim, et al., "Reverse signaling through the costimulatory ligand CD137L in epithelial cells is essential for natural killer cell-mediated acute tissue inflammation," PNAS 2012;109(1)E13-E22.
Mittler, el al., "Anti-CD137 Antibodies in the Treatment of Autoimmune Disease and Cancer," Immunologic Research 2004;29/1-3:197-208.
Shao, et al., "CD137 ligand, a member of the tumor necrosis factor family, regulates immune responses via reverse signal transduction," Journal of Leukocyte Biology 2011:89:21-29.
Soderstrom, et al., "CD137: A checkpoint regulator involved in atherosclerosis," Atherosclerosis 2018;272:66-72.
Michel, et al., "Expression of Soluble CD137 Correlates with Activation-Induced Cell Death of Lymphocytes," Cytokine 2000;12(6):742-746.
Rajendran, et al., "CD137 signaling in Hodgkin and Reed-Sternberg cell lines induces IL-13 secretion, immune deviation and enhanced growth," Oncoimmunology. 2016;5(6).
Palma, et al., "CD137 and CD137 Ligand Constitutively Coexpressed on Human T and B Leukemia Cells Signal Proliferation and Survival," Int. J. Cancer. 2004;180:390-398.
Ho, et al., "Expression of CD137 on Hodgkin and Reed-Sternberg Cells Inhibits T-cell Activation by Eliminating CD137 Ligand Expression," Cancer Res. 2013;73(2):652-661.

* cited by examiner

BICYCLIC PEPTIDE LIGANDS SPECIFIC FOR CD137

CROSS-REFERENCE TO RELATED APPLICATIONS

This application is a divisional of prior U.S. patent application Ser. No. 16/636,105, filed Feb. 3, 2020 (now U.S. Pat. No. 11,261,214 B2), which is a U.S. national stage application under 35 U.S.C. § 371 of International Application No. PCT/GB2018/052222, filed Aug. 3, 2018, which claims priority to United Kingdom Application No. GB1805850.3, filed Apr. 9, 2018, United Kingdom Application No. GB1802934.8, filed Feb. 23, 2018, and United Kingdom Application No. GB1712589.9, filed Aug. 4, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 20, 2022, is named 392664_045US1_188625_Sequence_Listing.txt and is 89,159 bytes in size.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred-square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J Med Chem 41 (11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a peptide ligand specific for CD137 comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder mediated by CD137.

DETAILED DESCRIPTION OF THE INVENTION

Figure 1:
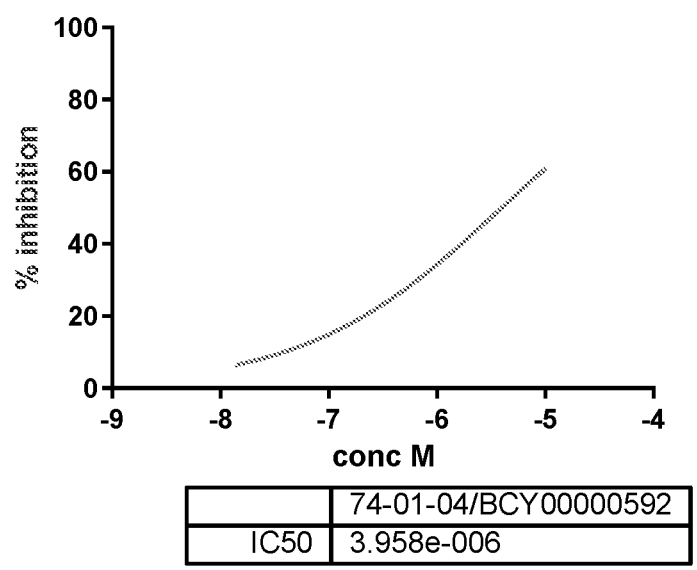
FIG. 1: Results of CD137 cell activity assay using bicyclic peptide BCY592.

According to one particular aspect of the invention which may be mentioned, there is provided a peptide ligand specific for CD137 comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

In one embodiment, said loop sequences comprise 5 or 6 amino acid acids.

In a further embodiment, said peptide ligand comprises three cysteine residues separated by two loop sequences both of which consist of 6 amino acids.

In a further embodiment, said peptide ligand comprises three cysteine residues separated by two loop sequences one of which consists of 5 amino acids and the other of which consists of 6 amino acids.

In one embodiment, said peptide ligand comprises an amino acid sequence selected from:

$$C_i\text{-I-E-E-G-Q-Y-}C_{ii}\text{-}X_1\text{-}X_2\text{-D-}X_3\text{-Y/Q/M-}X_4\text{-}C_{iii};$$ (SEQ ID NO: 20)

$$C_i\text{-D-I-G-P-P-Y-}C_{ii}\text{-Y-R/A-D-M/P-Y-M-}C_{iii};$$ (SEQ ID NO: 21)

$$C_i\text{-D-E-W-G-L-F/Y-C-I/F-P/A-H-S/P-D-}C_{iii};$$ (SEQ ID NO: 22)
and $$C_i\text{IEPGPFC}_{ii}\text{YADPYMC}_{iii};$$ (SEQ ID NO: 19)

wherein $X_1$-$X_4$ represent any amino acid residue and $C_i$, $C_{ii}$ and $C_{iii}$ represent first, second and third cysteine residues, respectively or a pharmaceutically acceptable salt thereof.

An Alanine scanning experiment was conducted on selected peptides of the invention. An Alanine scan is used to predict which amino acids positions are most amenable to substitutions and further optimisation of affinity and/or other desirable properties. The Alanine scan peptides were characterized into three categories based on affinity relative to the parental peptide sequence (BCY7151; SEQ ID NO: 92): 1. no loss in affinity 2. 2-10 fold weaker affinity and 3. >10 fold weaker affinity. Peptides in category 1 and category 2 can undergo extensive SAR testing with alternative amino acid substitutions. The peptides in category 3 were kept fixed or only substituted with highly similar amino acids. The results of the Alanine scan are shown in Table 2 wherein it can be seen that the Aspartic Acid (D) amino acid residue at position 9 is most important for binding because replacement of this amino acid residue with an Alanine residue eliminated binding activity.

A D-Alanine scanning experiment was also conducted on selected peptides of the invention. The default preparation of all bicyclic peptides is in the L-configuration, therefore, the D-Alanine scan shows which amino acid positions are amenable to D-amino acid substitutions. The results of the D-Alanine scan are shown in Table 2 wherein it can be seen that replacing the position 4 Glycine (G) with D-Ala improved affinity relative to the reference peptide. This implies that the D-Ala4 peptide (BCY7297; SEQ ID NO: 106) is important, since it provides improved affinity as well as other advantages associated with non-natural D isomer amino acids.

In one embodiment, said peptide ligand comprises three cysteine residues separated by two loop sequences both of which consist of 6 amino acids, and said peptide ligand comprises an amino acid sequence selected from:

$$C_i\text{-I-E-E-G-Q-Y-}C_{ii}\text{-}X_1\text{-}X_2\text{-D-}X_3\text{-Y/Q/M-}X_4\text{-}C_{iii};$$ (SEQ ID NO: 20)

$$C_i\text{-D-I-G-P-P-Y-}C_{ii}\text{-Y-R/A-D-M/P-Y-M-}C_{iii};$$ (SEQ ID NO: 21)
and $$C_i\text{IEPGPFC}_{ii}\text{YADPYMC}_{iii};$$ (SEQ ID NO: 19)

wherein $X_1$-$X_4$ represent any amino acid residue and $C_i$, $C_{ii}$ and $C_{iii}$ represent first, second and third cysteine residues, respectively or a pharmaceutically acceptable salt thereof.

In one embodiment, $X_1$ is selected from Y, F and H.
In one embodiment, $X_2$ is selected from R, A and S.
In one embodiment, $X_3$ is selected from M, P and H.
In one embodiment, $X_4$ is selected from M, Y, L and F.

In one embodiment, said peptide ligand comprises three cysteine residues separated by two loop sequences the first of which consists of 6 amino acids and the second of which consists of 5 amino acids, and said peptide ligand comprises an amino acid sequence which is:

$$C_i\text{-D-E-W-G-L-F/Y-}C_{ii}\text{-I/F-P/A-H-S/P-D-}C_{iii};$$ (SEQ ID NO: 22)

wherein $C_i$, $C_{ii}$ and $C_{iii}$ represent first, second and third cysteine residues, respectively or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q/M-$X_4$-$C_{iii}$ (SEQ ID NO: 20) comprises an amino acid sequence selected from any one of SEQ ID NOS: 1-14:

$$C_i\text{IEEGQYC}_{ii}\text{YRDMYMC}_{iii};$$ (SEQ ID NO: 1)

$$C_i\text{IEEGQYC}_{ii}\text{YADPYMC}_{iii};$$ (SEQ ID NO: 2)

$$C_i\text{IEEGQYC}_{ii}\text{YADPYYC}_{iii};$$ (SEQ ID NO: 3)

$$C_i\text{IEEGQYC}_{ii}\text{YSDPYYC}_{iii};$$ (SEQ ID NO: 4)

$$C_i\text{IEEGQYC}_{ii}\text{FADPYMC}_{iii};$$ (SEQ ID NO: 5)

$$C_i\text{IEEGQYC}_{ii}\text{YADHQLC}_{iii};$$ (SEQ ID NO: 6)

$$C_i\text{IEEGQYC}_{ii}\text{HADPYYC}_{iii};$$ (SEQ ID NO: 7)

$$C_i\text{IEEGQYC}_{ii}\text{HADPYFC}_{iii};$$ (SEQ ID NO: 8)

$$C_i\text{IEEGQYC}_{ii}\text{YADHYMC}_{iii};$$ (SEQ ID NO: 9)

$$C_i\text{IEEGQYC}_{ii}\text{YADPYLC}_{iii};$$ (SEQ ID NO: 10)

$$C_i\text{IEEGQYC}_{ii}\text{YSDPYLC}_{iii};$$ (SEQ ID NO: 11)

-continued $C_i$IEEGQYC$_{ii}$FADPYLC$_{iii}$; (SEQ ID NO: 12)

$C_i$IEEGQYC$_{ii}$HADPYMC$_{iii}$; (SEQ ID NO: 13)
and $C_i$IEEGQYC$_{ii}$HADPQMC$_{iii}$; (SEQ ID NO: 14)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-I-E-E-G-Q-Y-C$_{ii}$-X$_1$-X$_2$-D-X$_3$-Y/Q/M-X$_4$-C$_{iii}$ (SEQ ID NO: 20) comprises an amino acid sequence selected from:
- A-(SEQ ID NO: 1)-A (herein referred to as 74-01-00-N004);
- A-(SEQ ID NO: 2)-A (herein referred to as 74-01-01-N001);
- A-(SEQ ID NO: 3)-A (herein referred to as 74-01-02-N001);
- A-(SEQ ID NO: 4)-A (herein referred to as 74-01-03-N001);
- A-(SEQ ID NO: 5)-A (herein referred to as 74-01-04-N001);
- A-(SEQ ID NO: 6)-A (herein referred to as 74-01-05-N001);
- A-(SEQ ID NO: 7)-A (herein referred to as 74-01-06-N001);
- A-(SEQ ID NO: 8)-A (herein referred to as 74-01-07-N001);
- A-(SEQ ID NO: 9)-A (herein referred to as 74-01-08-N001);
- A-(SEQ ID NO: 10)-A (herein referred to as 74-01-09-N001);
- A-(SEQ ID NO: 10)-SVG (herein referred to as 74-01-09-T03-N002);
- A-(SEQ ID NO: 11)-A (herein referred to as 74-01-10-N001);
- A-(SEQ ID NO: 12)-A (herein referred to as 74-01-11-N001);
- A-(SEQ ID NO: 13)-A (herein referred to as 74-01-13-N001); and
- A-(SEQ ID NO: 14)-A (herein referred to as 74-01-14-N001).

In a further embodiment, the peptide ligand of $C_i$-D-I-G-P-P-Y-C$_{ii}$-Y-R/A-D-M/P-Y-M-C$_{iii}$ (SEQ ID NO: 21) comprises an amino acid sequence selected from:

$C_i$DIGPPYC$_{ii}$YRDMYMC$_{iii}$; (SEQ ID NO: 15)
and $C_i$DIGPPYC$_{ii}$YADPYMC$_{iii}$; (SEQ ID NO: 16)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-I-G-P-P-Y-C$_{ii}$-Y-R/A-D-M/P-Y-M-C$_{iii}$ (SEQ ID NO: 21) comprises an amino acid sequence selected from:
- A-(SEQ ID NO: 15)-A (herein referred to as 74-01-16-N001); and
- A-(SEQ ID NO: 16)-A (herein referred to as 74-01-17-N001).

In a further embodiment, the peptide ligand of $C_i$-D-E-W-G-L-F/Y-C$_{ii}$-I/F-P/A-H-S/P-D-C$_{iii}$ (SEQ ID NO: 22) comprises an amino acid sequence selected from:

$C_i$DEWGLFC$_{ii}$IPHSDC$_{iii}$; (SEQ ID NO: 17)
and $C_i$DEWGLYC$_{ii}$FAHPDC$_{iii}$; (SEQ ID NO: 18)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-E-W-G-L-F/Y-C$_{ii}$-I/F-P/A-H-S/P-D-C$_{iii}$ (SEQ ID NO: 22) comprises an amino acid sequence selected from:
- Ac-A-(SEQ ID NO: 17)-A (herein referred to as 74-02-00-N004); and
- A-(SEQ ID NO: 18)-A (herein referred to as 74-02-01-N001).

In one embodiment, the peptide ligand of $C_i$IEPGPFC$_{ii}$YADPYMC$_{iii}$ (SEQ ID NO: 19) comprises an amino acid sequence of:
- A-(SEQ ID NO: 19)-NRV (herein referred to as 74-19-00-T01-N002).

In one embodiment, the molecular scaffold is selected from 1,1',1''-(1,3,5-triazinane-1,3,5-triyl)triprop-2-en-1-one (TATA) and the peptide ligand comprises an amino acid sequence selected from:
- A-(SEQ ID NO: 1)-A (herein referred to as 74-01-00-N004);
- A-(SEQ ID NO: 2)-A (herein referred to as 74-01-01-N001);
- A-(SEQ ID NO: 3)-A (herein referred to as 74-01-02-N001);
- A-(SEQ ID NO: 4)-A (herein referred to as 74-01-03-N001);
- A-(SEQ ID NO: 5)-A (herein referred to as 74-01-04-N001);
- A-(SEQ ID NO: 6)-A (herein referred to as 74-01-05-N001);
- A-(SEQ ID NO: 7)-A (herein referred to as 74-01-06-N001);
- A-(SEQ ID NO: 8)-A (herein referred to as 74-01-07-N001);
- A-(SEQ ID NO: 9)-A (herein referred to as 74-01-08-N001);
- A-(SEQ ID NO: 10)-A (herein referred to as 74-01-09-N001);
- A-(SEQ ID NO: 10)-SVG (herein referred to as 74-01-09-T03-N002);
- A-(SEQ ID NO: 11)-A (herein referred to as 74-01-10-N001);
- A-(SEQ ID NO: 12)-A (herein referred to as 74-01-11-N001);
- A-(SEQ ID NO: 13)-A (herein referred to as 74-01-13-N001);
- A-(SEQ ID NO: 14)-A (herein referred to as 74-01-14-N001);
- A-(SEQ ID NO: 15)-A (herein referred to as 74-01-16-N001);
- A-(SEQ ID NO: 16)-A (herein referred to as 74-01-17-N001);
- Ac-A-(SEQ ID NO: 17)-A (herein referred to as 74-02-00-N004); and A-(SEQ ID NO: 18)-A (herein referred to as 74-02-01-N001).

The scaffold/peptide ligands of this embodiment demonstrated superior CD137 competition binding as shown herein in Table 1.

In a yet further embodiment, said peptide ligand is selected from:

$C_i$IEEGQYC$_{ii}$FADPY(Nle)C$_{iii}$; (SEQ ID NO: 23)

$C_i$IKEGQYC$_{ii}$FADPY(Nle)C$_{iii}$; (SEQ ID NO: 24)

$C_i$IEKGQYC$_{ii}$FADPY(Nle)C$_{iii}$; (SEQ ID NO: 25)

$C_i$IEE(D-K)QYC$_{ii}$FADPY(Nle)C$_{iii}$; (SEQ ID NO: 26)

$C_i$IEEGKYC$_{ii}$FADPY(Nle)C$_{iii}$; (SEQ ID NO: 27)

$C_i$IEEGQYC$_{ii}$KADPY(Nle)C$_{iii}$; (SEQ ID NO: 28)

$C_i$IEEGQYC$_{ii}$FADKY(Nle)C$_{iii}$; and (SEQ ID NO: 29)

$C_i$IEEGQYC$_{ii}$FADPYKC$_{iii}$; (SEQ ID NO: 30)

wherein $C_i$, $C_{ii}$ and $C_{iii}$ represent first, second and third cysteine residues, respectively or a pharmaceutically acceptable salt thereof.

In a yet further embodiment, said peptide ligand comprises N and C terminal modifications and comprises an amino acid sequence selected from:

A-$C_i$IEEGQYC$_{ii}$FADPY(Nle)C$_{iii}$-A; (SEQ ID NO: 31; BCY3814)

Ac-A-$C_i$IEEGQYC$_{ii}$FADPY(Nle)C$_{iii}$-Dap; (SEQ ID NO: 32; BCY7732)

Ac-A-$C_i$IKEGQYC$_{ii}$FADPY(Nle)C$_{iii}$-A; (SEQ ID NO: 33; BCY7733)

Ac-A-$C_i$IEKGQYC$_{ii}$FADPY(Nle)C$_{iii}$-A; (SEQ ID NO: 34; BCY7734)

Ac-A-$C_i$IEE(D-K)QYC$_{ii}$FADPY(Nle)C$_{iii}$-A; (SEQ ID NO: 35; BCY7735)

Ac-A-$C_i$IEEGKYC$_{ii}$FADPY(Nle)C$_{iii}$-A; (SEQ ID NO: 36; BCY7736)

Ac-A-$C_i$IEEGQYC$_{ii}$KADPY(Nle)C$_{iii}$-A; (SEQ ID NO: 37; BCY7737)

Ac-A-$C_i$IEEGQYC$_{ii}$FADKY(Nle)C$_{iii}$-A; and (SEQ ID NO: 38; BCY7738)

Ac-A-$C_i$IEEGQYC$_{ii}$FADPYKC$_{iii}$-A; (SEQ ID NO: 39; BCY7739)

wherein $C_i$, $C_{ii}$ and $C_{iii}$ represent first, second and third cysteine residues, respectively, Ac represents an N-terminal acetyl group and Dap represents diaminopropionic acid or a pharmaceutically acceptable salt thereof.

In an alternative embodiment, said peptide ligand comprises an amino acid sequence which is:

$C_i$LPPGQYC$_{ii}$FPDLLLC$_{iii}$ (SEQ ID NO: 40; 74-22-00)

wherein $C_i$, $C_{ii}$ and $C_{iii}$ represent first, second and third cysteine residues, respectively.

In an alternative embodiment, said peptide ligand comprises three cysteine residues separated by two loop sequences both of which consist of 6 amino acids, and said peptide ligand comprises an amino acid sequence which is:

$C_i$-I/L/M/V-E/D/P/S-P/E/A-G-P/Q-Y/F-$C_{ii}$-Y-A-D-P-Y/M-M/L/Y-$C_{iii}$; (SEQ ID NO: 41)

wherein $C_i$, $C_{ii}$ and $C_{iii}$ represent first, second and third cysteine residues, respectively.

In a further embodiment, said amino acid sequence is selected from the peptide sequences listed in Table 1. In a yet further embodiment, said amino acid sequence is selected from the peptide sequences listed in Table 1 excluding the peptides of BCY7238, BCY7241, BCY7243 and BCY7246. The peptides of this embodiment were tested in the CD137 direct binding assay and demonstrated good levels of binding.

In a further embodiment, said amino acid sequence is selected from the peptide sequences listed in Table 3. The peptides of this embodiment were tested in the CD137 direct binding assay and demonstrated good levels of binding.

In a further embodiment, said amino acid sequence is selected from the peptide sequences listed in Tables 4 and 5. The peptides of this embodiment were tested in the CD137 SPR assay and demonstrated good levels of binding.

In a further embodiment, said amino acid sequence is selected from BCY592. Data is presented herein in FIG. 1 which shows that the bicyclic peptide BCY592 inhibited CD137L activity in a cell-based assay.

In an alternative embodiment, said peptide ligand comprises three cysteine residues separated by two loop sequences both of which consist of 6 amino acids, and said peptide ligand comprises an amino acid sequence which is:

$C_i$-$X_5$-$X_6$-$X_7$-$X_8$-$X_9$-$X_{10}$-$C_{ii}$-$X_{11}$-$X_{12}$-D-$X_{13}$-$X_{14}$-$X_{15}$-$C_{iii}$; (SEQ ID NO: 266)

wherein $C_i$, $C_{ii}$ and $C_{iii}$ represent first, second and third cysteine residues, respectively;

$X_5$ represents Ile, tBuAla or Chg;

$X_6$ represents Glu, Pro, Asp, Lys, Aad, HyP or Oxa;

$X_7$ represents Glu, Lys or Aad;

$X_8$ represents Gly, D-Lys, D-Ala, L-Ala, D-Phe, D-Glu, D-Gln, D-Leu, D-Ser or D-Trp;

$X_9$ represents Gln, Lys, Ala, Pro, 5,5-dmP, Oic, Oxa, HyP, Aib or Ac5c;

$X_{10}$ represents Tyr, Phe, 3MePhe, 4MePhe, 4FPhe, 2Nal, 4MeOPhe or 4,4-BPA;

$X_{11}$ represents Phe, Lys, 4MePhe, 2FPhe, 4FPhe, 4Pal, 4,4-BPA, 4tBuPhe, NO2Phe or 4BrPhe;

$X_{12}$ represents Ala or Lys;

$X_{13}$ represents Pro or Lys;

$X_{14}$ represents Tyr or Lys; and $X_{15}$ represents Met, Lys, Nle, HLeu or Ahp.

In one embodiment, the peptide ligand of SEQ ID NO: 266 is selected from the $C_i$ to $C_{ii}$ sequences of the following peptides (i.e. absent any N-terminal and C-terminal additions): BCY7239, BCY7240, BCY7242, BCY7244, BCY7245, BCY7247, BCY7248, BCY7249, BCY7416, BCY7287, BCY7297, BCY7154, BCY7156, BCY7157, BCY7158, BCY7162, BCY7165, BCY7166, BCY7167, BCY7168, BCY7169, BCY7170, BCY7174, BCY7175, BCY7177, BCY7178, BCY7179, BCY7183, BCY7185, BCY7195, BCY7198, BCY7211, BCY7311, BCY7768, BCY7770, BCY7772, BCY7773, BCY7774, BCY7775, BCY7776, BCY7796, BCY7798, BCY7801, BCY7802, BCY7936, BCY7941, BCY7942, BCY7944, BCY7950, BCY7954, BCY7958, BCY7959, BCY7960, BCY7952, BCY7961, BCY8656, BCY8659, BCY8663, BCY8668, BCY8669, BCY8674, BCY8675, BCY9273, BCY3814, BCY7527 and BCY7965.

In a further embodiment, the peptide ligand of SEQ ID NO: 266 is selected from the full sequences of the following peptides (i.e. including all N-terminal and C-terminal additions): BCY7239, BCY7240, BCY7242, BCY7244, BCY7245, BCY7247, BCY7248, BCY7249, BCY7416, BCY7287, BCY7297, BCY7154, BCY7156, BCY7157, BCY7158, BCY7162, BCY7165, BCY7166, BCY7167, BCY7168, BCY7169, BCY7170, BCY7174, BCY7175, BCY7177, BCY7178, BCY7179, BCY7183, BCY7185, BCY7195, BCY7198, BCY7211, BCY7311, BCY7768, BCY7770, BCY7772, BCY7773, BCY7774, BCY7775, BCY7776, BCY7796, BCY7798, BCY7801, BCY7802, BCY7936, BCY7941, BCY7942, BCY7944, BCY7950, BCY7954, BCY7958, BCY7959, BCY7960, BCY7952, BCY7961, BCY8656, BCY8659, BCY8663, BCY8668, BCY8669, BCY8674, BCY8675, BCY9273, BCY3814, BCY7527 and BCY7965.

These peptides either all demonstrated good levels of binding in the direct binding or SPR assays described herein or represented peptides which are tolerant of substitution with a Lys residue.

In one embodiment, $X_5$ represents Ile or tBuAla.
In one embodiment, $X_6$ represents Lys, Glu or Pro.
In one embodiment, $X_7$ represents Glu or D-Lys.
In one embodiment, $X_8$ represents Gly, D-Lys, D-Phe or D-Ala.
In one embodiment, $X_9$ represents Gln, Lys or Pro.
In one embodiment, $X_{10}$ represents Tyr or 4MePhe.
In one embodiment, $X_{11}$ represents Phe or 4FPhe.
In one embodiment, $X_{12}$ represents Ala.
In one embodiment, $X_{13}$ represents Pro.
In one embodiment, $X_{14}$ represents Tyr.
In one embodiment, $X_{15}$ represents Met or Nle.

In a further embodiment, said peptide ligand comprises three cysteine residues separated by two loop sequences both of which consist of 6 amino acids, and said peptide ligand comprises an amino acid sequence which is:

(SEQ ID NO: 267)
$C_i$-$X_5$-$X_6$-$X_7$-$X_8$-$X_9$-$X_{10}$-$C_{ii}$-$X_{11}$-A-D-P-Y-$X_{15}$-$C_{iii}$;

wherein $C_i$, $C_{ii}$ and $C_{iii}$ represent first, second and third cysteine residues, respectively;
$X_5$ represents Ile or tBuAla;
$X_6$ represents Lys, Glu or Pro;
$X_7$ represents Glu or D-Lys;
$X_8$ represents Gly, D-Lys, D-Phe or D-Ala;
$X_9$ represents Gln, Lys or Pro;
$X_{10}$ represents Tyr or 4MePhe;
$X_{11}$ represents Phe or 4FPhe; and
$X_{15}$ represents Met or Nle.

In one embodiment, the peptide ligand of SEQ ID NO: 267 is selected from the $C_i$ to $C_{ii}$ sequences of the following peptides (i.e. absent any N-terminal and C-terminal additions): BCY7239, BCY7240, BCY7242, BCY7416, BCY7156, BCY7166, BCY7174, BCY7774, BCY9273, BCY3814, BCY7527 and BCY7965.

In a further embodiment, the peptide ligand of SEQ ID NO: 267 is selected from the full sequences of the following peptides (i.e. including all N-terminal and C-terminal additions): BCY7239, BCY7240, BCY7242, BCY7416, BCY7156, BCY7166, BCY7174, BCY7774, BCY9273, BCY3814, BCY7527 and BCY7965.

These peptides either all demonstrated excellent levels of binding in the direct binding or SPR assays described herein or represented peptides which are tolerant of substitution with a Lys residue.

In one embodiment, the peptide ligand of SEQ ID NO: 267 is selected from the $C_i$ to $C_{ii}$ sequences of the following peptides (i.e. absent any N-terminal and C-terminal additions): BCY7239, BCY7240, BCY7242 and BCY7416.

In a further embodiment, the peptide ligand of SEQ ID NO: 267 is selected from the full sequences of the following peptides (i.e. including all N-terminal and C-terminal additions): BCY7239, BCY7240, BCY7242 and BCY7416.

These peptides represented peptides which are tolerant of substitution with a Lys residue.

In one embodiment, the peptide ligand of SEQ ID NO: 267 is selected from the $C_i$ to $C_{ii}$ sequences of the following peptides (i.e. absent any N-terminal and C-terminal additions): BCY9273, BCY3814, BCY7527 and BCY7965.

In a further embodiment, the peptide ligand of SEQ ID NO: 267 is selected from the full sequences of the following peptides (i.e. including all N-terminal and C-terminal additions): BCY9273, BCY3814, BCY7527 and BCY7965.

These peptides either all demonstrated good levels of binding in the direct binding or SPR assays described herein.

In one embodiment, the peptide ligand of SEQ ID NO: 267 is selected from the $C_i$ to $C_{ii}$ sequences of the following peptides (i.e. absent any N-terminal and C-terminal additions): BCY7156, BCY7166, BCY7174 and BCY7774.

In a further embodiment, the peptide ligand of SEQ ID NO: 267 is selected from the full sequences of the following peptides (i.e. including all N-terminal and C-terminal additions): BCY7156, BCY7166, BCY7174 and BCY7774.

These peptides either all demonstrated excellent levels of binding in the direct binding or SPR assays described herein.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

Nomenclature

Numbering

When referring to amino acid residue positions within compounds of formula (I), cysteine residues ($C_i$, $C_{ii}$ and $C_{iii}$) are omitted from the numbering as they are invariant, therefore, the numbering of amino acid residues within the compound of formula (I) is referred to as below:

(SEQ ID NO: 1)
-C$_i$-I$_1$-E$_2$-E$_3$-G$_4$-Q$_5$-Y$_6$-C$_{ii}$-Y$_7$-R$_8$-D$_9$-M$_{10}$-Y$_{11}$-M$_{12}$-C$_{iii}$-

For the purpose of this description, all bicyclic peptides are assumed to be cyclised with TBMB (1,3,5-tris(bromomethyl)benzene) or 1,1',1''-(1,3,5-triazinane-1,3,5-triyl)triprop-2-en-1-one (TATA) and yielding a tri-substituted structure. Cyclisation with TBMB and TATA occurs on C$_i$, C$_{ii}$ and C$_{iii}$ Molecular Format N- or C-terminal extensions to the bicycle core sequence are added to the left or right side of the sequence, separated by a hyphen. For example, an N-terminal βAla-Sar10-Ala tail would be denoted as:

(SEQ ID NO: X)
βAla-Sar10-A-

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as C$_i$, C$_{ii}$ and C$_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Selectivity. Certain peptide ligands of the invention demonstrate good selectivity over other CDs.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of formula (I) contain an amine function, these may form quaternary ammonium salts, for example by reaction with an alkylating agent according to methods well known to the skilled person. Such quaternary ammonium compounds are within the scope of formula (I).

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{ii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Ca-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons. (for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulphur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the CD137 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-triacryloylhexahydro-1,3,5-triazine (TATA), or a derivative thereof.

In one embodiment, the molecular scaffold is 2,4,6-tris (bromomethyl)mesitylene. This molecule is similar to 1,3,5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl) amine, tris-(2-maleimidoethyl)benzene, tris-(maleimido) benzene. An example of an αβ unsaturated carbonyl containing compound is 1,1',1"-(1,3,5-triazinane-1,3,5-triyl) triprop-2-en-1-one (TATA) (Angewandte Chemie, International Edition (2014), 53(6), 1602-1606). An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Reactive Groups

The molecular scaffold of the invention may be bonded (i.e. covalently) to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Details may be found in WO 2009/098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

In one embodiment, the reactive group comprises a cysteine residue. In an alternative embodiment, the reactive group comprises penicillamine.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved. In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO 2009/098450 or Heinis, et al., *Nat Chem Biol* 2009, 5 (7), 502-7.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

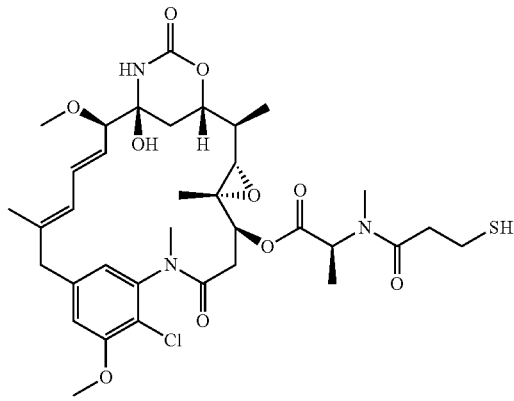

Monomethyl auristatin E (MMAE) is a synthetic antineoplastic agent and has the following structure:

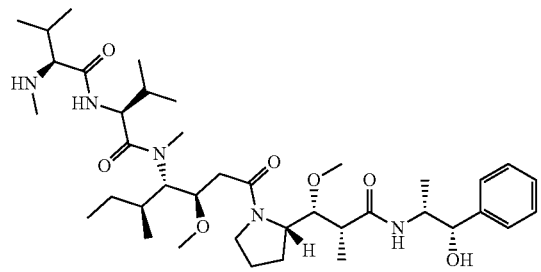 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In one yet further particular embodiment of the invention, the cytotoxic agent is selected from maytansinoids (such as DM1).

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the cytotoxic agent and linker is selected from any combinations of those described in WO 2016/067035 (the cytotoxic agents and linkers thereof are herein incorporated by reference).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide—linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used.

For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as CD137 binding agents.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et al., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder mediated by CD137.

According to a further aspect of the invention, there is provided a method of preventing, suppressing or treating a disease or disorder mediated by CD137, which comprises administering to a patient in need thereof an effector group and drug conjugate of the peptide ligand as defined herein.

In one embodiment, the CD137 is mammalian CD137. In a further embodiment, the mammalian CD137 is human CD137 (hCD137).

In one embodiment, the disease or disorder mediated by CD137 is selected from cancer, infection and inflammation. In a further embodiment, the disorder or disease mediated by CD137 is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the oesophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukaemias, lymphomas) and premalignant haematological disorders and disorders of borderline malignancy including haematological malignancies and related conditions of lymphoid lineage (for example acute lymphocytic leukaemia [ALL], chronic lymphocytic leukaemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukaemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukaemia (B-CLL), B and T acute lymphocytic leukaemia (ALL), T cell lymphoma (TCL), acute myeloid leukaemia (AML), hairy cell leukaemia (HCL), Hodgkin's Lymphoma (HL), and chronic myeloid leukaemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

Examples

Materials and Methods
Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-triacryloylhexahydro-1,3,5-triazine (TATA, Sigma). For this, linear peptide was diluted with 50:50 MeCN:H$_2$O up to ~35 mL, ~500 μL of 100 mM TATA in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI). Once completed, 1 ml of 1M L-cysteine hydrochloride monohydrate (Sigma) in H$_2$O was added to the reaction for ~60 min at RT to quench any excess TATA.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

In some cases, peptides are converted to activated disulphides prior to coupling with the free thiol group of a toxin using the following method; a solution of 4-methyl(succinimidyl 4-(2-pyridylthio)pentanoate) (100 mM) in dry DMSO (1.25 mol equiv) was added to a solution of peptide (20 mM) in dry DMSO (1 mol equiv). The reaction was well mixed and DIPEA (20 mol equiv) was added. The reaction was monitored by LC/MS until complete.

Abbreviations

Aad 2-Aminoadipic acid
Abu 2-Aminobutyric acid
Ac5c Aminocyclopentanecarboxylic acid
Ahp Aminoheptanoic acid
Aib aminoisobutyric acid
Me-Ala methyl alanine
NMe-Ala N-methyl alanine
tBuAla t-butyl-Alanine
Api Amino pimelic acid
Aze Azetidine
4,4-BPA 4,4-Biphenylalanine
CF3G Trifluoromethyl-Alanine
Cha 3-cyclohexyl alanine
Chg L-Cyclohexyl glycine
Cit citrulline
H-Cys homocysteine
Dap diaminopimelic acid
Fl fluorescein
NMeGlu N-methyl glutamic acid
HGln homoglutamine
HyP hydroxyproline
Hleu homoleucine
Nle norleucine Nal naphthylalanine
NMeIle N-Methyl-lsoleucine
Oic octahydroindolecarboxylic acid
Oxa oxazolidine-4-carboxylic acid
Pal pyridylalanine
Pen penicillamine
pCaPhe para-Carbamoyl-Phenylalanine
pCoPhe para-Carboxy-Phenylalanine
Phg phenylglycine
HPhe homophenylalanine
FPhe fluorophenylalanine
MePhe methyl phenylalanine
MeOPhe methoxy phenylalanine
tBuPhe t-butyl phenylalanine
NO2Phe nitro phenylalanine
BrPhe bromo phenylalanine
Pip Pipecolic acid
5,5-dmP 5,5-Dimethyl-L-Proline
Sar sarcosine
HSe(me) Homoserine(Me)
TetraZ tetrazole alanine
NMeTyr N-methyl tyrosine
Biological Data
1. CD137 Direct Binding Assay
Affinity of the peptides of the invention for human CD137 (Ki) was determined using a fluorescence polarisation assay, in accordance with the methods disclosed in WO 2016/067035. Peptides of the invention were labelled with a fluorescent tag (fluorescein, Fl) and diluted to 2.5 nM in 50 mM HEPES with 100 mM NaCl and 0.05% tween pH 7.5. CD137 protein was titrated starting at 3 µM in the same assay buffer as the peptide to assay 1 nM peptide in a total volume of 25 µL in black walled and bottomed low bind low volume 384 well plates. The assay was typically set up by adding 5 µL assay buffer, 10 µL CD137 protein then 10 µL fluorescent peptide. The concentrations of CD137 protein were 1 in 2 serial dilutions to give 12 different concentrations starting at 3 µM. Measurements were conducted on a BMG PHERAstar FS equipped with an FP 485 520 520 optic module at 25° C. with 200 flashes per well and a positioning delay of 0.1 second. Alternatively, the measurements were performed using Envision (PerkinElmer) equipped with FITC FP Dual Enh mirror, set to 30 flashes. Each well was measured every 5 minutes for 60 minutes. The gain used for analysis was determined for each tracer at the end of the 60 minutes where there was no protein in the well. The mP were fit to a standard 1:1 binding model with a quadratic equation to generate a Kd value. Selected peptides of the invention were tested in the above mentioned assay and the results are shown in Tables 1 to 3:

TABLE 1

Direct Binding Results with Selected Peptides

| Peptide Number | SEQ ID NO: | Peptide Reference | Sequence | Kd nM |
|---|---|---|---|---|
| BCY633 | 42 | (B-Ala)-Sar5-(74-01-00) | [B-Ala]-Sar5-ACIEEGQYCYRDMYMCA | 1841 |
| BCY634 | 43 | Ac-(74-01-00)-Sar6-K(FI) | [Ac]ACIEEGQYCYRDMYMCA-Sar6-K(FI) | 1376 |
| BCY636 | 44 | (74-01-01)-Sar6-K(FI) | ACIEEGQYCYADPYMCA-Sar6-K(FI) | 123.9 |
| BCY635 | 45 | (B-Ala)-Sar5-(74-01-01) | [B-Ala]-Sar5-ACIEEGQYCYADPYMCA | 126 |
| BCY638 | 46 | (74-01-02)-Sar6-K | ACIEEGQYCYADPYYCASar6-K | 192.5 |
| BCY637 | 47 | (B-Ala)-Sar5-(74-01-02) | [B-Ala]-Sar5-ACIEEGQYCYADPYYCA | 122 |
| BCY639 | 48 | (74-01-03)-Sar6-K | ACIEEGQYCYSDPYYCA-Sar6-K | 229 |
| BCY640 | 49 | (74-01-04)-Sar6-K | ACIEEGQYCFADPYMCA-Sar6-K | 84 |
| BCY641 | 50 | G-Sar5-(74-01-04) | G-Sar5-ACIEEGQYCFADPYMCA | 152.5 |
| BCY7238 | 51 | Ac-(74-01-04)Lys1(PEG12) | Ac-CK(Peg12)EEGQYCFADPYMC | >>3000 |
| BCY7239 | 52 | Ac-(74-01-04)Lys2(PEG12) | Ac-CIK(Peg12)EGQYCFADPYMC | 579 |
| BCY7240 | 53 | Ac-(74-01-04)Lys3(PEG12) | Ac-CIEK(Peg12)GQYCFADPYMC | 384 |
| BCY7241 | 54 | Ac-(74-01-04)Lys4(PEG12) | Ac-CIEEK(Peg12)QYCFADPYMC | >>3000 |
| BCY7242 | 55 | Ac-(74-01-04)Lys5(PEG12) | Ac-CIEEGK(Peg12)YCFADPYMC | 48.3 |
| BCY7243 | 56 | Ac-(74-01-04)Lys6(PEG12) | Ac-CIEEGQK(Peg12)CFADPYMC | >>3000 |
| BCY7244 | 57 | Ac-(74-01-04)Lys7(PEG12) | Ac-CIEEGQYCK(Peg12)ADPYMC | 296 |
| BCY7245 | 58 | Ac-(74-01-04)Lys8(PEG12) | Ac-CIEEGQYCFK(Peg12)DPYMC | 777 |
| BCY7246 | 59 | Ac-(74-01-04)Lys9(PEG12) | Ac-CIEEGQYCFAK(Peg12)PYMC | >>3000 |
| BCY7247 | 60 | Ac-(74-01-04)Lys10(PEG12) | Ac-CIEEGQYCFADK(Peg12)YMC | 239 |
| BCY7248 | 61 | Ac-(74-01-04)Lys11(PEG12) | Ac-CIEEGQYCFADPK(Peg12)MC | 744 |
| BCY7249 | 62 | Ac-(74-01-04)Lys12(PEG12) | Ac-CIEEGQYCFADPYK(Peg12)C | 288 |
| BCY7416 | 63 | Ac-(74-01-04)D-Lys4(PEG12)Nle12 | [Ac]CIEE[dK(PEG12FI)]QYCFADPY[Nle]C | 50.5 |

TABLE 1-continued

Direct Binding Results with Selected Peptides

| Peptide Number | SEQ ID NO: | Peptide Reference | Sequence | Kd nM |
|---|---|---|---|---|
| BCY7519 | 64 | (74-01-04) Nle12 | ACIEEGQYCFADPY[Nle]CA | 61 |
| BCY7520 | 65 | (Peg12)-(74-01-04) Nle12 | [Peg12]-ACIEEGQYCFADPY[Nle]CA | 121 |
| BCY642 | 66 | (74-01-05)-Sar6-K | ACIEEGQYCYADHQLCA-Sar6-K | 245.5 |
| BCY643 | 67 | (74-01-06)-Sar6-K | ACIEEGQYCHADPYYCA-Sar6-K | 148 |
| BCY644 | 68 | (74-01-07)-Sar6-K | ACIEEGQYCHADPYFCA-Sar6-K | 145 |
| BCY645 | 69 | (74-01-08)-Sar6-K | ACIEEGQYCYADHYMCA-Sar6-K | 146.5 |
| BCY646 | 70 | (74-01-09)-Sar6-K | ACIEEGQYCYADPYLCA-Sar6-K | 105 |
| BCY647 | 71 | (74-01-09-T03)-Sar6-K(Fl) | ACIEEGQYCYADPYLCSVG-Sar6-K | 391.5 |
| BCY648 | 72 | (B-Ala)-Sar5-(74-01-09-T03) | (Fl)G-Sar5-ACIEEGQYCYADPYLCSVG | 228 |
| BCY649 | 73 | (74-01-10)-Sar6-K | ACIEEGQYCYSDPYLCA-Sar6-K | 207 |
| BCY650 | 74 | (74-01-11)-Sar6-K | ACIEEGQYCFADPYLCA-Sar6-K | 86.5 |
| BCY652 | 75 | (74-01-13)-Sar6-K | ACIEEGQYCHADPYMCA-Sar6-K | 142 |
| BCY653 | 76 | (74-01-14)-Sar6-K | ACIEEGQYCHADPQMCA-Sar6-K | 383 |
| BCY655 | 77 | (74-01-16)-Sar6-K | ACDIGPPYCYRDMYMCA-Sar6-K | 1337 |
| BCY656 | 78 | (74-01-17)-Sar6-K | ADIGPPYCYADPYMCA-Sar6-K | 240 |
| BCY7251 | 79 | (74-01-19-N002)-Sar6-K | ACLDPGPFCFADPYMCA-Sar6-K | 193 |
| BCY7253 | 80 | (74-01-20-N002)-Sar6-K | ACLDEGPYCFADPYFCA-Sar6-K | 183 |
| BCY7255 | 81 | (74-01-21-N002)-Sar6-K | ACINEGPYCFADPYMCA-Sar6-K | 136 |
| BCY7257 | 82 | (74-01-22-N002)-Sar6-K | ACIEQGPFCFADPYMCA-Sar6-K | 109 |
| BCY7259 | 83 | (74-01-23-N002)-Sar6-K | ACVEEGPFCFADPYYCA-Sar6-K | 105 |
| BCY7261 | 84 | (74-01-24-N002)-Sar6-K | ACLDEGPFCFSDPYMCA-Sar6-K | 453 |
| BCY657 | 85 | (B-Ala)-Sar5-(74-02-00) | [B-Ala]-Sar5-ACDEWGLFCIPHSDCA | 3621 |
| BCY659 | 86 | (74-02-01)-Sar6-K | ACDEWGLYCFAHPDCA-Sar6-K | 1041 |
| BCY7119 | 87 | (74-13-00-T02)-Sar6-K | ACLDPGPYCYADPYMCTFH-Sar6-K | 144 |
| BCY660 | 88 | (74-19-00-T01)-Sar6-K | ACIEPGPFCYADPYMCNRV-Sar6-K | 183.5 |
| BCY661 | 89 | (B-Ala)-Sar5-(74-19-00-T01) | G-Sar5-ACIEPGPFCYADPYMCNRV | 412 |
| BCY7120 | 90 | (74-20-00-T01)-Sar6-K | ACLEPGPYCYADPYMCTHL-Sar6-K | 160 |
| BCY7122 | 91 | (74-22-03-N004)-Sar6-K | ACLPPGPYCFPDPYFCA-Sar6-K | 147 |

TABLE 2

Alanine Scan Results

| Peptide Number | SEQ ID NO: | Peptide Reference | Sequence | Kd nM |
|---|---|---|---|---|
| BCY7151 | 92 | [PEG3]-(74-01-04) Nle12 | [PEG3]-ACIEEGQYCFADPY[Nle]CA | 24.0 |
| BCY7283 | 93 | [PEG3]-(74-01-04) Ala1 Nle12 | [PEG3]-ACAEEGQYCFADPY(Nle)CA | 231 |
| BCY7284 | 94 | [PEG3]-(74-01-04) Ala2 Nle12 | [PEG3]-ACIAEGQYCFADPY(Nle)CA | 160 |
| BCY7285 | 95 | [PEG3]-(74-01-04) Ala3 Nle12 | [PEG3]-ACIEAGQYCFADPY(Nle)CA | 185 |

TABLE 2-continued

Alanine Scan Results

| Peptide Number | SEQ ID NO: | Peptide Reference | Sequence | Kd nM |
|---|---|---|---|---|
| BCY7286 | 96 | [PEG3]-(74-01-04) Ala4 Nle12 | [PEG3]-ACIEEAQYCFADPY(Nle)CA | 2568 |
| BCY7287 | 97 | [PEG3]-(74-01-04) Ala5 Nle12 | [PEG3]-ACIEEGAYCFADPY(Nle)CA | 25.5 |
| BCY7288 | 98 | [PEG3]-(74-01-04) Ala6 Nle12 | [PEG3]-ACIEEGQACFADPY(Nle)CA | 2322 |
| BCY7289 | 99 | [PEG3]-(74-01-04) Ala7 Nle12 | [PEG3]-ACIEEGQYCAADPY(Nle)CA | 904 |
| BCY7290 | 100 | [PEG3]-(74-01-04) Ala9 Nle12 | [PEG3]-ACIEEGQYCFAAPY(Nle)CA | >>3000 |
| BCY7292 | 101 | [PEG3]-(74-01-04) Ala11 Nle12 | [PEG3]-ACIEEGQYCFADPA(Nle)CA | 593 |
| BCY7293 | 102 | [PEG3]-(74-01-04) Ala12 | [PEG3]-ACIEEGQYCFADPYACA | 417 |
| BCY7294 | 103 | [PEG3]-(74-01-04) D-Ala1 Nle12 | [PEG3]-ACaEEGQYCFADPY(Nle)CA | >>3000 |
| BCY7295 | 104 | [PEG3]-(74-01-04) D-Ala2 Nle12 | [PEG3]-ACIaEGQYCFADPY(Nle)CA | >>3000 |
| BCY7296 | 105 | [PEG3]-(74-01-04) D-Ala3 Nle12 | [PEG3]-ACIEaGQYCFADPY(Nle)CA | >>3000 |
| BCY7297 | 106 | [PEG3]-(74-01-04) D-Ala4 Nle12 | [PEG3]-ACIEEaQYCFADPY(Nle)CA | 25.2 |
| BCY7298 | 107 | [PEG3]-(74-01-04) D-Ala5 Nle12 | [PEG3]-ACIEEGaYCFADPY(Nle)CA | 756 |
| BCY7299 | 108 | [PEG3]-(74-01-04) D-Ala6 Nle12 | [PEG3]-ACIEEGQaCFADPY(Nle)CA | >>3000 |
| BCY7300 | 109 | [PEG3]-(74-01-04) D-Ala7 Nle12 | [PEG3]-ACIEEGQYcADPY(Nle)CA | >>3000 |
| BCY7301 | 110 | [PEG3]-(74-01-04) D-Ala8 Nle12 | [PEG3]-ACIEEGQYCFaDPY(Nle)CA | >>3000 |
| BCY7302 | 111 | [PEG3]-(74-01-04) D-Ala9 Nle12 | [PEG3]-ACIEEGQYCFAaPY(Nle)CA | >>3000 |
| BCY7303 | 112 | [PEG3]-(74-01-04) D-Ala10 Nle12 | [PEG3]-ACIEEGQYCFADaY(Nle)CA | 968 |
| BCY7304 | 113 | [PEG3]-(74-01-04) D-Ala11 Nle12 | [PEG3]-ACIEEGQYCFADPa(Nle)CA | >>3000 |
| BCY7305 | 114 | [PEG3]-(74-01-04) D-Ala12 | [PEG3]-ACIEEGQYCFADPYaCA | >>3000 |

TABLE 3

Direct Binding Results with Selected Peptides

| Peptide Number | SEQ ID NO: | Peptide Reference | Sequence | Kd nM |
|---|---|---|---|---|
| BCY7151 | 92 | [PEG3]-(74-01-04) Nle12 | [PEG3]-ACIEEGQYCFADPY[Nle]CA | 24.0 |
| BCY7152 | 115 | [PEG3]-(74-01-04) Leu1 Nle12 | [PEG3]-ACLEEGQYCFADPY[Nle]CA | 55.1 |
| BCY7153 | 116 | [PEG3]-(74-01-04) Nle1 Nle12 | [PEG3]-AC[Nle]EEGQYCFADPY[Nle]CA | 122.6 |
| BCY7154 | 117 | [PEG3]-(74-01-04) Chg1 Nle12 | [PEG3]-AC-Chg-EEGQYCFADPY[Nle]CA | 20.3 |
| BCY7155 | 118 | [PEG3]-(74-01-04) Cha1 Nle12 | [PEG3]-AC-Cha-EEGQYCFADPY[Nle]CA | 175.5 |
| BCY7156 | 119 | [PEG3]-(74-01-04) Pro2 Nle12 | [PEG3]-ACIPEGQYCFADPY[Nle]CA | 10.4 |
| BCY7157 | 120 | [PEG3]-(74-01-04) Asp2 Nle12 | [PEG3]-ACIDEGQYCFADPY[Nle]CA | 26.2 |
| BCY7158 | 121 | [PEG3]-(74-01-04) Aad2 Nle12 | [PEG3]-ACI-Aad-EGQYCFADPY[Nle]CA | 22.3 |
| BCY7159 | 122 | [PEG3]-(74-01-04) Api2 Nle12 | [PEG3]-ACI-Api-EGQYCFADPY[Nle]CA | 58.0 |
| BCY7160 | 123 | [PEG3]-(74-01-04) Pro3 Nle12 | [PEG3]-ACIEPGQYCFADPY[Nle]CA | 68.1 |
| BCY7161 | 124 | [PEG3]-(74-01-04) Asp3 Nle12 | [PEG3]-ACIEDGQYCFADPY[Nle]CA | 282.1 |
| BCY7162 | 125 | [PEG3]-(74-01-04) Aad3 Nle12 | [PEG3]-ACIE-Aad-GQYCFADPY[Nle]CA | 39.8 |
| BCY7163 | 126 | [PEG3]-(74-01-04) Api3 Nle12 | [PEG3]-ACIE-Api-GQYCFADPY[Nle]CA | 126.3 |
| BCY7164 | 127 | [PEG3]-(74-01-04) Sar4 Nle12 | [PEG3]-ACIEE-Sar-QYCFADPY[Nle]CA | 326.0 |

TABLE 3-continued

Direct Binding Results with Selected Peptides

| Peptide Number | SEQ ID NO: | Peptide Reference | Sequence | Kd nM |
|---|---|---|---|---|
| BCY7165 | 128 | [PEG3]-(74-01-04) D-Lys4 Nle12 | [PEG3]-ACIEE-DLys-QYCFADPY[Nle]CA | 24.0 |
| BCY7166 | 129 | [PEG3]-(74-01-04) D-Phe4 Nle12 | [PEG3]-ACIEE-DPhe-QYCFADPY[Nle]CA | 10.0 |
| BCY7167 | 130 | [PEG3]-(74-01-04) D-Glu4 Nle12 | [PEG3]-ACIEE-DGlu-QYCFADPY[Nle]CA | 31.9 |
| BCY7168 | 131 | [PEG3]-(74-01-04) D-Gln4 Nle12 | [PEG3]-ACIEE-DGln-QYCFADPY[Nle]CA | 15.7 |
| BCY7169 | 132 | [PEG3]-(74-01-04) D-Leu4 Nle12 | [PEG3]-ACIEE-DLeu-QYCFADPY[Nle]CA | 46.1 |
| BCY7170 | 133 | [PEG3]-(74-01-04) D-Ser4 Nle12 | [PEG3]-ACIEE-DSer-QYCFADPY[Nle]CA | 13.9 |
| BCY7172 | 134 | [PEG3]-(74-01-04) N-Me-D-Ala4 Nle12 | [PEG3]-ACIEE-MeDala-QYCFADPY[Nle]CA | 546.4 |
| BCY7173 | 135 | [PEG3]-(74-01-04) Aib4 Nle12 | [PEG3]-ACIEE-Aib-QYCFADPY[Nle]CA | 414.0 |
| BCY7174 | 136 | [PEG3]-(74-01-04) Pro5 Nle12 | [PEG3]-ACIEEGPYCFADPY[Nle]CA | 6.13 |
| BCY7175 | 137 | [PEG3]-(74-01-04) Phe6 Nle12 | [PEG3]-ACIEEGQFCFADPY[Nle]CA | 25.3 |
| BCY7176 | 138 | [PEG3]-(74-01-04) 2MePhe6 Nle12 | [PEG3]-ACIEEGQ-2MeF-CFADPY[Nle]CA | 88.4 |
| BCY7177 | 139 | [PEG3]-(74-01-04) 3MePhe6 Nle12 | [PEG3]-ACIEEGQ-3MeF-CFADPY[Nle]CA | 43.7 |
| BCY7178 | 140 | [PEG3]-(74-01-04) 4MePhe6 Nle12 | [PEG3]-ACIEEGQ-4MeF-CFADPY[Nle]CA | 21.8 |
| BCY7179 | 141 | [PEG3]-(74-01-04) 4FPhe6 Nle12 | [PEG3]-ACIEEGQ-4FF-CFADPY[Nle]CA | 30.5 |
| BCY7180 | 142 | [PEG3]-(74-01-04) 3FPhe6 Nle12 | [PEG3]-ACIEEGQ-3FF-CFADPY[Nle]CA | 54.4 |
| BCY7181 | 143 | [PEG3]-(74-01-04) 2MePhe7 Nle12 | [PEG3]-ACIEEGQC-2MeF-ADPY[Nle]CA | 86.4 |
| BCY7182 | 144 | [PEG3]-(74-01-04) 3MePhe7 Nle12 | [PEG3]-ACIEEGQC-3MeF-ADPY[Nle]CA | 63.3 |
| BCY7183 | 145 | [PEG3]-(74-01-04) 4MePhe7 Nle12 | [PEG3]-ACIEEGQC-4MeF-ADPY[Nle]CA | 34.2 |
| BCY7184 | 146 | [PEG3]-(74-01-04) Phg7 Nle12 | [PEG3]-ACIEEGQC-PheG-ADPY[Nle]CA | 2813.3 |
| BCY7185 | 147 | [PEG3]-(74-01-04) 4FPhe7 Nle12 | [PEG3]-ACIEEGQC-4FF-ADPY[Nle]CA | 19.6 |
| BCY7186 | 148 | [PEG3]-(74-01-04) Gly8 Nle12 | [PEG3]-ACIEEGQYCFGDPY[Nle]CA | 244.2 |
| BCY7187 | 149 | [PEG3]-(74-01-04) Ser8 Nle12 | [PEG3]-ACIEEGQYCFSDPY[Nle]CA | 83.9 |
| BCY7188 | 150 | [PEG3]-(74-01-04) Pro8 Nle12 | [PEG3]-ACIEEGQYCFPDPY[Nle]CA | 363.1 |
| BCY7189 | 151 | [PEG3]-(74-01-04) Asn8 Nle12 | [PEG3]-ACIEEGQYCFANPY[Nle]CA | 655.8 |
| BCY7190 | 152 | [PEG3]-(74-01-04) Pip10 Nle12 | [PEG3]-ACIEEGQYCFAD-Pip-Y[Nle]CA | 326.8 |
| BCY7191 | 153 | [PEG3]-(74-01-04) N-Me-Ala10 Nle12 | [PEG3]-ACIEEGQYCFAD-MeAla-Y[Nle]CA | 460.2 |
| BCY7192 | 154 | [PEG3]-(74-01-04) Sar10 Nle12 | [PEG3]-ACIEEGQYCFAD-Sar-Y[Nle]CA | 220.6 |
| BCY7193 | 155 | [PEG3]-(74-01-04) Aib10 Nle12 | [PEG3]-ACIEEGQYCFAD-Aib-Y[Nle]CA | 146.9 |
| BCY7195 | 156 | [PEG3]-(74-01-04) tBuAla1 Nle12 | [PEG3]AC[tBuAla]EEGQYCFADPY[Nle]CA | 15.7 |
| BCY7196 | 157 | [PEG3]-(74-01-04) HLeu1 Nle12 | [PEG3]AC[HLeu]EEGQYCFADPY[Nle]CA | 138.5 |
| BCY7197 | 158 | [PEG3]-(74-01-04) 2FPhe6 Nle12 | [PEG3]ACIEEGQ[2FPhe]CFADPY[Nle]CA | 95.1 |
| BCY7198 | 159 | [PEG3]-(74-01-04) 2FPhe7 Nle12 | [PEG3]ACIEEGQYC[2FPhe]ADPY[Nle]CA | 28.1 |
| BCY7199 | 160 | [PEG3]-(74-01-04) CF3G8 Nle12 | [PEG3]ACIEEGQYCF[CF3G]DPY[Nle]CA | 172.0 |
| BCY7200 | 161 | [PEG3]-(74-01-04) pCoPhe11 Nle12 | [PEG3]ACIEEGQYCFADP[pCoPhe][Nle]CA | 364.6 |
| BCY7201 | 162 | [PEG3]-(74-01-04) pCaPhe11 Nle12 | [PEG3]ACIEEGQYCFADP[pCaPhe][Nle]CA | 533.4 |
| BCY7202 | 163 | [PEG3]-(74-01-04) Gln11 Nle12 | [PEG3]ACIEEGQYCFADPQ[Nle]CA | 216.0 |
| BCY7205 | 164 | [PEG3]-(74-01-04) 2MePhe11 Nle12 | [PEG3]ACIEEGQYCFADP[2MePhe][Nle]CA | 147.3 |

TABLE 3-continued

Direct Binding Results with Selected Peptides

| Peptide Number | SEQ ID NO: | Peptide Reference | Sequence | Kd nM |
|---|---|---|---|---|
| BCY7206 | 165 | [PEG3]-(74-01-04) 3MePhe11 Nle12 | [PEG3]ACIEEGQYCFADP[3MePhe][Nle]CA | 157.8 |
| BCY7207 | 166 | [PEG3]-(74-01-04) 4MePhe11 Nle12 | [PEG3]ACIEEGQYCFADP[4MePhe][Nle]CA | 185.8 |
| BCY7208 | 167 | [PEG3]-(74-01-04) Cit11 Nle12 | [PEG3]ACIEEGQYCFADP[Cit][Nle]CA | 657.4 |
| BCY7209 | 168 | [PEG3]-(74-01-04) 4FPhe11 Nle12 | [PEG3]ACIEEGQYCFADP[4FPhe][Nle]CA | 154.1 |
| BCY7210 | 169 | [PEG3]-(74-01-04) tBuAla12 | [PEG3]ACIEEGQYCFADPY[tBuAla]CA | 70.0 |
| BCY7211 | 170 | [PEG3]-(74-01-04) HLeu12 | [PEG3]ACIEEGQYCFADPY[HLeu]CA | 39.1 |
| BCY7212 | 171 | [PEG3]-(74-01-04) Ile12 | [PEG3]ACIEEGQYCFADPYICA | 140.3 |
| BCY7213 | 172 | [PEG3]-(74-01-04) Cha12 | [PEG3]ACIEEGQYCFADPY[Cha]CA | 62.1 |
| BCY7214 | 173 | [PEG3]-(74-01-04) Phe12 | [PEG3]ACIEEGQYCFADPYFCA | 50.1 |
| BCY7215 | 174 | [PEG3]-(74-01-04) 2MePhe12 | [PEG3]ACIEEGQYCFADPY[2MePhe]CA | 58.2 |
| BCY7216 | 175 | [PEG3]-(74-01-04) 3MePhe12 | [PEG3]ACIEEGQYCFADPY[3MePhe]CA | 88.0 |
| BCY7217 | 176 | [PEG3]-(74-01-04) 4MePhe12 | [PEG3]ACIEEGQYCFADPY[4MePhe]CA | 134.2 |
| BCY7218 | 177 | [PEG3]-(74-01-04) Cys1Pen Nle12 | [PEG3]A[Pen]IEEGQYCFADPY[Nle]CA | 40.7 |
| BCY7219 | 178 | [PEG3]-(74-01-04) Cys2Pen Nle12 | [PEG3]ACIEEGQY[Pen]FADPY[Nle]CA | 482.1 |
| BCY7220 | 179 | [PEG3]-(74-01-04) Cys3Pen Nle12 | [PEG3]ACIEEGQYCFADPY[Nle][Pen]A | 2465.1 |
| BCY7221 | 180 | [PEG3]-(74-01-04) Cys1HCys Nle12 | [PEG3]A[HCys]IEEGQYCFADPY[Nle]CA | 50.8 |
| BCY7222 | 181 | [PEG3]-(74-01-04) Cys2HCys Nle12 | [PEG3]ACIEEGQY[HCys]FADPY[Nle]CA | 1493.1 |
| BCY7223 | 182 | [PEG3]-(74-01-04) Cys3HCys Nle12 | [PEG3]ACIEEGQYCFADPY[Nle][HCys]A | 279.6 |
| BCY7224 | 183 | [PEG3]-(74-01-04) 3FPhe7 Nle12 | [PEG3]ACIEEGQYC[3FPhe]ADPY[Nle]CA | 39.8 |
| BCY7306 | 184 | [PEG3]-(74-01-04) TetraZ2 Nle12 | [PEG3]-ACI[TetraZ]EGQYCFADPY[Nle]CA | 289.3 |
| BCY7308 | 185 | [PEG3]-(74-01-04) TetraZ9 Nle12 | [PEG3]-ACIEEGQYCFA[TetraZ]PY[Nle]CA | 842.1 |
| BCY7309 | 186 | [PEG3]-(74-01-04) HGln11 Nle12 | [PEG3]-ACIEEGQYCFADP[HGln][Nle]CA | 536.9 |
| BCY7310 | 187 | [PEG3]-(74-01-04) Ahp1 Nle12 | [PEG3]-AC+AhNEEGQYCFADPY[Nle]CA | 278.5 |
| BCY7311 | 188 | [PEG3]-(74-01-04) Ahp12 | [PEG3]-ACIEEGQYCFADPY[Ahp]CA | 19.2 |

2. CD137 Biacore Experiments (a) Amine Coupled CD137 Target Assay Description

Biacore experiments were performed to determine $k_a$ ($M^{-1}s^{-1}$), $k_d$ ($s^{-1}$), $K_D$ (nM) values of peptides binding to human CD137 (AcroBiosystems) protein. CD137 protein was diluted and immobilised using the standard amine coupling procedure to chip CM5 (#BR-1005-30). CD137 protein was diluted to 10 ug/ml in NaAc pH 5.5 and used for coupling. Ethanolamine is then injected to deactivate remaining active esters.

The CD137 protein was immobilise at 180 RUs of CD137 protein to generate the maximum theoretical binding response with a peptide of 2500 MW will be ~25 RUs. A blank immobilisation of the reference flow cell (Fc1 or Fc3) is performed when amine coupling, following exactly the same procedure but with no injection of protein target. The peptides were tested at starting concentrations of 300-450 nM and diluted in ½ dilutions series. The DMSO concentration was adjusted to remain constant.

The peptide binding kinetic analysis was performed as follows at flow rate 50 μl/min, 200 sec association, 600 sec dissociation and 60 sec stabilization. The Bicyclic peptides were fitted using the 1:1 model Biacore T200 Evaluation software.

Selected peptides of the invention were tested in the above mentioned assay and the results are shown in Table 4:

TABLE 4

SPR Data for Selected Peptides of the Invention

| Peptide Number | SEQ ID NO: | Peptide Reference | Sequence | $K_D$ nM |
|---|---|---|---|---|
| BCY592 | 189 | 74-01-04 | ACIEEGQYCFADPYMCA | 70.9 |
| BCY589 | 190 | 74-01-01-T01 | HEHCIEEGQYCYADPYMCA | 124.1 |
| BCY599 | 191 | 74-01-11 | ACIEEGQYCFADPYLCA | 191.4 |
| BCY631 | 192 | 74-22-03 | ACLPPGPYCFPDPYFCA | 92.3 |

(b) Biotinylated CD137 Target Assay Description

Biacore experiments were performed to determine $k_a$ ($M^{-1}s^{-1}$), $k_d$ ($s^{-1}$), $K_D$ (nM) values of peptides binding to human CD137 protein. Recombinant human CD137 homotrimer (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of binding, a Biacore T200 instrument was used utilising a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl of onto the activated chip surface. Residual activated groups were blocked with a 7 min injection of 1 M ethanolamine (pH 8.5) and biotinylated CD137 captured to a level of 800-1800 RU. Buffer was changed to PBS/0.05% Tween 20 and a dilution series of the peptides was prepared in this buffer with a final DMSO concentration of 0.5%. The top peptide concentration was 500 nM or 10 μM with 6 further 3-fold (500 nm), or 2-fold (10 μM) dilutions in PBS/0.05% Tween 20. The SPR analysis was run at 25° C. at a flow rate of 90 μl/min with 60 seconds association and 100-600 seconds dissociation. After each cycle, a regeneration step (10 μl of 10 mM glycine pH 2) was employed. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using mass transport model allowing for mass transport effects where appropriate.

Selected peptides of the invention were tested in the above mentioned assay and the results are shown in Table 5:

TABLE 5

SPR Data for Selected Peptides of the Invention

| Peptide Number | SEQ ID NO: | Peptide Reference | Sequence | KD nM |
|---|---|---|---|---|
| BCY592 | 189 | 74-01-04 | ACIEEGQYCFADPYMCA | 41.8 |
| BCY593 | 193 | Ac-(74-01-04) | [Ac]CIEEGQYCFADPYMC | 37 |
| BCY3814 | 31 | 74-01-04 Nle12 | ACIEEGQYCFADPY(Nle)CA | 33.3 |
| BCY7527 | 194 | Ac-(74-01-04)-Dap Nle12 | [Ac]CIEEGQYCFADPY[Nle]C[Dap] | 16.4 |
| BCY7768 | 195 | PEG3-(74-01-04) Pro2 D-Phe4 Nle12 | [PEG3]ACIPE[dF]QYCFADPY[Nle]CA | 33.9 |
| BCY7770 | 196 | PEG3-(74-01-04) Pro2 D-Phe4 Pro5 Nle12 | [PEG3]ACIPE[dF]PYCFADPY[Nle]CA | 18.6 |
| BCY7772 | 197 | PEG3-(74-01-04) D-Phe4 Pro5 Nle12 | [PEG3]ACIEE[dF]PYCFADPY[Nle]CA | 39.7 |
| BCY7773 | 198 | PEG3-(74-01-04) Pro2 Pro5 Nle12 | PEG3]ACIPEGPYCFADPY[Nle]CA | 31.5 |
| BCY7774 | 199 | PEG3-(74-01-04) tBuAla1 Pro2 D-Phe4 Pro5 4MePhe6 4FPhe7 Nle12 | PEG3]AC[tBuAla]PE[dF]P[4MePhe]C[4FPhe]ADPY[Nle]CA | 8.69 |
| BCY7775 | 200 | PEG3-(74-01-04) tBuAla1 Pro2 D-Phe4 4MePhe6 4FPhe7 Nle12 | [PEG3]AC[tBuAla]PE[dF]Q[4MePhe]C[4FPhe]ADPY[Nle]CA | 18.2 |
| BCY7776 | 201 | PEG3-(74-01-04) tBuAla1 D-Phe4 Pro5 4MePhe6 4FPhe7 Nle12 | [PEG3]AC[tBuAla]EE[dF]P[4MePhe]C[4Fphe]ADPY[Nle]CA | 17.3 |
| BCY7777 | 202 | PEG3-(74-01-04) tBuAla1 D-Phe4 4MePhe6 4FPhe7 Nle12 | [PEG3]AC[tBuAla]EE[dF]Q[4MePhe]C[4FPhe]ADPY(Nle]CA | 66 |
| BCY7796 | 203 | PEG3-(74-01-04) HyP2 Nle12 | [PEG3]ACI[HyP]EGQYCFADPY[Nle]CA | 24.7 |
| BCY7798 | 204 | PEG3-(74-01-04) D-Trp4 Nle12 | [PEG3]ACIEE[dW]QYCFADPY[Nle]CA | 12.1 |
| BCY7799 | 205 | PEG3-(74-01-04) Aze5 Nle12 | [PEG3]ACIEEG[Aze]YCFADPY[Nle]CA | 69.9 |
| BCY7800 | 206 | PEG3-(74-01-04) Pip5 Nle12 | [PEG3]ACIEEG[Pip]YCFADPY[Nle]CA | 1490 |
| BCY7801 | 207 | PEG3-(74-01-04) 2Nal6 Nle12 | PEG3]ACIEEGQ[2Nal]CFADPY[Nle]CA | 18.7 |
| BCY7802 | 208 | PEG3-(74-01-04) 4MeOPhe6 Nle12 | PEG3]ACIEEGQ[4MeoPhe]CFADPY[Nle]CA | 17.8 |
| BCY7803 | 209 | PEG3-(74-01-04) Tyr6 Nle12 | [PEG3]ACIEEGQYCYADPY[Nle]CA | 54.9 |
| BCY7804 | 210 | PEG3-(74-01-04) Aze10 Nle12 | [PEG3]ACIEEGQYCFAD[Aze]Y[Nle]CA | 85.7 |
| BCY7806 | 211 | PEG3-(74-01-04) Hse(Me)12 | [PEG3]ACIEEGQYCFADPY[Hse(Me)]CA | 204 |

TABLE 5-continued

SPR Data for Selected Peptides of the Invention

| Peptide Number | SEQ ID NO: | Peptide Reference | Sequence | KD nM |
|---|---|---|---|---|
| BCY7923 | 212 | Ac-(74-01-04) NMeIle1 Nle12 | [Ac]AC[NMeIle]EEGQYCFADPY[Nle]CA | 1149 |
| BCY7924 | 213 | Ac-(74-01-04) Aze2 Nle12 | [Ac]ACI[Aze]EGQYCFADPY[Nle]CA | 59 |
| BCY7925 | 214 | Ac-(74-01-04) Pip2 Nle12 | [Ac]ACI[Pip]EGQYCFADPY[Nle]CA | 105 |
| BCY7926 | 215 | Ac-(74-01-04) NMeGlu2 Nle12 | [Ac]ACI[NMeGlu]EGQYCFADPY(Nle]CA | 220 |
| BCY7927 | 216 | Ac-(74-01-04) NMeGlu3 Nle12 | [Ac]ACIE[NMeGlu]GQYCFADPY[Nle]CA | 1650 |
| BCY7928 | 217 | Ac-(74-01-04) D-Asp4 Nle12 | [Ac]ACIEE[dD]QYCFADPY[Nle]CA | 97 |
| BCY7929 | 218 | Ac-(74-01-04) NMeAla5 Nle12 | [Ac]ACIEEG[NMeAla]YCFADPY[Nle]CA | 269 |
| BCY7930 | 219 | Ac-(74-01-04) NMeTyr6 Nle12 | Ac]ACIEEGQ[NMeTyr]CFADPY[Nle]CA | 993 |
| BCY7931 | 220 | Ac-(74-01-04) HPhe6 Nle12 | [Ac]ACIEEGQ[HPhe]CFADPY[Nle]CA | 1746 |
| BCY7933 | 221 | Ac-(74-01-04) 2Pal6 Nle12 | [Ac]ACIEEGQ[2Pal]CFADPY[Nle]CA | 790 |
| BCY7934 | 222 | Ac-(74-01-04) 3Pal6 Nle12 | [Ac]ACIEEGQ[3Pal]CFADPY[Nle]CA | 196 |
| BCY7936 | 223 | Ac-(74-01-04) 4,4-BPA6 Nle12 | [Ac]ACIEEGQ[44BPA]CFADPY[Nle]CA | 43 |
| BCY7937 | 224 | Ac-(74-01-04) HPhe7 Nle12 | [Ac]ACIEEGQC[HPhe]ADPY[Nle]CA | 556 |
| BCY7939 | 225 | Ac-(74-01-04) 2Pal7 Nle12 | [Ac]ACIEEGQC[2Pal]ADPY[Nle]CA | 98.6 |
| BCY7940 | 226 | Ac-(74-01-04) 3Pal7 Nle12 | [Ac]ACIEEGQC[3Pal]ADPY[Nle]CA | 58.6 |
| BCY7941 | 227 | Ac-(74-01-04) 4Pal7 Nle12 | [Ac]ACIEEGQC[4Pal]ADPY(Nle]CA | 44.4 |
| BCY7942 | 228 | Ac-(74-01-04) 4,4-BPA7 Nle12 | [Ac]ACIEEGQC[44BPA]ADPY[Nle]CA | 35.9 |
| BCY7943 | 229 | Ac-(74-01-04) 1Nal7 Nle12 | [Ac]ACIEEGQC[1Nal]ADPY[Nle]CA | 151 |
| BCY7944 | 230 | Ac-(74-01-04) 4tBuPhe7 Nle12 | Ac]ACIEEGQC[4tBuPhe]ADPY[Nle]CA | 42.2 |
| BCY7945 | 231 | Ac-(74-01-04) NMeAla8 Nle12 | [Ac]ACIEEGQCF[NMeAla]DPY[Nle]CA | 665 |
| BCY7950 | 232 | Ac-(74-01-04) 5,5-dmP5 Nle12 | [Ac]ACIEEG(55DMP]YCFADPY[Nle]CA | 31.1 |
| BCY7953 | 233 | Ac-(74-01-04) HyP10 Nle12 | [Ac]ACIEEGQYCFAD[HyP]Y[Nle]CA | 86.6 |
| BCY7954 | 234 | Ac-(74-01-04) Oic5 Nle12 | [Ac]ACIEEG[Oic]YCFADPY[Nle]CA | 11.1 |
| BCY7955 | 235 | Ac-(74-01-04) Oic10 Nle12 | [Ac]ACIEEGQYCFAD[Oic]Y[Nle]CA | 169 |
| BCY7956 | 236 | Ac-(74-01-04) Oic2 Nle12 | [Ac]ACI[Oic]EGQYCFADPY[Nle]CA | 228 |
| BCY7957 | 237 | Ac-(74-01-04) Oxa10 Nle12 | [Ac]ACIEEGQYCFAD[Oxa]Y[Nle]CA | 118 |
| BCY7958 | 238 | Ac-(74-01-04) Oxa2 Nle12 | [Ac]ACI[Oxa]EGQYCFADPY[Nle]CA | 20 |
| BCY7959 | 239 | Ac-(74-01-04) Oxa5 Nle12 | [Ac]ACIEEG[Oxa]YCFADPY[Nle]CA | 37.7 |
| BCY7960 | 240 | Ac-(74-01-04) Pro2 Pro5 Nle12 | [Ac]ACIPEGPYCFADPY[Nle]CA | 10.7 |
| BCY7952 | 241 | Ac-(74-01-04) HyP5 Nle12 | [Ac]ACIEEG[HyP]YCFADPY[Nle]CA | 11.8 |
| BCY7961 | 242 | Ac-(74-01-04) Pro2 DAla4 Pro5 Nle12 | [Ac]ACIPE[dA]PYCFADPY[Nle]CA | 10 |
| BCY7965 | 243 | Ac-(74-01-04) tBuAla1 Pro2 DAla4 Pro5 Nle12 | [Ac]AC[tBuAla]PE[dA]PYCFADPY[Nle]CA | 4.75 |
| BCY8217 | 244 | A-(74-01-04)-A D-Ala8 Nle12 | ACIEEGQYCF[dA]DPY[Nle]CA | 500 |
| BCY8656 | 245 | Ac-(74-01-04) tBuAla1 Nle12 | [Ac]AC[tBuAla]EEGQYCFADPY[Nle]CA | 31 (n = 2) |
| BCY8657 | 246 | Ac-(74-01-04) Chg1 Nle12 | [Ac]AC[Chg]EEGQYCFADPY[Nle]CA | 62.4 |
| BCY8658 | 247 | Ac-(74-01-04) Ac5c1 Nle12 | [Ac]AC[AC5C]EEGQYCFADPY[Nle]CA | 200 |

TABLE 5-continued

SPR Data for Selected Peptides of the Invention

| Peptide Number | SEQ ID NO: | Peptide Reference | Sequence | KD nM |
|---|---|---|---|---|
| BCY8659 | 248 | Ac-(74-01-04) Pro2 Nle12 | [Ac]ACIPEGQYCFADPY[Nle]CA | 33.4 |
| BCY8660 | 249 | Ac-(74-01-04) Gln2 Nle12 | [Ac]ACIQEGQYCFADPY[Nle]CA | 380 |
| BCY8661 | 250 | Ac-(74-01-04) Pro3 Nle12 | (Ac]ACIEPGQYCFADPY[Nle]CA | 154.5 (n = 2) |
| BCY8662 | 251 | Ac-(74-01-04) Gln3 Nle12 | [Ac]ACIEQGQYCFADPY[Nle]CA | 179 |
| BCY8663 | 252 | Ac-(74-01-04) D-Phe4 Nle12 | [Ac]ACIEE[dF]QYCFADPY[Nle]CA | 25.1 (n = 2) |
| BCY8664 | 253 | Ac-(74-01-04) D-Ala4 Nle12 | [Ac]ACIEE[dA]QYCFADPY[Nle]CA | 59.5 (n = 2) |
| BCY8665 | 254 | Ac-(74-01-04) Ac5c4 Nle12 | [Ac]ACIEE[AC5C]QYCFADPY[Nle]CA | 200 (n = 2) |
| BCY8667 | 255 | Ac-(74-01-04) Ala5 Nle12 | [Ac]ACIEEGAYCFADPY[Nle]CA | 68.5 (n = 3) |
| BCY8668 | 256 | Ac-(74-01-04) Aib5 Nle12 | [Ac]ACIEEG[Aib]YCFADPY[Nle]CA | 28.7 |
| BCY8669 | 257 | Ac-(74-01-04) Ac5c5 Nle12 | [Ac]ACIEEG[AC5C]YCFADPY[Nle]CA | 33.2 (n = 2) |
| BCY8670 | 258 | Ac-(74-01-04) 4MePhe6 Nle12 | [Ac]ACIEEGQ[4MePhe]CFADPY[Nle]CA | 1000 |
| BCY8671 | 259 | Ac-(74-01-04) 1Nal6 Nle12 | [Ac]ACIEEGQ[1Nal]CFADPY[Nle]CA | 297 |
| BCY8673 | 260 | Ac-(74-01-04) 2Nal7 Nle12 | [Ac]ACIEEGQYC[2Nal]ADPY[Nle]CA | 117 |
| BCY8674 | 261 | Ac-(74-01-04) 4NO2Phe7 Nle12 | [Ac]ACIEEGQYC[NO2Phe]ADPY[Nle]CA | 44.5 (n = 2) |
| BCY8675 | 262 | Ac-(74-01-04) 4BrPhe7 Nle12 | [Ac]ACIEEGQYC[4BrPhe]ADPY[Nle]CA | 57.5 (n = 2) |
| BCY8676 | 263 | Ac-(74-01-04) Abu8 Nle12 | [Ac]ACIEEGQYCF[Abu]DPY[Nle]CA | 1000 |
| BCY8677 | 264 | Ac-(74-01-04) Ahp12 | [Ac]ACIEEGQYCFADPY[Ahp]CA | 64.6 (n = 2) |
| BCY9273 | 265 | Ac-A-(74-01-04)-A | [Ac]ACIEEGQYCFADPYMCA | 108 |

3. CD137 Cell Activity

The biological activity of the CD137-specific peptides was tested using the cellular CD137 luciferase reporter assay kit (Promega). The cells in this commercially available kit express luciferase that is activated down-stream of CD137. This assay can be used to assess agonism (exemplified by CD137 ligand, CD137L) and antagonism (exemplified by bicyclic peptide 74-01-04-N002).

The Promega CD137 cell-activity assay uses NF-κB luciferase luminescence as a read-out of CD137 activation in Jurkat cells. Briefly, the experiments were performed by preparing medium by thawing FBS and adding 1% FBS to RPMI-1640 (Promega kit CS196005). Dilute agonists at concentration giving agonism CD137L (R&D systems 2295-4L/CF) diluted to 100 nM in the RPMI-1640 medium as final concentration in the assay. Dilute and then titrate down the bicyclic peptide in a sterile 96 well-plate. Suggested starting concentration for the bicyclic peptide is 10 μM, 100-fold excess over the agonist CD137L. Prepare enough reagent for duplicate samples and then perform ⅓ dilution series dilution series. Include positive control CD137L and bicyclic peptide alone. Thaw CD137 Jurkat cells in the water-bath and then add 500 μl cells to 9.5 ml pre-warmed 1% FBS RPMI-1640 medium. Add 50 μl cells/well to white cell culture plate. Add 12.5 μl bicyclic peptide (at 6× final concentration) to the cells. Then add 12.5 μl of agonist (at 6× final concentration) as duplicate samples or 1% FBS RPMI-1640 alone as background control.

Co-incubate cells together with CD137L agonist and bicyclic peptide for 6 h at 37° C., 5% $CO_2$. After 6 h thaw Bio-Glo™ and develop the assay at room-temperature. Add 75 μl Bio-Glo™ per well and incubate 5-10 min. Read luminescence signal on Pherastar plate-reader LUM plus models, gain 3600 using MARS software. Analyse data by calculating the percentage inhibition compared to CD137L alone. Transform the data to x=log (X), then plot log (inhibitor) vs. response variable slope (4 parameters) to calculate the $IC_{50}$ value.

The Promega CD137 cell-reporter assay (product number CS196008) was used to determine the antagonistic effect of the peptide BCY592 (74-01-04-N002; SEQ ID NO: 189) in inhibiting the natural ligand CD137L induction. The CD137 assay cells were co-incubated with trimeric CD137L (R&D systems)+BCY592 peptide. The CD137 reporter activity was determined as NF-κB promotor driven luciferase activity. The effect of the peptide BCY592 was plotted as % inhibition relative to baseline CD137L activity in the assay and used to determine the IC50-value.

The results are shown in FIG. 1 where it can be seen that the bicyclic peptide BCY592 specific for CD137 can act as an antagonist that inhibits CD137L activity. This result indicates that this peptide can be used in settings where it is desirable to block CD137 biological activity. It is known that CD137 activity can cause liver injury due to inflammation driven by the local immune cells. It is therefore believed that the bicyclic peptide BCY592 (and by inference other bicyclic CD137 peptides of the invention) may reduce CD137-CD137L driven inflammation which would reduce hepatotoxicity of CD137 agonists.

4. Fluorescence Polarization Competition Binding Assay

The binding site of the hCD137-specific Bicycle peptide was determined by competition experiment between a fluorescent labelled CD137 binding peptide and natural ligand CD137L, agonistic antibodies Urelumab and Utomilumab. Urelumab antibody binds to a distinct binding site while CD137L and Utomilumab both bind to the site termed the ligand-binding site.

The competitor agonists CD137L (R&D systems), Urelumab and Utomilumab were diluted in assay buffer 20 mM HEPES, 150 mM NaCl, 0.05% P20, pH7.5 to a top concentration of 500-1000 nM. The human CD137 protein (AcroBiosystems) was diluted to 500 nM final concentration in the assay. Finally, the fluorescent tracer peptide BCY640 (74-01-04-N001) was added at 1 nM. The assay was typically set up by adding 5 µL agonist competitor, 10 µL CD137 protein then 10 µL fluorescent peptide. The total volume of 25 µL was prepared in black walled and bottomed low binding low volume 384 well plates. Measurements were conducted on a BMG PHERAstar FS equipped with an FP 485 520 520 optic module at 25° C. with 200 flashes per well and a positioning delay of 0.1 second. Each well was measured every 5 minutes for 60 minutes. The gain was set in a well containing tracer without target protein. The mP-values at the end of the 60 minutes read were plotted against concentration of the agonists. Reduction in the mP-values indicates competition between the known agonist and the tracer peptide.

Figure 2:
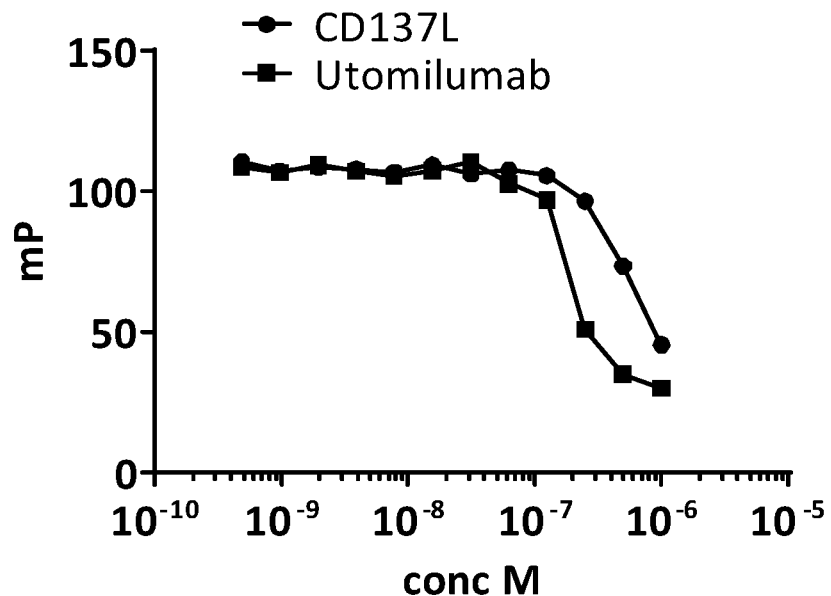
FIG. 2: Competition of CD137L or monoclonal antibody Utomilumab with a fluorescently labelled peptide BCY640 for binding to CD137 as measured by fluorescence polarization.
Figure 3:
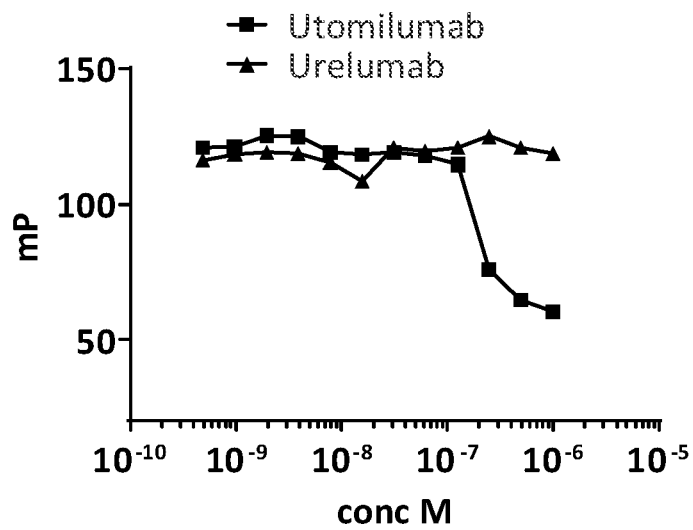
FIG. 3: Competition of monoclonal antibodies Utomilumab or Urelumab with a fluorescently labelled peptide BCY640 for binding to CD137 as measured by fluorescence polarization.

The results are shown in FIGS. 2 and 3 where it can be seen that the CD137 binding Bicycle (BCY640) binds to the physiologically relevant epitope that is shared with both the natural CD137 ligand (CD137L) and CD137 antibody (Utomilumab).

SEQUENCE LISTING

```
<160> NUMBER OF SEQ ID NOS: 267

<210> SEQ ID NO 1
<211> LENGTH: 15
<212> TYPE: PRT
<213> ORGANISM: Artificial
<220> FEATURE:
<223> OTHER INFORMATION: Synthetic Peptide

<400> SEQUENCE: 1

Cys Ile Glu Glu Gly Gln Tyr Cys Tyr Arg Asp Met Tyr Met Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Peptide

<400> SEQUENCE: 2

Cys Ile Glu Glu Gly Gln Tyr Cys Tyr Ala Asp Pro Tyr Met Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic Peptide

<400> SEQUENCE: 3

Cys Ile Glu Glu Gly Gln Tyr Cys Tyr Ala Asp Pro Tyr Tyr Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Peptide
```

```
<400> SEQUENCE: 4

Cys Ile Glu Glu Gly Gln Tyr Cys Tyr Ser Asp Pro Tyr Tyr Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic Peptide

<400> SEQUENCE: 5

Cys Ile Glu Glu Gly Gln Tyr Cys Phe Ala Asp Pro Tyr Met Cys
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic Peptide

<400> SEQUENCE: 6

Cys Ile Glu Glu Gly Gln Tyr Cys Tyr Ala Asp His Gln Leu Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic Peptide

<400> SEQUENCE: 7

Cys Ile Glu Glu Gly Gln Tyr Cys His Ala Asp Pro Tyr Tyr Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic Peptide

<400> SEQUENCE: 8

Cys Ile Glu Glu Gly Gln Tyr Cys His Ala Asp Pro Tyr Phe Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic Peptide

<400> SEQUENCE: 9

Cys Ile Glu Glu Gly Gln Tyr Cys Tyr Ala Asp His Tyr Met Cys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic Peptide
```

<400> SEQUENCE: 10

Cys Ile Glu Glu Gly Gln Tyr Cys Tyr Ala Asp Pro Tyr Leu Cys
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic Peptide

<400> SEQUENCE: 11

Cys Ile Glu Glu Gly Gln Tyr Cys Tyr Ser Asp Pro Tyr Leu Cys
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic Peptide

<400> SEQUENCE: 12

Cys Ile Glu Glu Gly Gln Tyr Cys Phe Ala Asp Pro Tyr Leu Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic Peptide

<400> SEQUENCE: 13

Cys Ile Glu Glu Gly Gln Tyr Cys His Ala Asp Pro Tyr Met Cys
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic Peptide

<400> SEQUENCE: 14

Cys Ile Glu Glu Gly Gln Tyr Cys His Ala Asp Pro Gln Met Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic Peptide

<400> SEQUENCE: 15

Cys Asp Ile Gly Pro Pro Tyr Cys Tyr Arg Asp Met Tyr Met Cys
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic Peptide

```
<400> SEQUENCE: 16

Cys Asp Ile Gly Pro Pro Tyr Cys Tyr Ala Asp Pro Tyr Met Cys
1               5                   10                  15

<210> SEQ ID NO 17
<211> LENGTH: 14
<212> TYPE: PRT
<213> ORGANISM: Artificial
<220> FEATURE:
<223> OTHER INFORMATION: Synthetic Peptide

<400> SEQUENCE: 17

Cys Asp Glu Trp Gly Leu Phe Cys Ile Pro His Ser Asp Cys
1               5                   10

<210> SEQ ID NO 18
<211> LENGTH: 14
<212> TYPE: PRT
<213> ORGANISM: Artificial
<220> FEATURE:
<223> OTHER INFORMATION: Synthetic Peptide

<400> SEQUENCE: 18

Cys Asp Glu Trp Gly Leu Tyr Cys Phe Ala His Pro Asp Cys
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic Peptide

<400> SEQUENCE: 19

Cys Ile Glu Pro Gly Pro Phe Cys Tyr Ala Asp Pro Tyr Met Cys
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: X
<222> LOCATION: (13)..(13)
<223> OTHER INFORMATION: X represents Y, Q or M
<220> FEATURE:
<221> NAME/KEY: misc_feature
<222> LOCATION: (14)..(14)
<223> OTHER INFORMATION: Xaa can be any naturally occurring amino acid

<400> SEQUENCE: 20

Cys Ile Glu Glu Gly Gln Tyr Cys Xaa Xaa Asp Xaa Xaa Xaa Cys
1               5                   10                  15

<210> SEQ ID NO 21
<211> LENGTH: 15
<212> TYPE: PRT
<213> ORGANISM: Artificial
<220> FEATURE:
```

```
<223> OTHER INFORMATION: Synthetic Peptide
<220> FEATURE:
<221> NAME/KEY: X
<222> LOCATION: (10)..(10)
<223> OTHER INFORMATION: X represents R or A
<220> FEATURE:
<221> NAME/KEY: X
<222> LOCATION: (12)..(12)
<223> OTHER INFORMATION: X represents M or P

<400> SEQUENCE: 21

Cys Asp Ile Gly Pro Pro Tyr Cys Tyr Xaa Asp Xaa Tyr Met Cys
1               5                   10                  15

<210> SEQ ID NO 22
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents F or Y
<220> FEATURE:
<221> NAME/KEY: X
<222> LOCATION: (9)..(9)
<223> OTHER INFORMATION: X represents I or F
<220> FEATURE:
<221> NAME/KEY: X
<222> LOCATION: (10)..(10)
<223> OTHER INFORMATION: X represents P or A
<220> FEATURE:
<221> NAME/KEY: X
<222> LOCATION: (12)..(12)
<223> OTHER INFORMATION: X represents S or P

<400> SEQUENCE: 22

Cys Asp Glu Trp Gly Leu Xaa Cys Xaa Xaa His Xaa Asp Cys
1               5                   10

<210> SEQ ID NO 23
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represent Nle

<400> SEQUENCE: 23

Cys Ile Glu Glu Gly Gln Tyr Cys Phe Ala Asp Pro Tyr Xaa Cys
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 24

Cys Ile Lys Glu Gly Gln Tyr Cys Phe Ala Asp Pro Tyr Xaa Cys
1               5                   10                  15
```

```
<210> SEQ ID NO 25
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 25

Cys Ile Glu Lys Gly Gln Tyr Cys Phe Ala Asp Pro Tyr Xaa Cys
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 26

Cys Ile Glu Glu Lys Gln Tyr Cys Phe Ala Asp Pro Tyr Xaa Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 27

Cys Ile Glu Glu Gly Lys Tyr Cys Phe Ala Asp Pro Tyr Xaa Cys
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 28

Cys Ile Glu Glu Gly Gln Tyr Cys Lys Ala Asp Pro Tyr Xaa Cys
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle
```

```
<400> SEQUENCE: 29

Cys Ile Glu Glu Gly Gln Tyr Cys Phe Ala Asp Lys Tyr Xaa Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic Peptide

<400> SEQUENCE: 30

Cys Ile Glu Glu Gly Gln Tyr Cys Phe Ala Asp Pro Tyr Lys Cys
1               5                   10                  15

<210> SEQ ID NO 31
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 31

Ala Cys Ile Glu Glu Gly Gln Tyr Cys Phe Ala Asp Pro Tyr Xaa Cys
1               5                   10                  15

Ala

<210> SEQ ID NO 32
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 32

Ala Cys Ile Glu Glu Gly Gln Tyr Cys Phe Ala Asp Pro Tyr Xaa Cys
1               5                   10                  15

<210> SEQ ID NO 33
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 33

Ala Cys Ile Lys Glu Gly Gln Tyr Cys Phe Ala Asp Pro Tyr Xaa Cys
1               5                   10                  15

Ala

<210> SEQ ID NO 34
<211> LENGTH: 17
<212> TYPE: PRT
<213> ORGANISM: Artificial
<220> FEATURE:
```

<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 34

Ala Cys Ile Glu Lys Gly Gln Tyr Cys Phe Ala Asp Pro Tyr Xaa Cys
1               5                   10                  15
Ala

<210> SEQ ID NO 35
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 35

Ala Cys Ile Glu Glu Lys Gln Tyr Cys Phe Ala Asp Pro Tyr Xaa Cys
1               5                   10                  15
Ala

<210> SEQ ID NO 36
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 36

Ala Cys Ile Glu Glu Gly Lys Tyr Cys Phe Ala Asp Pro Tyr Xaa Cys
1               5                   10                  15
Ala

<210> SEQ ID NO 37
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 37

Ala Cys Ile Glu Glu Gly Gln Tyr Cys Lys Ala Asp Pro Tyr Xaa Cys
1               5                   10                  15
Ala

<210> SEQ ID NO 38
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X

```
<222> LOCATION: (15)..(15)
<223> OTHER INFORMATION: X represents Nle

<400> SEQUENCE: 38

Ala Cys Ile Glu Glu Gly Gln Tyr Cys Phe Ala Asp Lys Tyr Xaa Cys
1               5                   10                  15
Ala

<210> SEQ ID NO 39
<211> LENGTH: 17
<212> TYPE: PRT
<213> ORGANISM: Artificial
<220> FEATURE:
<223> OTHER INFORMATION: Synthetic Peptide

<400> SEQUENCE: 39

Ala Cys Ile Glu Glu Gly Gln Tyr Cys Phe Ala Asp Pro Tyr Lys Cys
1               5                   10                  15
Ala

<210> SEQ ID NO 40
<211> LENGTH: 15
<212> TYPE: PRT
<213> ORGANISM: Artificial
<220> FEATURE:
<223> OTHER INFORMATION: Synthetic Peptide

<400> SEQUENCE: 40

Cys Leu Pro Pro Gly Gln Tyr Cys Phe Pro Asp Leu Leu Leu Cys
1               5                   10                  15

<210> SEQ ID NO 41
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents I, L, M or V
<220> FEATURE:
<221> NAME/KEY: X
<222> LOCATION: (3)..(3)
<223> OTHER INFORMATION: X represents E, D, P or S
<220> FEATURE:
<221> NAME/KEY: X
<222> LOCATION: (4)..(4)
<223> OTHER INFORMATION: X represents P, E or A
<220> FEATURE:
<221> NAME/KEY: X
<222> LOCATION: (6)..(6)
<223> OTHER INFORMATION: X represents P or Q
<220> FEATURE:
<221> NAME/KEY: X
<222> LOCATION: (7)..(7)
<223> OTHER INFORMATION: X represents Y or F
<220> FEATURE:
<221> NAME/KEY: X
<222> LOCATION: (13)..(13)
<223> OTHER INFORMATION: X represents Y or M
<220> FEATURE:
<221> NAME/KEY: X
<222> LOCATION: (14)..(14)
<223> OTHER INFORMATION: X represents M, L or Y

<400> SEQUENCE: 41

Cys Xaa Xaa Xaa Gly Xaa Xaa Cys Tyr Ala Asp Pro Xaa Xaa Cys
1               5                   10                  15
```

<210> SEQ ID NO 42
<211> LENGTH: 17
<212> TYPE: PRT
<213> ORGANISM: Artificial
<220> FEATURE:
<223> OTHER INFORMATION: Synthetic Peptide

<400> SEQUENCE: 42

Ala Cys Ile Glu Glu Gly Gln Tyr Cys Tyr Arg Asp Met Tyr Met Cys
1               5                   10                  15

Ala

<210> SEQ ID NO 43
<211> LENGTH: 17
<212> TYPE: PRT
<213> ORGANISM: Artificial
<220> FEATURE:
<223> OTHER INFORMATION: Synthetic Peptide

<400> SEQUENCE: 43

Ala Cys Ile Glu Glu Gly Gln Tyr Cys Tyr Arg Asp Met Tyr Met Cys
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Synthetic Peptide

<400> SEQUENCE: 44

Ala Cys Ile Glu Glu Gly Gln Tyr Cys Tyr Ala Asp Pro Tyr Met Cys
1               5                   10                  15

Ala

<210> SEQ ID NO 45
<211> LENGTH: 17
<212> TYPE: PRT
<213> ORGANISM: Artificial
<220> FEATURE:
<223> OTHER INFORMATION: Synthetic Peptide

<400> SEQUENCE: 45

Ala Cys Ile Glu Glu Gly Gln Tyr Cys Tyr Ala Asp Pro Tyr Met Cys
1               5                   10                  15

Ala

<210> SEQ ID NO 46
<211> LENGTH: 17
<212> TYPE: PRT
<213> ORGANISM: Artificial
<220> FEATURE:
<223> OTHER INFORMATION: Synthetic Peptide

<400> SEQUENCE: 46

Ala Cys Ile Glu Glu Gly Gln Tyr Cys Tyr Ala Asp Pro Tyr Tyr Cys
1               5                   10                  15

Ala

<210> SEQ ID NO 47
<211> LENGTH: 17
<212> TYPE: PRT

```
<213> ORGANISM: Artificial
<220> FEATURE:
<223> OTHER INFORMATION: Synthetic Peptide

<400> SEQUENCE: 47

Ala Cys Ile Glu Glu Gly Gln Tyr Cys Tyr Ala Asp Pro Tyr Tyr Cys
1               5                   10                  15

Ala

<210> SEQ ID NO 48
<211> LENGTH: 17
<212> TYPE: PRT
<213> ORGANISM: Artificial
<220> FEATURE:
<223> OTHER INFORMATION: Synthetic Peptide

<400> SEQUENCE: 48

Ala Cys Ile Glu Glu Gly Gln Tyr Cys Tyr Ser Asp Pro Tyr Tyr Cys
1               5                   10                  15

Ala

<210> SEQ ID NO 49
<211> LENGTH: 17
<212> TYPE: PRT
<213> ORGANISM: Artificial
<220> FEATURE:
<223> OTHER INFORMATION: Synthetic Peptide

<400> SEQUENCE: 49

Ala Cys Ile Glu Glu Gly Gln Tyr Cys Phe Ala Asp Pro Tyr Met Cys
1               5                   10                  15

Ala

<210> SEQ ID NO 50
<211> LENGTH: 17
<212> TYPE: PRT
<213> ORGANISM: Artificial
<220> FEATURE:
<223> OTHER INFORMATION: Synthetic Peptide

<400> SEQUENCE: 50

Ala Cys Ile Glu Glu Gly Gln Tyr Cys Phe Ala Asp Pro Tyr Met Cys
1               5                   10                  15

Ala

<210> SEQ ID NO 51
<211> LENGTH: 15
<212> TYPE: PRT
<213> ORGANISM: Artificial
<220> FEATURE:
<223> OTHER INFORMATION: Synthetic Peptide

<400> SEQUENCE: 51

Cys Lys Glu Glu Gly Gln Tyr Cys Phe Ala Asp Pro Tyr Met Cys
1               5                   10                  15

<210> SEQ ID NO 52
<211> LENGTH: 15
<212> TYPE: PRT
<213> ORGANISM: Artificial
<220> FEATURE:
<223> OTHER INFORMATION: Synthetic Peptide
```

<400> SEQUENCE: 52

Cys Ile Lys Glu Gly Gln Tyr Cys Phe Ala Asp Pro Tyr Met Cys
1               5                   10                  15

<210> SEQ ID NO 53
<211> LENGTH: 15
<212> TYPE: PRT
<213> ORGANISM: Artificial
<220> FEATURE:
<223> OTHER INFORMATION: Synthetic Peptide

<400> SEQUENCE: 53

Cys Ile Glu Lys Gly Gln Tyr Cys Phe Ala Asp Pro Tyr Met Cys
1               5                   10                  15

<210> SEQ ID NO 54
<211> LENGTH: 15
<212> TYPE: PRT
<213> ORGANISM: Artificial
<220> FEATURE:
<223> OTHER INFORMATION: Synthetic Peptide

<400> SEQUENCE: 54

Cys Ile Glu Glu Lys Gln Tyr Cys Phe Ala Asp Pro Tyr Met Cys
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic Peptide

<400> SEQUENCE: 55

Cys Ile Glu Glu Gly Lys Tyr Cys Phe Ala Asp Pro Tyr Met Cys
1               5                   10                  15

<210> SEQ ID NO 56
<211> LENGTH: 15
<212> TYPE: PRT
<213> ORGANISM: Artificial
<220> FEATURE:
<223> OTHER INFORMATION: Synthetic Peptide

<400> SEQUENCE: 56

Cys Ile Glu Glu Gly Gln Lys Cys Phe Ala Asp Pro Tyr Met Cys
1               5                   10                  15

<210> SEQ ID NO 57
<211> LENGTH: 15
<212> TYPE: PRT
<213> ORGANISM: Artificial
<220> FEATURE:
<223> OTHER INFORMATION: Synthetic Peptide

<400> SEQUENCE: 57

Cys Ile Glu Glu Gly Gln Tyr Cys Lys Ala Asp Pro Tyr Met Cys
1               5                   10                  15

<210> SEQ ID NO 58
<211> LENGTH: 15
<212> TYPE: PRT
<213> ORGANISM: Artificial
<220> FEATURE:
<223> OTHER INFORMATION: Synthetic Peptide -continued

```
<400> SEQUENCE: 58

Cys Ile Glu Glu Gly Gln Tyr Cys Phe Lys Asp Pro Tyr Met Cys
1               5                   10                  15

<210> SEQ ID NO 59
<211> LENGTH: 15
<212> TYPE: PRT
<213> ORGANISM: Artificial
<220> FEATURE:
<223> OTHER INFORMATION: Synthetic Peptide

<400> SEQUENCE: 59

Cys Ile Glu Glu Gly Gln Tyr Cys Phe Ala Lys Pro Tyr Met Cys
1               5                   10                  15

<210> SEQ ID NO 60
<211> LENGTH: 15
<212> TYPE: PRT
<213> ORGANISM: Artificial
<220> FEATURE:
<223> OTHER INFORMATION: Synthetic Peptide

<400> SEQUENCE: 60

Cys Ile Glu Glu Gly Gln Tyr Cys Phe Ala Asp Lys Tyr Met Cys
1               5                   10                  15

<210> SEQ ID NO 61
<211> LENGTH: 15
<212> TYPE: PRT
<213> ORGANISM: Artificial
<220> FEATURE:
<223> OTHER INFORMATION: Synthetic Peptide

<400> SEQUENCE: 61

Cys Ile Glu Glu Gly Gln Tyr Cys Phe Ala Asp Pro Lys Met Cys
1               5                   10                  15

<210> SEQ ID NO 62
<211> LENGTH: 15
<212> TYPE: PRT
<213> ORGANISM: Artificial
<220> FEATURE:
<223> OTHER INFORMATION: Synthetic Peptide

<400> SEQUENCE: 62

Cys Ile Glu Glu Gly Gln Tyr Cys Phe Ala Asp Pro Tyr Lys Cys
1               5                   10                  15

<210> SEQ ID NO 63
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle

<400> SEQUENCE: 63

Cys Ile Glu Glu Lys Gln Tyr Cys Phe Ala Asp Pro Tyr Xaa Cys
1               5                   10                  15

<210> SEQ ID NO 64
<211> LENGTH: 17
<212> TYPE: PRT
<213> ORGANISM: Artificial
```

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 64

Ala Cys Ile Glu Glu Gly Gln Tyr Cys Phe Ala Asp Pro Tyr Xaa Cys
1               5                   10                  15

Ala

<210> SEQ ID NO 65
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 65

Ala Cys Ile Glu Glu Gly Gln Tyr Cys Phe Ala Asp Pro Tyr Xaa Cys
1               5                   10                  15

Ala

<210> SEQ ID NO 66
<211> LENGTH: 17
<212> TYPE: PRT
<213> ORGANISM: Artificial
<220> FEATURE:
<223> OTHER INFORMATION: Synthetic Peptide

<400> SEQUENCE: 66

Ala Cys Ile Glu Glu Gly Gln Tyr Cys Tyr Ala Asp His Gln Leu Cys
1               5                   10                  15

Ala

<210> SEQ ID NO 67
<211> LENGTH: 17
<212> TYPE: PRT
<213> ORGANISM: Artificial
<220> FEATURE:
<223> OTHER INFORMATION: Synthetic Peptide

<400> SEQUENCE: 67

Ala Cys Ile Glu Glu Gly Gln Tyr Cys His Ala Asp Pro Tyr Tyr Cys
1               5                   10                  15

Ala

<210> SEQ ID NO 68
<211> LENGTH: 17
<212> TYPE: PRT
<213> ORGANISM: Artificial
<220> FEATURE:
<223> OTHER INFORMATION: Synthetic Peptide

<400> SEQUENCE: 68

Ala Cys Ile Glu Glu Gly Gln Tyr Cys His Ala Asp Pro Tyr Phe Cys
1               5                   10                  15

Ala
```

```
<210> SEQ ID NO 69
<211> LENGTH: 17
<212> TYPE: PRT
<213> ORGANISM: Artificial
<220> FEATURE:
<223> OTHER INFORMATION: Synthetic Peptide

<400> SEQUENCE: 69

Ala Cys Ile Glu Glu Gly Gln Tyr Cys Tyr Ala Asp His Tyr Met Cys
1               5                   10                  15

Ala

<210> SEQ ID NO 70
<211> LENGTH: 17
<212> TYPE: PRT
<213> ORGANISM: Artificial
<220> FEATURE:
<223> OTHER INFORMATION: Synthetic Peptide

<400> SEQUENCE: 70

Ala Cys Ile Glu Glu Gly Gln Tyr Cys Tyr Ala Asp Pro Tyr Leu Cys
1               5                   10                  15

Ala

<210> SEQ ID NO 71
<211> LENGTH: 19
<212> TYPE: PRT
<213> ORGANISM: Artificial
<220> FEATURE:
<223> OTHER INFORMATION: Synthetic Peptide

<400> SEQUENCE: 71

Ala Cys Ile Glu Glu Gly Gln Tyr Cys Tyr Ala Asp Pro Tyr Leu Cys
1               5                   10                  15

Ser Val Gly

<210> SEQ ID NO 72
<211> LENGTH: 19
<212> TYPE: PRT
<213> ORGANISM: Artificial
<220> FEATURE:
<223> OTHER INFORMATION: Synthetic Peptide

<400> SEQUENCE: 72

Ala Cys Ile Glu Glu Gly Gln Tyr Cys Tyr Ala Asp Pro Tyr Leu Cys
1               5                   10                  15

Ser Val Gly

<210> SEQ ID NO 73
<211> LENGTH: 17
<212> TYPE: PRT
<213> ORGANISM: Artificial
<220> FEATURE:
<223> OTHER INFORMATION: Synthetic Peptide

<400> SEQUENCE: 73

Ala Cys Ile Glu Glu Gly Gln Tyr Cys Tyr Ser Asp Pro Tyr Leu Cys
1               5                   10                  15

Ala

<210> SEQ ID NO 74
<211> LENGTH: 17
<212> TYPE: PRT
<213> ORGANISM: Artificial
```

```
<220> FEATURE:
<223> OTHER INFORMATION: Synthetic Peptide

<400> SEQUENCE: 74

Ala Cys Ile Glu Glu Gly Gln Tyr Cys Phe Ala Asp Pro Tyr Leu Cys
1               5                   10                  15
Ala

<210> SEQ ID NO 75
<211> LENGTH: 17
<212> TYPE: PRT
<213> ORGANISM: Artificial
<220> FEATURE:
<223> OTHER INFORMATION: Synthetic Peptide

<400> SEQUENCE: 75

Ala Cys Ile Glu Glu Gly Gln Tyr Cys His Ala Asp Pro Tyr Met Cys
1               5                   10                  15
Ala

<210> SEQ ID NO 76
<211> LENGTH: 17
<212> TYPE: PRT
<213> ORGANISM: Artificial
<220> FEATURE:
<223> OTHER INFORMATION: Synthetic Peptide

<400> SEQUENCE: 76

Ala Cys Ile Glu Glu Gly Gln Tyr Cys His Ala Asp Pro Gln Met Cys
1               5                   10                  15
Ala

<210> SEQ ID NO 77
<211> LENGTH: 17
<212> TYPE: PRT
<213> ORGANISM: Artificial
<220> FEATURE:
<223> OTHER INFORMATION: Synthetic Peptide

<400> SEQUENCE: 77

Ala Cys Asp Ile Gly Pro Pro Tyr Cys Tyr Arg Asp Met Tyr Met Cys
1               5                   10                  15
Ala

<210> SEQ ID NO 78
<211> LENGTH: 16
<212> TYPE: PRT
<213> ORGANISM: Artificial
<220> FEATURE:
<223> OTHER INFORMATION: Synthetic Peptide

<400> SEQUENCE: 78

Ala Asp Ile Gly Pro Pro Tyr Cys Tyr Ala Asp Pro Tyr Met Cys Ala
1               5                   10                  15

<210> SEQ ID NO 79
<211> LENGTH: 17
<212> TYPE: PRT
<213> ORGANISM: Artificial
<220> FEATURE:
<223> OTHER INFORMATION: Synthetic Peptide
```

<400> SEQUENCE: 79

Ala Cys Leu Asp Pro Gly Pro Phe Cys Phe Ala Asp Pro Tyr Met Cys
1               5                   10                  15
Ala

<210> SEQ ID NO 80
<211> LENGTH: 17
<212> TYPE: PRT
<213> ORGANISM: Artificial
<220> FEATURE:
<223> OTHER INFORMATION: Synthetic Peptide

<400> SEQUENCE: 80

Ala Cys Leu Asp Glu Gly Pro Tyr Cys Phe Ala Asp Pro Tyr Phe Cys
1               5                   10                  15
Ala

<210> SEQ ID NO 81
<211> LENGTH: 17
<212> TYPE: PRT
<213> ORGANISM: Artificial
<220> FEATURE:
<223> OTHER INFORMATION: Synthetic Peptide

<400> SEQUENCE: 81

Ala Cys Ile Asn Glu Gly Pro Tyr Cys Phe Ala Asp Pro Tyr Met Cys
1               5                   10                  15
Ala

<210> SEQ ID NO 82
<211> LENGTH: 17
<212> TYPE: PRT
<213> ORGANISM: Artificial
<220> FEATURE:
<223> OTHER INFORMATION: Synthetic Peptide

<400> SEQUENCE: 82

Ala Cys Ile Glu Gln Gly Pro Phe Cys Phe Ala Asp Pro Tyr Met Cys
1               5                   10                  15
Ala

<210> SEQ ID NO 83
<211> LENGTH: 17
<212> TYPE: PRT
<213> ORGANISM: Artificial
<220> FEATURE:
<223> OTHER INFORMATION: Synthetic Peptide

<400> SEQUENCE: 83

Ala Cys Val Glu Glu Gly Pro Phe Cys Phe Ala Asp Pro Tyr Tyr Cys
1               5                   10                  15
Ala

<210> SEQ ID NO 84
<211> LENGTH: 17
<212> TYPE: PRT
<213> ORGANISM: Artificial
<220> FEATURE:
<223> OTHER INFORMATION: Synthetic Peptide

<400> SEQUENCE: 84

Ala Cys Leu Asp Glu Gly Pro Phe Cys Phe Ser Asp Pro Tyr Met Cys
1               5                   10                  15

Ala

<210> SEQ ID NO 85
<211> LENGTH: 16
<212> TYPE: PRT
<213> ORGANISM: Artificial
<220> FEATURE:
<223> OTHER INFORMATION: Synthetic Peptide

<400> SEQUENCE: 85

Ala Cys Asp Glu Trp Gly Leu Phe Cys Ile Pro His Ser Asp Cys Ala
1               5                   10                  15

<210> SEQ ID NO 86
<211> LENGTH: 16
<212> TYPE: PRT
<213> ORGANISM: Artificial
<220> FEATURE:
<223> OTHER INFORMATION: Synthetic Peptide

<400> SEQUENCE: 86

Ala Cys Asp Glu Trp Gly Leu Tyr Cys Phe Ala His Pro Asp Cys Ala
1               5                   10                  15

<210> SEQ ID NO 87
<211> LENGTH: 19
<212> TYPE: PRT
<213> ORGANISM: Artificial
<220> FEATURE:
<223> OTHER INFORMATION: Synthetic Peptide

<400> SEQUENCE: 87

Ala Cys Leu Asp Pro Gly Pro Tyr Cys Tyr Ala Asp Pro Tyr Met Cys
1               5                   10                  15

Thr Phe His

<210> SEQ ID NO 88
<211> LENGTH: 19
<212> TYPE: PRT
<213> ORGANISM: Artificial
<220> FEATURE:
<223> OTHER INFORMATION: Synthetic Peptide

<400> SEQUENCE: 88

Ala Cys Ile Glu Pro Gly Pro Phe Cys Tyr Ala Asp Pro Tyr Met Cys
1               5                   10                  15

Asn Arg Val

<210> SEQ ID NO 89
<211> LENGTH: 19
<212> TYPE: PRT
<213> ORGANISM: Artificial
<220> FEATURE:
<223> OTHER INFORMATION: Synthetic Peptide

<400> SEQUENCE: 89

Ala Cys Ile Glu Pro Gly Pro Phe Cys Tyr Ala Asp Pro Tyr Met Cys
1               5                   10                  15

Asn Arg Val

<210> SEQ ID NO 90
<211> LENGTH: 19
<212> TYPE: PRT
<213> ORGANISM: Artificial
<220> FEATURE:
<223> OTHER INFORMATION: Synthetic Peptide

<400> SEQUENCE: 90

Ala Cys Leu Glu Pro Gly Pro Tyr Cys Tyr Ala Asp Pro Tyr Met Cys
1               5                   10                  15

Thr His Leu

<210> SEQ ID NO 91
<211> LENGTH: 17
<212> TYPE: PRT
<213> ORGANISM: Artificial
<220> FEATURE:
<223> OTHER INFORMATION: Synthetic Peptide

<400> SEQUENCE: 91

Ala Cys Leu Pro Pro Gly Pro Tyr Cys Phe Pro Asp Pro Tyr Phe Cys
1               5                   10                  15

Ala

<210> SEQ ID NO 92
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 92

Ala Cys Ile Glu Glu Gly Gln Tyr Cys Phe Ala Asp Pro Tyr Xaa Cys
1               5                   10                  15

Ala

<210> SEQ ID NO 93
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 93

Ala Cys Ala Glu Glu Gly Gln Tyr Cys Phe Ala Asp Pro Tyr Xaa Cys
1               5                   10                  15

Ala

<210> SEQ ID NO 94
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 94

Ala Cys Ile Ala Glu Gly Gln Tyr Cys Phe Ala Asp Pro Tyr Xaa Cys
1               5                   10                  15
Ala

<210> SEQ ID NO 95
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 95

Ala Cys Ile Glu Ala Gly Gln Tyr Cys Phe Ala Asp Pro Tyr Xaa Cys
1               5                   10                  15
Ala

<210> SEQ ID NO 96
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 96

Ala Cys Ile Glu Glu Ala Gln Tyr Cys Phe Ala Asp Pro Tyr Xaa Cys
1               5                   10                  15
Ala

<210> SEQ ID NO 97
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 97

Ala Cys Ile Glu Glu Gly Ala Tyr Cys Phe Ala Asp Pro Tyr Xaa Cys
1               5                   10                  15
Ala

<210> SEQ ID NO 98
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle -continued

<400> SEQUENCE: 98

Ala Cys Ile Glu Glu Gly Gln Ala Cys Phe Ala Asp Pro Tyr Xaa Cys
1               5                   10                  15
Ala

<210> SEQ ID NO 99
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 99

Ala Cys Ile Glu Glu Gly Gln Tyr Cys Ala Ala Asp Pro Tyr Xaa Cys
1               5                   10                  15
Ala

<210> SEQ ID NO 100
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 100

Ala Cys Ile Glu Glu Gly Gln Tyr Cys Phe Ala Ala Pro Tyr Xaa Cys
1               5                   10                  15
Ala

<210> SEQ ID NO 101
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 101

Ala Cys Ile Glu Glu Gly Gln Tyr Cys Phe Ala Asp Pro Ala Xaa Cys
1               5                   10                  15
Ala

<210> SEQ ID NO 102
<211> LENGTH: 17
<212> TYPE: PRT
<213> ORGANISM: Artificial
<220> FEATURE:
<223> OTHER INFORMATION: Synthetic Peptide

<400> SEQUENCE: 102

Ala Cys Ile Glu Glu Gly Gln Tyr Cys Phe Ala Asp Pro Tyr Ala Cys
1               5                   10                  15
Ala

```
<210> SEQ ID NO 103
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 103

Ala Cys Ala Glu Glu Gly Gln Tyr Cys Phe Ala Asp Pro Tyr Xaa Cys
1               5                   10                  15

Ala

<210> SEQ ID NO 104
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 104

Ala Cys Ile Ala Glu Gly Gln Tyr Cys Phe Ala Asp Pro Tyr Xaa Cys
1               5                   10                  15

Ala

<210> SEQ ID NO 105
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 105

Ala Cys Ile Glu Ala Gly Gln Tyr Cys Phe Ala Asp Pro Tyr Xaa Cys
1               5                   10                  15

Ala

<210> SEQ ID NO 106
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 106

Ala Cys Ile Glu Glu Ala Gln Tyr Cys Phe Ala Asp Pro Tyr Xaa Cys
1               5                   10                  15

Ala

<210> SEQ ID NO 107
```

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 107

Ala Cys Ile Glu Glu Gly Ala Tyr Cys Phe Ala Asp Pro Tyr Xaa Cys
1               5                   10                  15
Ala

<210> SEQ ID NO 108
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 108

Ala Cys Ile Glu Glu Gly Gln Ala Cys Phe Ala Asp Pro Tyr Xaa Cys
1               5                   10                  15
Ala

<210> SEQ ID NO 109
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 109

Ala Cys Ile Glu Glu Gly Gln Tyr Cys Ala Ala Asp Pro Tyr Xaa Cys
1               5                   10                  15
Ala

<210> SEQ ID NO 110
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 110

Ala Cys Ile Glu Glu Gly Gln Tyr Cys Phe Ala Asp Pro Tyr Xaa Cys
1               5                   10                  15
Ala

<210> SEQ ID NO 111
<211> LENGTH: 17
<212> TYPE: PRT
<213> ORGANISM: Artificial
```

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 111

Ala Cys Ile Glu Glu Gly Gln Tyr Cys Phe Ala Ala Pro Tyr Xaa Cys
1               5                   10                  15
Ala

<210> SEQ ID NO 112
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 112

Ala Cys Ile Glu Glu Gly Gln Tyr Cys Phe Ala Asp Ala Tyr Xaa Cys
1               5                   10                  15
Ala

<210> SEQ ID NO 113
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 113

Ala Cys Ile Glu Glu Gly Gln Tyr Cys Phe Ala Asp Pro Ala Xaa Cys
1               5                   10                  15
Ala

<210> SEQ ID NO 114
<211> LENGTH: 17
<212> TYPE: PRT
<213> ORGANISM: Artificial
<220> FEATURE:
<223> OTHER INFORMATION: Synthetic Peptide

<400> SEQUENCE: 114

Ala Cys Ile Glu Glu Gly Gln Tyr Cys Phe Ala Asp Pro Tyr Ala Cys
1               5                   10                  15
Ala

<210> SEQ ID NO 115
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
```

```
<400> SEQUENCE: 115

Ala Cys Leu Glu Glu Gly Gln Tyr Cys Phe Ala Asp Pro Tyr Xaa Cys
1               5                   10                  15
Ala

<210> SEQ ID NO 116
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Nle
<220> FEATURE:
<221> NAME/KEY: X
<222> LOCATION: (15)..(15)
<223> OTHER INFORMATION: X represents Nle

<400> SEQUENCE: 116

Ala Cys Xaa Glu Glu Gly Gln Tyr Cys Phe Ala Asp Pro Tyr Xaa Cys
1               5                   10                  15
Ala

<210> SEQ ID NO 117
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Chg
<220> FEATURE:
<221> NAME/KEY: X
<222> LOCATION: (15)..(15)
<223> OTHER INFORMATION: X represents Nle

<400> SEQUENCE: 117

Ala Cys Xaa Glu Glu Gly Gln Tyr Cys Phe Ala Asp Pro Tyr Xaa Cys
1               5                   10                  15
Ala

<210> SEQ ID NO 118
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Cha
<220> FEATURE:
<221> NAME/KEY: X
<222> LOCATION: (15)..(15)
<223> OTHER INFORMATION: X represents Nle

<400> SEQUENCE: 118

Ala Cys Xaa Glu Glu Gly Gln Tyr Cys Phe Ala Asp Pro Tyr Xaa Cys
1               5                   10                  15
Ala

<210> SEQ ID NO 119
<211> LENGTH: 17
```

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 119

Ala Cys Ile Pro Glu Gly Gln Tyr Cys Phe Ala Asp Pro Tyr Xaa Cys
1               5                   10                  15

Ala

<210> SEQ ID NO 120
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 120

Ala Cys Ile Asp Glu Gly Gln Tyr Cys Phe Ala Asp Pro Tyr Xaa Cys
1               5                   10                  15

Ala

<210> SEQ ID NO 121
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Aad
<220> FEATURE:
<221> NAME/KEY: X
<222> LOCATION: (15)..(15)
<223> OTHER INFORMATION: X represents Nle

<400> SEQUENCE: 121

Ala Cys Ile Xaa Glu Gly Gln Tyr Cys Phe Ala Asp Pro Tyr Xaa Cys
1               5                   10                  15

Ala

<210> SEQ ID NO 122
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Api
<220> FEATURE:
<221> NAME/KEY: X
<222> LOCATION: (15)..(15)
<223> OTHER INFORMATION: X represents Nle
```

<400> SEQUENCE: 122

Ala Cys Ile Xaa Glu Gly Gln Tyr Cys Phe Ala Asp Pro Tyr Xaa Cys
1               5                   10                  15

Ala

<210> SEQ ID NO 123
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 123

Ala Cys Ile Glu Pro Gly Gln Tyr Cys Phe Ala Asp Pro Tyr Xaa Cys
1               5                   10                  15

Ala

<210> SEQ ID NO 124
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 124

Ala Cys Ile Glu Asp Gly Gln Tyr Cys Phe Ala Asp Pro Tyr Xaa Cys
1               5                   10                  15

Ala

<210> SEQ ID NO 125
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)
<223> OTHER INFORMATION: X represents Aad
<220> FEATURE:
<221> NAME/KEY: X
<222> LOCATION: (15)..(15)
<223> OTHER INFORMATION: X represents Nle

<400> SEQUENCE: 125

Ala Cys Ile Glu Xaa Gly Gln Tyr Cys Phe Ala Asp Pro Tyr Xaa Cys
1               5                   10                  15

Ala

<210> SEQ ID NO 126
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)

<223> OTHER INFORMATION: X represents Api
<220> FEATURE:
<221> NAME/KEY: X
<222> LOCATION: (15)..(15)
<223> OTHER INFORMATION: X represents Nle

<400> SEQUENCE: 126

Ala Cys Ile Glu Xaa Gly Gln Tyr Cys Phe Ala Asp Pro Tyr Xaa Cys
1               5                   10                  15
Ala

<210> SEQ ID NO 127
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Sar
<220> FEATURE:
<221> NAME/KEY: X
<222> LOCATION: (15)..(15)
<223> OTHER INFORMATION: X represents Nle

<400> SEQUENCE: 127

Ala Cys Ile Glu Glu Xaa Gln Tyr Cys Phe Ala Asp Pro Tyr Xaa Cys
1               5                   10                  15
Ala

<210> SEQ ID NO 128
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 128

Ala Cys Ile Glu Glu Lys Gln Tyr Cys Phe Ala Asp Pro Tyr Xaa Cys
1               5                   10                  15
Ala

<210> SEQ ID NO 129
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 129

Ala Cys Ile Glu Glu Phe Gln Tyr Cys Phe Ala Asp Pro Tyr Xaa Cys
1               5                   10                  15
Ala

<210> SEQ ID NO 130
<211> LENGTH: 17
<212> TYPE: PRT
<213> ORGANISM: Artificial

```
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 130

Ala Cys Ile Glu Glu Glu Gln Tyr Cys Phe Ala Asp Pro Tyr Xaa Cys
1               5                   10                  15
Ala

<210> SEQ ID NO 131
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 131

Ala Cys Ile Glu Glu Gln Gln Tyr Cys Phe Ala Asp Pro Tyr Xaa Cys
1               5                   10                  15
Ala

<210> SEQ ID NO 132
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 132

Ala Cys Ile Glu Glu Leu Gln Tyr Cys Phe Ala Asp Pro Tyr Xaa Cys
1               5                   10                  15
Ala

<210> SEQ ID NO 133
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 133

Ala Cys Ile Glu Glu Ser Gln Tyr Cys Phe Ala Asp Pro Tyr Xaa Cys
1               5                   10                  15
Ala

<210> SEQ ID NO 134
<211> LENGTH: 17
<212> TYPE: PRT
<213> ORGANISM: Artificial
<220> FEATURE:
<223> OTHER INFORMATION: Synthetic Peptide
<220> FEATURE:
```

```
<221> NAME/KEY: X
<222> LOCATION: (6)..(6)
<223> OTHER INFORMATION: X represents MeD-Ala
<220> FEATURE:
<221> NAME/KEY: X
<222> LOCATION: (15)..(15)
<223> OTHER INFORMATION: X represents Nle

<400> SEQUENCE: 134

Ala Cys Ile Glu Glu Xaa Gln Tyr Cys Phe Ala Asp Pro Tyr Xaa Cys
1               5                   10                  15

Ala

<210> SEQ ID NO 135
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Aib
<220> FEATURE:
<221> NAME/KEY: X
<222> LOCATION: (15)..(15)
<223> OTHER INFORMATION: X represents Nle

<400> SEQUENCE: 135

Ala Cys Ile Glu Glu Xaa Gln Tyr Cys Phe Ala Asp Pro Tyr Xaa Cys
1               5                   10                  15

Ala

<210> SEQ ID NO 136
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 136

Ala Cys Ile Glu Glu Gly Pro Tyr Cys Phe Ala Asp Pro Tyr Xaa Cys
1               5                   10                  15

Ala

<210> SEQ ID NO 137
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 137

Ala Cys Ile Glu Glu Gly Gln Phe Cys Phe Ala Asp Pro Tyr Xaa Cys
1               5                   10                  15

Ala

<210> SEQ ID NO 138
<211> LENGTH: 17
```

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2MePhe
<220> FEATURE:
<221> NAME/KEY: X
<222> LOCATION: (15)..(15)
<223> OTHER INFORMATION: X represents Nle

<400> SEQUENCE: 138

Ala Cys Ile Glu Glu Gly Gln Xaa Cys Phe Ala Asp Pro Tyr Xaa Cys
1               5                   10                  15
Ala

<210> SEQ ID NO 139
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 3MePhe
<220> FEATURE:
<221> NAME/KEY: X
<222> LOCATION: (15)..(15)
<223> OTHER INFORMATION: X represents Nle

<400> SEQUENCE: 139

Ala Cys Ile Glu Glu Gly Gln Xaa Cys Phe Ala Asp Pro Tyr Xaa Cys
1               5                   10                  15
Ala

<210> SEQ ID NO 140
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 140

Ala Cys Ile Glu Glu Gly Gln Xaa Cys Phe Ala Asp Pro Tyr Xaa Cys
1               5                   10                  15
Ala

<210> SEQ ID NO 141
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
```

```
<222> LOCATION: (15)..(15)
<223> OTHER INFORMATION: X represents Nle

<400> SEQUENCE: 141

Ala Cys Ile Glu Glu Gly Gln Xaa Cys Phe Ala Asp Pro Tyr Xaa Cys
1               5                   10                  15
Ala

<210> SEQ ID NO 142
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 142

Ala Cys Ile Glu Glu Gly Gln Xaa Cys Phe Ala Asp Pro Tyr Xaa Cys
1               5                   10                  15
Ala

<210> SEQ ID NO 143
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represnets MePhe
<220> FEATURE:
<221> NAME/KEY: X
<222> LOCATION: (15)..(15)
<223> OTHER INFORMATION: X represnets Nle

<400> SEQUENCE: 143

Ala Cys Ile Glu Glu Gly Gln Tyr Cys Xaa Ala Asp Pro Tyr Xaa Cys
1               5                   10                  15
Ala

<210> SEQ ID NO 144
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents MePhe
<220> FEATURE:
<221> NAME/KEY: X
<222> LOCATION: (15)..(15)
<223> OTHER INFORMATION: X represents Nle

<400> SEQUENCE: 144

Ala Cys Ile Glu Glu Gly Gln Tyr Cys Xaa Ala Asp Pro Tyr Xaa Cys
1               5                   10                  15
Ala
```

```
<210> SEQ ID NO 145
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents MePhe
<220> FEATURE:
<221> NAME/KEY: X
<222> LOCATION: (15)..(15)
<223> OTHER INFORMATION: X represents Nle

<400> SEQUENCE: 145

Ala Cys Ile Glu Glu Gly Gln Tyr Cys Xaa Ala Asp Pro Tyr Xaa Cys
1               5                   10                  15
Ala

<210> SEQ ID NO 146
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents PheG
<220> FEATURE:
<221> NAME/KEY: X
<222> LOCATION: (15)..(15)
<223> OTHER INFORMATION: X represents Nle

<400> SEQUENCE: 146

Ala Cys Ile Glu Glu Gly Gln Tyr Cys Xaa Ala Asp Pro Tyr Xaa Cys
1               5                   10                  15
Ala

<210> SEQ ID NO 147
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 147

Ala Cys Ile Glu Glu Gly Gln Tyr Cys Xaa Ala Asp Pro Tyr Xaa Cys
1               5                   10                  15
Ala

<210> SEQ ID NO 148
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
```

<223> OTHER INFORMATION: X represents Nle

<400> SEQUENCE: 148

Ala Cys Ile Glu Glu Gly Gln Tyr Cys Phe Gly Asp Pro Tyr Xaa Cys
1               5                   10                  15
Ala

<210> SEQ ID NO 149
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 149

Ala Cys Ile Glu Glu Gly Gln Tyr Cys Phe Ser Asp Pro Tyr Xaa Cys
1               5                   10                  15
Ala

<210> SEQ ID NO 150
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 150

Ala Cys Ile Glu Glu Gly Gln Tyr Cys Phe Pro Asp Pro Tyr Xaa Cys
1               5                   10                  15
Ala

<210> SEQ ID NO 151
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 151

Ala Cys Ile Glu Glu Gly Gln Tyr Cys Phe Ala Asn Pro Tyr Xaa Cys
1               5                   10                  15
Ala

<210> SEQ ID NO 152
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Pip
<220> FEATURE:
<221> NAME/KEY: X

```
<222> LOCATION: (15)..(15)
<223> OTHER INFORMATION: X represents Nle

<400> SEQUENCE: 152

Ala

```
<210> SEQ ID NO 156
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 156

Ala Cys Xaa Glu Glu Gly Gln Tyr Cys Phe Ala Asp Pro Tyr Xaa Cys
1               5                   10                  15
Ala

<210> SEQ ID NO 157
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents HLeu
<220> FEATURE:
<221> NAME/KEY: X
<222> LOCATION: (15)..(15)
<223> OTHER INFORMATION: X represents Nle

<400> SEQUENCE: 157

Ala Cys Xaa Glu Glu Gly Gln Tyr Cys Phe Ala Asp Pro Tyr Xaa Cys
1               5                   10                  15
Ala

<210> SEQ ID NO 158
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 158

Ala Cys Ile Glu Glu Gly Gln Xaa Cys Phe Ala Asp Pro Tyr Xaa Cys
1               5                   10                  15
Ala

<210> SEQ ID NO 159
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
```

```
<223> OTHER INFORMATION: X represents FPhe
<220> FEATURE:
<221> NAME/KEY: X
<222> LOCATION: (15)..(15)
<223> OTHER INFORMATION: X represents Nle

<400> SEQUENCE: 159

Ala Cys Ile Glu Glu Gly Gln Tyr Cys Xaa Ala Asp Pro Tyr Xaa Cys
1               5                   10                  15
Ala

<210> SEQ ID NO 160
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents CF3G
<220> FEATURE:
<221> NAME/KEY: X
<222> LOCATION: (15)..(15)
<223> OTHER INFORMATION: X represents Nle

<400> SEQUENCE: 160

Ala Cys Ile Glu Glu Gly Gln Tyr Cys Phe Xaa Asp Pro Tyr Xaa Cys
1               5                   10                  15
Ala

<210> SEQ ID NO 161
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents pCoPhe
<220> FEATURE:
<221> NAME/KEY: X
<222> LOCATION: (15)..(15)
<223> OTHER INFORMATION: X represents Nle

<400> SEQUENCE: 161

Ala Cys Ile Glu Glu Gly Gln Tyr Cys Phe Ala Asp Pro Xaa Xaa Cys
1               5                   10                  15
Ala

<210> SEQ ID NO 162
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents pCaPhe
<220> FEATURE:
<221> NAME/KEY: X
<222> LOCATION: (15)..(15)
<223> OTHER INFORMATION: X represents Nle
```

<400> SEQUENCE: 162

Ala Cys Ile Glu Glu Gly Gln Tyr Cys Phe Ala Asp Pro Xaa Xaa Cys
1               5                   10                  15
Ala

<210> SEQ ID NO 163
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 163

Ala Cys Ile Glu Glu Gly Gln Tyr Cys Phe Ala Asp Pro Gln Xaa Cys
1               5                   10                  15
Ala

<210> SEQ ID NO 164
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 2MePhe
<220> FEATURE:
<221> NAME/KEY: X
<222> LOCATION: (15)..(15)
<223> OTHER INFORMATION: X represents Nle

<400> SEQUENCE: 164

Ala Cys Ile Glu Glu Gly Gln Tyr Cys Phe Ala Asp Pro Xaa Xaa Cys
1               5                   10                  15
Ala

<210> SEQ ID NO 165
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 3MePhe
<220> FEATURE:
<221> NAME/KEY: X
<222> LOCATION: (15)..(15)
<223> OTHER INFORMATION: X represents Nle

<400> SEQUENCE: 165

Ala Cys Ile Glu Glu Gly Gln Tyr Cys Phe Ala Asp Pro Xaa Xaa Cys
1               5                   10                  15
Ala

<210> SEQ ID NO 166
<211> LENGTH: 17
<212> TYPE: PRT
<213> ORGANISM: Artificial
<220> FEATURE:

```
<223> OTHER INFORMATION: Synthetic Peptide
<220> FEATURE:
<221> NAME/KEY: X
<222> LOCATION: (14)..(14)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 166

Ala Cys Ile Glu Glu Gly Gln Tyr Cys Phe Ala Asp Pro Xaa Xaa Cys
1               5                   10                  15
Ala

<210> SEQ ID NO 167
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Cit
<220> FEATURE:
<221> NAME/KEY: X
<222> LOCATION: (15)..(15)
<223> OTHER INFORMATION: X represents Nle

<400> SEQUENCE: 167

Ala Cys Ile Glu Glu Gly Gln Tyr Cys Phe Ala Asp Pro Xaa Xaa Cys
1               5                   10                  15
Ala

<210> SEQ ID NO 168
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 168

Ala Cys Ile Glu Glu Gly Gln Tyr Cys Phe Ala Asp Pro Xaa Xaa Cys
1               5                   10                  15
Ala

<210> SEQ ID NO 169
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents tBuAla
```

-continued

<400> SEQUENCE: 169

Ala Cys Ile Glu Glu Gly Gln Tyr Cys Phe Ala Asp Pro Tyr Xaa Cys
1               5                   10                  15

Ala

<210> SEQ ID NO 170
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents HLeu

<400> SEQUENCE: 170

Ala Cys Ile Glu Glu Gly Gln Tyr Cys Phe Ala Asp Pro Tyr Xaa Cys
1               5                   10                  15

Ala

<210> SEQ ID NO 171
<211> LENGTH: 17
<212> TYPE: PRT
<213> ORGANISM: Artificial
<220> FEATURE:
<223> OTHER INFORMATION: Synthetic Peptide

<400> SEQUENCE: 171

Ala Cys Ile Glu Glu Gly Gln Tyr Cys Phe Ala Asp Pro Tyr Ile Cys
1               5                   10                  15

Ala

<210> SEQ ID NO 172
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Cha

<400> SEQUENCE: 172

Ala Cys Ile Glu Glu Gly Gln Tyr Cys Phe Ala Asp Pro Tyr Xaa Cys
1               5                   10                  15

Ala

<210> SEQ ID NO 173
<211> LENGTH: 17
<212> TYPE: PRT
<213> ORGANISM: Artificial
<220> FEATURE:
<223> OTHER INFORMATION: Synthetic Peptide

<400> SEQUENCE: 173

Ala Cys Ile Glu Glu Gly Gln Tyr Cys Phe Ala Asp Pro Tyr Phe Cys
1               5                   10                  15

Ala

<210> SEQ ID NO 174
<211> LENGTH: 17

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 2MePhe

<400> SEQUENCE: 174

Ala Cys Ile Glu Glu Gly Gln Tyr Cys Phe Ala Asp Pro Tyr Xaa Cys
1               5                   10                  15
Ala

<210> SEQ ID NO 175
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 3MePhe

<400> SEQUENCE: 175

Ala Cys Ile Glu Glu Gly Gln Tyr Cys Phe Ala Asp Pro Tyr Xaa Cys
1               5                   10                  15
Ala

<210> SEQ ID NO 176
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents 4MePhe

<400> SEQUENCE: 176

Ala Cys Ile Glu Glu Gly Gln Tyr Cys Phe Ala Asp Pro Tyr Xaa Cys
1               5                   10                  15
Ala

<210> SEQ ID NO 177
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Pen
<220> FEATURE:
<221> NAME/KEY: X
<222> LOCATION: (15)..(15)
<223> OTHER INFORMATION: X represents Nle

<400> SEQUENCE: 177

Ala Xaa Ile Glu Glu Gly Gln Tyr Cys Phe Ala Asp Pro Tyr Xaa Cys
1               5                   10                  15
Ala

<210> SEQ ID NO 178
```

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (9)..(9)
<223> OTHER INFORMATION: X represents Pen
<220> FEATURE:
<221> NAME/KEY: X
<222> LOCATION: (15)..(15)
<223> OTHER INFORMATION: X represents Nle

<400> SEQUENCE: 178

Ala Cys Ile Glu Glu Gly Gln Tyr Xaa Phe Ala Asp Pro Tyr Xaa Cys
1               5                   10                  15

Ala

<210> SEQ ID NO 179
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
<220> FEATURE:
<221> NAME/KEY: X
<222> LOCATION: (16)..(16)
<223> OTHER INFORMATION: X represents Pen

<400> SEQUENCE: 179

Ala Cys Ile Glu Glu Gly Gln Tyr Cys Phe Ala Asp Pro Tyr Xaa Xaa
1               5                   10                  15

Ala

<210> SEQ ID NO 180
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents HCys
<220> FEATURE:
<221> NAME/KEY: X
<222> LOCATION: (15)..(15)
<223> OTHER INFORMATION: X represents Nle

<400> SEQUENCE: 180

Ala Xaa Ile Glu Glu Gly Gln Tyr Cys Phe Ala Asp Pro Tyr Xaa Cys
1               5                   10                  15

Ala

<210> SEQ ID NO 181
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (9)..(9)
<223> OTHER INFORMATION: X represents HCys
<220> FEATURE:
```

```
<221> NAME/KEY: X
<222> LOCATION: (15)..(15)
<223> OTHER INFORMATION: X represents Nle

<400> SEQUENCE: 181

Ala Cys Ile Glu Glu Gly Gln Tyr Xaa Phe Ala Asp Pro Tyr Xaa Cys
1               5                   10                  15
Ala

<210> SEQ ID NO 182
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
<220> FEATURE:
<221> NAME/KEY: X
<222> LOCATION: (16)..(16)
<223> OTHER INFORMATION: X represents HCys

<400> SEQUENCE: 182

Ala Cys Ile Glu Glu Gly Gln Tyr Cys Phe Ala Asp Pro Tyr Xaa Xaa
1               5                   10                  15
Ala

<210> SEQ ID NO 183
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 3FPhe
<220> FEATURE:
<221> NAME/KEY: X
<222> LOCATION: (15)..(15)
<223> OTHER INFORMATION: X represents Nle

<400> SEQUENCE: 183

Ala Cys Ile Glu Glu Gly Gln Tyr Cys Xaa Ala Asp Pro Tyr Xaa Cys
1               5                   10                  15
Ala

<210> SEQ ID NO 184
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents TetraZ
<220> FEATURE:
<221> NAME/KEY: X
<222> LOCATION: (15)..(15)
<223> OTHER INFORMATION: X represents Nle

<400> SEQUENCE: 184

Ala Cys Ile Xaa Glu Gly Gln Tyr Cys Phe Ala Asp Pro Tyr Xaa Cys
1               5                   10                  15
Ala
```

```
<210> SEQ ID NO 185
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (12)..(12)
<223> OTHER INFORMATION: X represents TetraZ
<220> FEATURE:
<221> NAME/KEY: X
<222> LOCATION: (15)..(15)
<223> OTHER INFORMATION: X represents Nle

<400> SEQUENCE: 185

Ala Cys Ile Glu Glu Gly Gln Tyr Cys Phe Ala Xaa Pro Tyr Xaa Cys
1               5                   10                  15
Ala

<210> SEQ ID NO 186
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents HGln
<220> FEATURE:
<221> NAME/KEY: X
<222> LOCATION: (15)..(15)
<223> OTHER INFORMATION: X represents Nle

<400> SEQUENCE: 186

Ala Cys Ile Glu Glu Gly Gln Tyr Cys Phe Ala Asp Pro Xaa Xaa Cys
1               5                   10                  15
Ala

<210> SEQ ID NO 187
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Ahp
<220> FEATURE:
<221> NAME/KEY: X
<222> LOCATION: (15)..(15)
<223> OTHER INFORMATION: X represents Nle

<400> SEQUENCE: 187

Ala Cys Xaa Glu Glu Gly Gln Tyr Cys Phe Ala Asp Pro Tyr Xaa Cys
1               5                   10                  15
Ala

<210> SEQ ID NO 188
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
```

```
<222> LOCATION: (15)..(15)
<223> OTHER INFORMATION: X represents Ahp

<400> SEQUENCE: 188

Ala Cys Ile Glu Glu Gly Gln Tyr Cys Phe Ala Asp Pro Tyr Xaa Cys
1               5                   10                  15
Ala

<210> SEQ ID NO 189
<211> LENGTH: 17
<212> TYPE: PRT
<213> ORGANISM: Artificial
<220> FEATURE:
<223> OTHER INFORMATION: Synthetic Peptide

<400> SEQUENCE: 189

Ala Cys Ile Glu Glu Gly Gln Tyr Cys Phe Ala Asp Pro Tyr Met Cys
1               5                   10                  15
Ala

<210> SEQ ID NO 190
<211> LENGTH: 19
<212> TYPE: PRT
<213> ORGANISM: Artificial
<220> FEATURE:
<223> OTHER INFORMATION: Synthetic Peptide

<400> SEQUENCE: 190

His Glu His Cys Ile Glu Glu Gly Gln Tyr Cys Tyr Ala Asp Pro Tyr
1               5                   10                  15
Met Cys Ala

<210> SEQ ID NO 191
<211> LENGTH: 17
<212> TYPE: PRT
<213> ORGANISM: Artificial
<220> FEATURE:
<223> OTHER INFORMATION: Synthetic Peptide

<400> SEQUENCE: 191

Ala Cys Ile Glu Glu Gly Gln Tyr Cys Phe Ala Asp Pro Tyr Leu Cys
1               5                   10                  15
Ala

<210> SEQ ID NO 192
<211> LENGTH: 17
<212> TYPE: PRT
<213> ORGANISM: Artificial
<220> FEATURE:
<223> OTHER INFORMATION: Synthetic Peptide

<400> SEQUENCE: 192

Ala Cys Leu Pro Pro Gly Pro Tyr Cys Phe Pro Asp Pro Tyr Phe Cys
1               5                   10                  15
Ala

<210> SEQ ID NO 193
<211> LENGTH: 15
<212> TYPE: PRT
<213> ORGANISM: Artificial
<220> FEATURE:
<223> OTHER INFORMATION: Synthetic Peptide
```

<400> SEQUENCE: 193

Cys Ile Glu Glu Gly Gln Tyr Cys Phe Ala Asp Pro Tyr Met Cys
1               5                   10                  15

<210> SEQ ID NO 194
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (14)..(14)
<223> OTHER INFORMATION: X represents Nle
<220> FEATURE:
<221> NAME/KEY: X
<222> LOCATION: (16)..(16)
<223> OTHER INFORMATION: X represents Dap

<400> SEQUENCE: 194

Cys Ile Glu Glu Gly Gln Tyr Cys Phe Ala Asp Pro Tyr Xaa Cys Xaa
1               5                   10                  15

<210> SEQ ID NO 195
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 195

Ala Cys Ile Pro Glu Phe Gln Tyr Cys Phe Ala Asp Pro Tyr Xaa Cys
1               5                   10                  15
Ala

<210> SEQ ID NO 196
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 196

Ala Cys Ile Pro Glu Phe Pro Tyr Cys Phe Ala Asp Pro Tyr Xaa Cys
1               5                   10                  15
Ala

<210> SEQ ID NO 197
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 197

Ala Cys Ile Glu Glu Phe Pro Tyr Cys Phe Ala Asp Pro Tyr Xaa Cys
1               5                   10                  15

Ala

<210> SEQ ID NO 198
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 198

Ala Cys Ile Pro Glu Gly Pro Tyr Cys Phe Ala Asp Pro Tyr Xaa Cys
1               5                   10                  15

Ala

<210> SEQ ID NO 199
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 199

Ala Cys Xaa Pro Glu Phe Pro Xaa Cys Xaa Ala Asp Pro Tyr Xaa Cys
1               5                   10                  15

Ala

<210> SEQ ID NO 200
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X

```
<222> LOCATION: (15)..(15)
<223> OTHER INFORMATION: X represents Nle

<400> SEQUENCE: 200

Ala Cys Xaa Pro Glu Phe Gln Xaa Cys Xaa Ala Asp Pro Tyr Xaa Cys
1               5                   10                  15

Ala

<210> SEQ ID NO 201
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 201

Ala Cys Xaa Glu Glu Phe Pro Xaa Cys Xaa Ala Asp Pro Tyr Xaa Cys
1               5                   10                  15

Ala

<210> SEQ ID NO 202
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (10)..(10)
<223> OTHER INFORMATION: X represents 4FPhe
<220> FEATURE:
<221> NAME/KEY: X
<222> LOCATION: (15)..(15)
<223> OTHER INFORMATION: X represents Nle

<400> SEQUENCE: 202

Ala Cys Xaa Glu Glu Phe Gln Xaa Cys Xaa Ala Asp Pro Tyr Xaa Cys
1               5                   10                  15

Ala

<210> SEQ ID NO 203
<211> LENGTH: 17
<212> TYPE: PRT
<213> ORGANISM: Artificial
<220> FEATURE:
<223> OTHER INFORMATION: Synthetic Peptide
```

```
<220> FEATURE:
<221> NAME/KEY: X
<222> LOCATION: (4)..(4)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 203

Ala Cys Ile Xaa Glu Gly Gln Tyr Cys Phe Ala Asp Pro Tyr Xaa Cys
1               5                   10                  15

Ala

<210> SEQ ID NO 204
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 204

Ala Cys Ile Glu Glu Trp Gln Tyr Cys Phe Ala Asp Pro Tyr Xaa Cys
1               5                   10                  15

Ala

<210> SEQ ID NO 205
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Aze
<220> FEATURE:
<221> NAME/KEY: X
<222> LOCATION: (15)..(15)
<223> OTHER INFORMATION: X represents Nle

<400> SEQUENCE: 205

Ala Cys Ile Glu Glu Gly Xaa Tyr Cys Phe Ala Asp Pro Tyr Xaa Cys
1               5                   10                  15

Ala

<210> SEQ ID NO 206
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Pip
<220> FEATURE:
<221> NAME/KEY: X
<222> LOCATION: (15)..(15)
<223> OTHER INFORMATION: X represents Nle
```

```
<400> SEQUENCE: 206

Ala Cys Ile Glu Glu Gly Xaa Tyr Cys Phe Ala Asp Pro Tyr Xaa Cys
1               5                   10                  15
Ala

<210> SEQ ID NO 207
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2Nal
<220> FEATURE:
<221> NAME/KEY: X
<222> LOCATION: (15)..(15)
<223> OTHER INFORMATION: X represents Nle

<400> SEQUENCE: 207

Ala Cys Ile Glu Glu Gly Gln Xaa Cys Phe Ala Asp Pro Tyr Xaa Cys
1               5                   10                  15
Ala

<210> SEQ ID NO 208
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MeOPhe
<220> FEATURE:
<221> NAME/KEY: X
<222> LOCATION: (15)..(15)
<223> OTHER INFORMATION: X represents Nle

<400> SEQUENCE: 208

Ala Cys Ile Glu Glu Gly Gln Xaa Cys Phe Ala Asp Pro Tyr Xaa Cys
1               5                   10                  15
Ala

<210> SEQ ID NO 209
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 209

Ala Cys Ile Glu Glu Gly Gln Tyr Cys Tyr Ala Asp Pro Tyr Xaa Cys
1               5                   10                  15
Ala

<210> SEQ ID NO 210
<211> LENGTH: 17
<212> TYPE: PRT
<213> ORGANISM: Artificial
<220> FEATURE:
```

```
<223> OTHER INFORMATION: Synthetic Peptide
<220> FEATURE:
<221> NAME/KEY: X
<222> LOCATION: (13)..(13)
<223> OTHER INFORMATION: X represents Aze
<220> FEATURE:
<221> NAME/KEY: X
<222> LOCATION: (15)..(15)
<223> OTHER INFORMATION: X represents Nle

<400> SEQUENCE: 210

Ala Cys Ile Glu Glu Gly Gln Tyr Cys Phe Ala Asp Xaa Tyr Xaa Cys
1               5                   10                  15
Ala

<210> SEQ ID NO 211
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Hse(Me)

<400> SEQUENCE: 211

Ala Cys Ile Glu Glu Gly Gln Tyr Cys Phe Ala Asp Pro Tyr Xaa Cys
1               5                   10                  15
Ala

<210> SEQ ID NO 212
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents NMeIle
<220> FEATURE:
<221> NAME/KEY: X
<222> LOCATION: (15)..(15)
<223> OTHER INFORMATION: X represents Nle

<400> SEQUENCE: 212

Ala Cys Xaa Glu Glu Gly Gln Tyr Cys Phe Ala Asp Pro Tyr Xaa Cys
1               5                   10                  15
Ala

<210> SEQ ID NO 213
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Aze
<220> FEATURE:
<221> NAME/KEY: X
<222> LOCATION: (15)..(15)
<223> OTHER INFORMATION: X represents Nle
```

```
<400> SEQUENCE: 213

Ala Cys Ile Xaa Glu Gly Gln Tyr Cys Phe Ala Asp Pro Tyr Xaa Cys
1               5                   10                  15

Ala

<210> SEQ ID NO 214
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Pip
<220> FEATURE:
<221> NAME/KEY: X
<222> LOCATION: (15)..(15)
<223> OTHER INFORMATION: X represents Nle

<400> SEQUENCE: 214

Ala Cys Ile Xaa Glu Gly Gln Tyr Cys Phe Ala Asp Pro Tyr Xaa Cys
1               5                   10                  15

Ala

<210> SEQ ID NO 215
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents NMeGlu
<220> FEATURE:
<221> NAME/KEY: X
<222> LOCATION: (15)..(15)
<223> OTHER INFORMATION: X represents Nle

<400> SEQUENCE: 215

Ala Cys Ile Xaa Glu Gly Gln Tyr Cys Phe Ala Asp Pro Tyr Xaa Cys
1               5                   10                  15

Ala

<210> SEQ ID NO 216
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (5)..(5)
<223> OTHER INFORMATION: X represents NMeGlu
<220> FEATURE:
<221> NAME/KEY: X
<222> LOCATION: (15)..(15)
<223> OTHER INFORMATION: X represents Nle

<400> SEQUENCE: 216

Ala Cys Ile Glu Xaa Gly Gln Tyr Cys Phe Ala Asp Pro Tyr Xaa Cys
1               5                   10                  15

Ala

<210> SEQ ID NO 217
```

-continued

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 217

Ala Cys Ile Glu Glu Asp Gln Tyr Cys Phe Ala Asp Pro Tyr Xaa Cys
1               5                   10                  15
Ala

<210> SEQ ID NO 218
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents NMeAla
<220> FEATURE:
<221> NAME/KEY: X
<222> LOCATION: (15)..(15)
<223> OTHER INFORMATION: X represents Nle

<400> SEQUENCE: 218

Ala Cys Ile Glu Glu Gly Xaa Tyr Cys Phe Ala Asp Pro Tyr Xaa Cys
1               5                   10                  15
Ala

<210> SEQ ID NO 219
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents NMeTyr
<220> FEATURE:
<221> NAME/KEY: X
<222> LOCATION: (15)..(15)
<223> OTHER INFORMATION: X represents Nle

<400> SEQUENCE: 219

Ala Cys Ile Glu Glu Gly Gln Xaa Cys Phe Ala Asp Pro Tyr Xaa Cys
1               5                   10                  15
Ala

<210> SEQ ID NO 220
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents HPhe
<220> FEATURE:
<221> NAME/KEY: X
<222> LOCATION: (15)..(15)
<223> OTHER INFORMATION: X represents Nle
```

```
<400> SEQUENCE: 220

Ala Cys Ile Glu Glu Gly Gln Xaa Cys Phe Ala Asp Pro Tyr Xaa Cys
1               5                   10                  15

Ala

<210> SEQ ID NO 221
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 2Pal
<220> FEATURE:
<221> NAME/KEY: X
<222> LOCATION: (15)..(15)
<223> OTHER INFORMATION: X represents Nle

<400> SEQUENCE: 221

Ala Cys Ile Glu Glu Gly Gln Xaa Cys Phe Ala Asp Pro Tyr Xaa Cys
1               5                   10                  15

Ala

<210> SEQ ID NO 222
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 3Pal
<220> FEATURE:
<221> NAME/KEY: X
<222> LOCATION: (15)..(15)
<223> OTHER INFORMATION: X represents Nle

<400> SEQUENCE: 222

Ala Cys Ile Glu Glu Gly Gln Xaa Cys Phe Ala Asp Pro Tyr Xaa Cys
1               5                   10                  15

Ala

<210> SEQ ID NO 223
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4,4-BPA
<220> FEATURE:
<221> NAME/KEY: X
<222> LOCATION: (15)..(15)
<223> OTHER INFORMATION: X represents Nle

<400> SEQUENCE: 223

Ala Cys Ile Glu Glu Gly Gln Xaa Cys Phe Ala Asp Pro Tyr Xaa Cys
1               5                   10                  15

Ala

<210> SEQ ID NO 224
<211> LENGTH: 17
```

```
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents HPhe
<220> FEATURE:
<221> NAME/KEY: X
<222> LOCATION: (15)..(15)
<223> OTHER INFORMATION: X represents Nle

<400> SEQUENCE: 224

Ala Cys Ile Glu Glu Gly Gln Tyr Cys Xaa Ala Asp Pro Tyr Xaa Cys
1               5                   10                  15

Ala

<210> SEQ ID NO 225
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 2Pal
<220> FEATURE:
<221> NAME/KEY: X
<222> LOCATION: (15)..(15)
<223> OTHER INFORMATION: X represents Nle

<400> SEQUENCE: 225

Ala Cys Ile Glu Glu Gly Gln Tyr Cys Xaa Ala Asp Pro Tyr Xaa Cys
1               5                   10                  15

Ala

<210> SEQ ID NO 226
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 3Pal
<220> FEATURE:
<221> NAME/KEY: X
<222> LOCATION: (15)..(15)
<223> OTHER INFORMATION: X represents Nle

<400> SEQUENCE: 226

Ala Cys Ile Glu Glu Gly Gln Tyr Cys Xaa Ala Asp Pro Tyr Xaa Cys
1               5                   10                  15

Ala

<210> SEQ ID NO 227
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4Pal
<220> FEATURE:
<221> NAME/KEY: X
```

```
<222> LOCATION: (15)..(15)
<223> OTHER INFORMATION: X represents Nle

<400> SEQUENCE: 227

Ala Cys Ile Glu Glu Gly Gln Tyr Cys Xaa Ala Asp Pro Tyr Xaa Cys
1               5                   10                  15
Ala

<210> SEQ ID NO 228
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4,4-BPA
<220> FEATURE:
<221> NAME/KEY: X
<222> LOCATION: (15)..(15)
<223> OTHER INFORMATION: X represents Nle

<400> SEQUENCE: 228

Ala Cys Ile Glu Glu Gly Gln Tyr Cys Xaa Ala Asp Pro Tyr Xaa Cys
1               5                   10                  15
Ala

<210> SEQ ID NO 229
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 1Nal
<220> FEATURE:
<221> NAME/KEY: X
<222> LOCATION: (15)..(15)
<223> OTHER INFORMATION: X represents Nle

<400> SEQUENCE: 229

Ala Cys Ile Glu Glu Gly Gln Tyr Cys Xaa Ala Asp Pro Tyr Xaa Cys
1               5                   10                  15
Ala

<210> SEQ ID NO 230
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4tBuPhe
<220> FEATURE:
<221> NAME/KEY: X
<222> LOCATION: (15)..(15)
<223> OTHER INFORMATION: X represents Nle

<400> SEQUENCE: 230

Ala Cys Ile Glu Glu Gly Gln Tyr Cys Xaa Ala Asp Pro Tyr Xaa Cys
1               5                   10                  15
Ala
```

```
<210> SEQ ID NO 231
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents NMeAla
<220> FEATURE:
<221> NAME/KEY: X
<222> LOCATION: (15)..(15)
<223> OTHER INFORMATION: X represents Nle

<400> SEQUENCE: 231

Ala Cys Ile Glu Glu Gly Gln Tyr Cys Phe Xaa Asp Pro Tyr Xaa Cys
1               5                   10                  15
Ala

<210> SEQ ID NO 232
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents 5,5-dmP
<220> FEATURE:
<221> NAME/KEY: X
<222> LOCATION: (15)..(15)
<223> OTHER INFORMATION: X represents Nle

<400> SEQUENCE: 232

Ala Cys Ile Glu Glu Gly Xaa Tyr Cys Phe Ala Asp Pro Tyr Xaa Cys
1               5                   10                  15
Ala

<210> SEQ ID NO 233
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 233

Ala Cys Ile Glu Glu Gly Gln Tyr Cys Phe Ala Asp Xaa Tyr Xaa Cys
1               5                   10                  15
Ala

<210> SEQ ID NO 234
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
```

```
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 234

Ala Cys Ile Glu Glu Gly Xaa Tyr Cys Phe Ala Asp Pro Tyr Xaa Cys
1               5                   10                  15
Ala

<210> SEQ ID NO 235
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 235

Ala Cys Ile Glu Glu Gly Gln Tyr Cys Phe Ala Asp Xaa Tyr Xaa Cys
1               5                   10                  15
Ala

<210> SEQ ID NO 236
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Oic
<220> FEATURE:
<221> NAME/KEY: X
<222> LOCATION: (15)..(15)
<223> OTHER INFORMATION: X represents Nle

<400> SEQUENCE: 236

Ala Cys Ile Xaa Glu Gly Gln Tyr Cys Phe Ala Asp Pro Tyr Xaa Cys
1               5                   10                  15
Ala

<210> SEQ ID NO 237
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (13)..(13)
<223> OTHER INFORMATION: X represents Oxa
<220> FEATURE:
<221> NAME/KEY: X
<222> LOCATION: (15)..(15)
<223> OTHER INFORMATION: X represents Nle
```

```
<400> SEQUENCE: 237

Ala Cys Ile Glu Glu Gly Gln Tyr Cys Phe Ala Asp Xaa Tyr Xaa Cys
1               5                   10                  15
Ala

<210> SEQ ID NO 238
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (4)..(4)
<223> OTHER INFORMATION: X represents Oxa
<220> FEATURE:
<221> NAME/KEY: X
<222> LOCATION: (15)..(15)
<223> OTHER INFORMATION: X represents Nle

<400> SEQUENCE: 238

Ala Cys Ile Xaa Glu Gly Gln Tyr Cys Phe Ala Asp Pro Tyr Xaa Cys
1               5                   10                  15
Ala

<210> SEQ ID NO 239
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Oxa
<220> FEATURE:
<221> NAME/KEY: X
<222> LOCATION: (15)..(15)
<223> OTHER INFORMATION: X represents Nle

<400> SEQUENCE: 239

Ala Cys Ile Glu Glu Gly Xaa Tyr Cys Phe Ala Asp Pro Tyr Xaa Cys
1               5                   10                  15
Ala

<210> SEQ ID NO 240
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 240

Ala Cys Ile Pro Glu Gly Pro Tyr Cys Phe Ala Asp Pro Tyr Xaa Cys
1               5                   10                  15
Ala

<210> SEQ ID NO 241
<211> LENGTH: 17
<212> TYPE: PRT
<213> ORGANISM: Artificial
<220> FEATURE:
```

```
<223> OTHER INFORMATION: Synthetic Peptide
<220> FEATURE:
<221> NAME/KEY: X
<222> LOCATION: (7)..(7)
<223> OTHER INFORMATION: X represents HyP
<220> FEATURE:
<221> NAME/KEY: X
<222> LOCATION: (15)..(15)
<223> OTHER INFORMATION: X represents Nle

<400> SEQUENCE: 241

Ala Cys Ile Glu Glu Gly Xaa Tyr Cys Phe Ala Asp Pro Tyr Xaa Cys
1               5                   10                  15

Ala

<210> SEQ ID NO 242
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 242

Ala Cys Ile Pro Glu Ala Pro Tyr Cys Phe Ala Asp Pro Tyr Xaa Cys
1               5                   10                  15

Ala

<210> SEQ ID NO 243
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 243

Ala Cys Xaa Pro Glu Ala Pro Tyr Cys Phe Ala Asp Pro Tyr Xaa Cys
1               5                   10                  15

Ala

<210> SEQ ID NO 244
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 244

Ala Cys Ile Glu Glu Gly Gln Tyr Cys Phe Ala Asp Pro Tyr Xaa Cys
1               5                   10                  15

Ala
```

```
<210> SEQ ID NO 245
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents tBuAla
<220> FEATURE:
<221> NAME/KEY: X
<222> LOCATION: (15)..(15)
<223> OTHER INFORMATION: X represents Nle

<400> SEQUENCE: 245

Ala Cys Xaa Glu Glu Gly Gln Tyr Cys Phe Ala Asp Pro Tyr Xaa Cys
1               5                   10                  15
Ala

<210> SEQ ID NO 246
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Chg
<220> FEATURE:
<221> NAME/KEY: X
<222> LOCATION: (15)..(15)
<223> OTHER INFORMATION: X represents Nle

<400> SEQUENCE: 246

Ala Cys Xaa Glu Glu Gly Gln Tyr Cys Phe Ala Asp Pro Tyr Xaa Cys
1               5                   10                  15
Ala

<210> SEQ ID NO 247
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (3)..(3)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 247

Ala Cys Xaa Glu Glu Gly Gln Tyr Cys Phe Ala Asp Pro Tyr Xaa Cys
1               5                   10                  15
Ala

<210> SEQ ID NO 248
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle
```

<400> SEQUENCE: 248

Ala Cys Ile Pro Glu Gly Gln Tyr Cys Phe Ala Asp Pro Tyr Xaa Cys
1               5                   10                  15

Ala

<210> SEQ ID NO 249
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 249

Ala Cys Ile Gln Glu Gly Gln Tyr Cys Phe Ala Asp Pro Tyr Xaa Cys
1               5                   10                  15

Ala

<210> SEQ ID NO 250
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 250

Ala Cys Ile Glu Pro Gly Gln Tyr Cys Phe Ala Asp Pro Tyr Xaa Cys
1               5                   10                  15

Ala

<210> SEQ ID NO 251
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 251

Ala Cys Ile Glu Gln Gly Gln Tyr Cys Phe Ala Asp Pro Tyr Xaa Cys
1               5                   10                  15

Ala

<210> SEQ ID NO 252
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

```
<400> SEQUENCE: 252

Ala Cys Ile Glu Glu Phe Gln Tyr Cys Phe Ala Asp Pro Tyr Xaa Cys
1               5                   10                  15

Ala

<210> SEQ ID NO 253
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 253

Ala Cys Ile Glu Glu Ala Gln Tyr Cys Phe Ala Asp Pro Tyr Xaa Cys
1               5                   10                  15

Ala

<210> SEQ ID NO 254
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (6)..(6)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 254

Ala Cys Ile Glu Glu Xaa Gln Tyr Cys Phe Ala Asp Pro Tyr Xaa Cys
1               5                   10                  15

Ala

<210> SEQ ID NO 255
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Nle

<400> SEQUENCE: 255

Ala Cys Ile Glu Glu Gly Ala Tyr Cys Phe Ala Asp Pro Tyr Xaa Cys
1               5                   10                  15

Ala

<210> SEQ ID NO 256
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
```

```
<223> OTHER INFORMATION: X represents Aib
<220> FEATURE:
<221> NAME/KEY: X
<222> LOCATION: (15)..(15)
<223> OTHER INFORMATION: X represents Nle

<400> SEQUENCE: 256

Ala Cys Ile Glu Glu Gly Xaa Tyr Cys Phe Ala Asp Pro Tyr Xaa Cys
1               5                   10                  15

Ala

<210> SEQ ID NO 257
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (7)..(7)
<223> OTHER INFORMATION: X represents Ac5c
<220> FEATURE:
<221> NAME/KEY: X
<222> LOCATION: (15)..(15)
<223> OTHER INFORMATION: X represents Nle

<400> SEQUENCE: 257

Ala Cys Ile Glu Glu Gly Xaa Tyr Cys Phe Ala Asp Pro Tyr Xaa Cys
1               5                   10                  15

Ala

<210> SEQ ID NO 258
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represents 4MePhe
<220> FEATURE:
<221> NAME/KEY: X
<222> LOCATION: (15)..(15)
<223> OTHER INFORMATION: X represents Nle

<400> SEQUENCE: 258

Ala Cys Ile Glu Glu Gly Gln Xaa Cys Phe Ala Asp Pro Tyr Xaa Cys
1               5                   10                  15

Ala

<210> SEQ ID NO 259
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (8)..(8)
<223> OTHER INFORMATION: X represnets 1Nal
<220> FEATURE:
<221> NAME/KEY: X
<222> LOCATION: (15)..(15)
<223> OTHER INFORMATION: X represnets Nle
```

<400> SEQUENCE: 259

Ala Cys Ile Glu Glu Gly Gln Xaa Cys Phe Ala Asp Pro Tyr Xaa Cys
1               5                   10                  15

Ala

<210> SEQ ID NO 260
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 2Nal
<220> FEATURE:
<221> NAME/KEY: X
<222> LOCATION: (15)..(15)
<223> OTHER INFORMATION: X represents Nle

<400> SEQUENCE: 260

Ala Cys Ile Glu Glu Gly Gln Tyr Cys Xaa Ala Asp Pro Tyr Xaa Cys
1               5                   10                  15

Ala

<210> SEQ ID NO 261
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents NO2Phe
<220> FEATURE:
<221> NAME/KEY: X
<222> LOCATION: (15)..(15)
<223> OTHER INFORMATION: X represents Nle

<400> SEQUENCE: 261

Ala Cys Ile Glu Glu Gly Gln Tyr Cys Xaa Ala Asp Pro Tyr Xaa Cys
1               5                   10                  15

Ala

<210> SEQ ID NO 262
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (10)..(10)
<223> OTHER INFORMATION: X represents 4BrPhe
<220> FEATURE:
<221> NAME/KEY: X
<222> LOCATION: (15)..(15)
<223> OTHER INFORMATION: X represents Nle

<400> SEQUENCE: 262

Ala Cys Ile Glu Glu Gly Gln Tyr Cys Xaa Ala Asp Pro Tyr Xaa Cys
1               5                   10                  15

Ala

<210> SEQ ID NO 263

```
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (11)..(11)
<223> OTHER INFORMATION: X represents Abu
<220> FEATURE:
<221> NAME/KEY: X
<222> LOCATION: (15)..(15)
<223> OTHER INFORMATION: X represents Nle

<400> SEQUENCE: 263

Ala Cys Ile Glu Glu Gly Gln Tyr Cys Phe Xaa Asp Pro Tyr Xaa Cys
 1               5                  10                  15
Ala

<210> SEQ ID NO 264
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (15)..(15)
<223> OTHER INFORMATION: X represents Ahp

<400> SEQUENCE: 264

Ala Cys Ile Glu Glu Gly Gln Tyr Cys Phe Ala Asp Pro Tyr Xaa Cys
 1               5                  10                  15
Ala

<210> SEQ ID NO 265
<211> LENGTH: 17
<212> TYPE: PRT
<213> ORGANISM: Artificial
<220> FEATURE:
<223> OTHER INFORMATION: Synthetic Peptide

<400> SEQUENCE: 265

Ala Cys Ile Glu Glu Gly Gln Tyr Cys Phe Ala Asp Pro Tyr Met Cys
 1               5                  10                  15
Ala

<210> SEQ ID NO 266
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Ile, tBuAla or Chg
<220> FEATURE:
<221> NAME/KEY: X
<222> LOCATION: (3)..(3)
<223> OTHER INFORMATION: X represents Glu, Pro, Asp, Lys, Aad, HyP or
    Oxa
<220> FEATURE:
<221> NAME/KEY: X
<222> LOCATION: (4)..(4)
<223> OTHER INFORMATION: X represents Glu, Lys or Aad
<220> FEATURE:
<221> NAME/KEY: X
```

```
<222> LOCATION: (5)..(5)
<223> OTHER INFORMATION: X represents Gly, D-Lys, D-Ala, L-Ala, D-Phe,
      D-Glu, D-Gln, D-Leu, D-Ser or D-Trp
<220> FEATURE:
<221> NAME/KEY: X
<222> LOCATION: (6)..(6)
<223> OTHER INFORMATION: X represents Gln, Lys, Ala, Pro, 5,5-dmP, Oic,
      Oxa, HyP, Aib or Ac5c
<220> FEATURE:
<221> NAME/KEY: X
<222> LOCATION: (7)..(7)
<223> OTHER INFORMATION: X represents Tyr, Phe, 3MeF, 4MeF, 4FF, 2Nal,
      4MeOPhe or 4,4BPA
<220> FEATURE:
<221> NAME/KEY: X
<222> LOCATION: (9)..(9)
<223> OTHER INFORMATION: X represents Phe, Lys, 4MeF, 4FF, 2FPhe, 4FPhe,
      4Pal, 4,4BPA, 4tBuPhe, NO2Phe or 4BrPhe
<220> FEATURE:
<221> NAME/KEY: X
<222> LOCATION: (10)..(10)
<223> OTHER INFORMATION: X represents Ala or Lys
<220> FEATURE:
<221> NAME/KEY: X
<222> LOCATION: (12)..(12)
<223> OTHER INFORMATION: X represents Pro or Lys
<220> FEATURE:
<221> NAME/KEY: X
<222> LOCATION: (13)..(13)
<223> OTHER INFORMATION: X represents Tyr or Lys
<220> FEATURE:
<221> NAME/KEY: X
<222> LOCATION: (14)..(14)
<223> OTHER INFORMATION: X represents Met, Lys, Nle, HLeu or Ahp

<400> SEQUENCE: 266

Cys Xaa Xaa Xaa Xaa Xaa Xaa Cys Xaa Xaa Asp Xaa Xaa Xaa Cys
1               5                   10                  15

<210> SEQ ID NO 267
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: X
<222> LOCATION: (2)..(2)
<223> OTHER INFORMATION: X represents Ile or tBuAla
<220> FEATURE:
<221> NAME/KEY: X
<222> LOCATION: (3)..(3)
<223> OTHER INFORMATION: X represents Lys, Glu or Pro
<220> FEATURE:
<221> NAME/KEY: X
<222> LOCATION: (4)..(4)
<223> OTHER INFORMATION: X represents Glu or D-Lys
<220> FEATURE:
<221> NAME/KEY: X
<222> LOCATION: (5)..(5)
<223> OTHER INFORMATION: X represents Gly, D-Lys, D-Phe or D-Ala
<220> FEATURE:
<221> NAME/KEY: X
<222> LOCATION: (6)..(6)
<223> OTHER INFORMATION: X represents Gln, Lys or Pro
<220> FEATURE:
<221> NAME/KEY: X
<222> LOCATION: (7)..(7)
<223> OTHER INFORMATION: X represents Tyr or 4MePhe
<220> FEATURE:
<221> NAME/KEY: X
<222> LOCATION: (9)..(9)
<223> OTHER INFORMATION: X represents Phe or 4FPhe
<220> FEATURE:
<221> NAME/KEY: X
<222> LOCATION: (14)..(14)
<223> OTHER INFORMATION: X represents Met or Nle
```

<400> SEQUENCE: 267

Cys Xaa Xaa Xaa Xaa Xaa Xaa Cys Xaa Ala Asp Pro Tyr Xaa Cys
1               5                   10                  15

The invention claimed is:

1. A method of treating a cancer or inflammation by inhibiting CD137 in a patient, the method comprising administering to the patient a peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, which comprises an amino acid sequence selected from:

$C_i$-I/L/N/I/V-E/D/P/S-P/E/A-G-P/Q-Y/F-$C_{ii}$-Y-A-D-P-Y/N/I-M/L/Y-$C_{iii}$; (SEQ ID NO: 41)

$C_i$-I-E-E-G-Q-Y-$C_{ii}$-X1-X2-D-X3-Y/Q/M-X4-$C_{iii}$; (SEQ ID NO: 20)

$C_i$-D-I-G-P-P-Y-$C_{ii}$-Y-R/A-D-M/P-Y-M-$C_{iii}$; (SEQ ID NO: 21)

$C_i$-D-E-W-G-L-F/Y-$C_{ii}$-I/F-P/A-H-S/P-D-$C_{iii}$; (SEQ ID NO: 22)
and $C_i$LEPGPFCHYADPYM$C_{iii}$; (SEQ ID NO: 19)

wherein $X_1$-$X_4$ represent any amino acid residue and $C_i$, $C_{ii}$ and $C_{iii}$ represent first, second and third cysteine residues, respectively or a pharmaceutically acceptable salt thereof.

2. The method of claim 1, wherein the peptide ligand of $C_i$-I-E-E-G-Q-Y-$C_{ii}$-$X_1$-$X_2$-D-$X_3$-Y/Q-$X_4$-$C_{iii}$ (SEQ ID NO: 20) comprises an amino acid sequence selected from any one of SEQ ID NOS: 1-14:

$C_i$EEGQYC$_{ii}$YRDMYMC$_{iii}$; (SEQ ID NO: 1)

$C_i$EEGQYC$_{ii}$YADPYMC$_{iii}$; (SEQ ID NO: 2)

$C_i$EEGQYC$_{ii}$YADPYYC$_{iii}$; (SEQ ID NO: 3)

$C_i$EEGQYC$_{ii}$YDPYYC$_{iii}$; (SEQ ID NO: 4)

$C_i$EEGQYC$_{ii}$FADPYMC$_{iii}$; (SEQ ID NO: 5)

$C_i$EEGQYC$_{ii}$YADHQLC$_{iii}$; (SEQ ID NO: 6)

$C_i$EEGQYC$_{ii}$HADPYYC$_{iii}$; (SEQ ID NO: 7)

$C_{iii}$EEGQYC$_{ii}$HADPYFC$_{iii}$; (SEQ ID NO: 8)

$C_i$EEGQYC$_{ii}$YADHYMC$_{iii}$; (SEQ ID NO: 9)

$C_i$EEGQYC$_{ii}$YADPYLC$_{iii}$; (SEQ ID NO: 10)

$C_i$EEGQYC$_{ii}$YSDPYLC$_{iii}$; (SEQ ID NO: 11)

$C_i$EEGQYC$_{ii}$FADPYLC$_{iii}$; (SEQ ID NO: 12)

$C_i$EEGQYC$_{ii}$HADPYMC$_{iii}$; (SEQ ID NO: 13)
and;

$C_i$EEGQYC$_{ii}$HADPQMC$_{iii}$; (SEQ ID NO: 14)

or
an amino acid sequence selected from:
A-(SEQ ID NO: 1)-A (herein referred to as 74-01-00-N004);
A-(SEQ ID NO: 2)-A (herein referred to as 74-01-01-N001);
A-(SEQ ID NO: 3)-A (herein referred to as 74-01-02-N001);
A-(SEQ ID NO: 4)-A (herein referred to as 74-01-03-N001);
A-(SEQ ID NO: 5)-A (herein referred to as 74-01-04-N001);
A-(SEQ ID NO: 6)-A (herein referred to as 74-01-05-N001);
A-(SEQ ID NO: 7)-A (herein referred to as 74-01-06-N001);
A-(SEQ ID NO: 8)-A (herein referred to as 74-01-07-N001);
A-(SEQ ID NO: 9)-A (herein referred to as 74-01-08-N001);
A-(SEQ ID NO: 10)-A (herein referred to as 74-01-09-N001);
A-(SEQ ID NO: 10)-SVG (herein referred to as 74-01-09-T03-N002);
A-(SEQ ID NO: 11)-A (herein referred to as 74-01-10-N001);
A-(SEQ ID NO: 12)-A (herein referred to as 74-01-11-N001);
A-(SEQ ID NO: 13)-A (herein referred to as 74-01-13-N001); and
A-(SEQ ID NO: 14)-A (herein referred to as 74-01-14-N001).

3. The method of claim 1, wherein the peptide ligand $C_i$-D-I-G-P-P-Y-$C_{ii}$-Y-R/A-D-M/P-Y-M-$C_{iii}$ (SEQ ID NO: 21) comprises an amino acid sequence selected from:

$C_i$DIGPPYC$_{ii}$YRDMYMC$_{iii}$; (SEQ ID NO: 15)
and $C_i$DIGPPYC$_{ii}$YADPYMC$_{iii}$; (SEQ ID NO: 16)

or an amino acid sequence selected from:
- A-(SEQ ID NO: 15)-A (herein referred to as 74-01-16-N001); and
- A-(SEQ ID NO: 16)-A (herein referred to as 74-01-17-N001).

4. The method of claim 1, wherein the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

$C_i$DEWGLFC$_{ii}$IPHSDC$_{iii}$; (SEQ ID NO: 17)
and
$C_i$DEWGLYC$_{ii}$FAHPDC$_{iii}$; (SEQ ID NO: 18)

or an amino acid sequence selected from:
- Ac-A-(SEQ ID NO: 17)-A (herein referred to as 74-02-00-N004); and
- A-(SEQ ID NO: 18)-A (herein referred to as 74-02-01-N001).

5. The method of claim 1, wherein the peptide ligand of $C_i$IEPGPFC$_{ii}$YADPYMC$_{iii}$ (SEQ ID NO: 19) comprises an amino acid sequence of:
- A-(SEQ ID NO: 19)-NRV (herein referred to as 74-19-00-T01-N002).

6. The method of claim 1, wherein the molecular scaffold is 1,1',1"-(1,3,5-triazinane-1,3,5-triyl)triprop-2-en-1-one (TATA).

7. The method of claim 1, wherein the pharmaceutically acceptable salt is selected from the free acid or the sodium, potassium, calcium, or ammonium salt.

8. The method of claim 1, wherein the CD137 is human CD137.

9. A method of treating a cancer or inflammation by inhibiting CD137 in a patient, the method comprising administering to the patient a peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, which comprises an amino acid sequence selected from:

$C_i$IEEGQYC$_{ii}$FADPY(Nle)C$_{iii}$; (SEQ ID NO: 23)

$C_i$IKEGQYC$_{ii}$FADPY(Nle)C$_{iii}$; (SEQ ID NO: 24)

$C_i$IEKGQYC$_{ii}$FADPY(Nle)C$_{iii}$; (SEQ ID NO: 25)

$C_i$IEE(D-K)QYC$_{ii}$FADPY(Nle)C$_{iii}$; (SEQ ID NO: 26)

$C_i$IEEGKYC$_{ii}$FADPY(Nle)C$_{iii}$; (SEQ ID NO: 27)

$C_i$IEEGQYC$_{ii}$KADPY(Nle)C$_{iii}$; (SEQ ID NO: 28)

$C_i$IEEGQYC$_{ii}$FADKY(Nle)C$_{iii}$; (SEQ ID NO: 29)

$C_i$IEEGQYC$_{ii}$FADPYKC$_{iii}$; (SEQ ID NO: 30)

$C_i$LPPGQYC$_{ii}$FPDLLLC$_{iii}$; (SEQ ID NO: 40; 74-22-00)

A-C$_i$IEEGQYC$_{ii}$FADPY(Nle)C$_{iii}$-A; (SEQ ID NO: 31; BCY3814)

Ac-A-C$_i$IEEGQYC$_{ii}$FADPY(Nle)C$_{iii}$-Dap; (SEQ ID NO: 32; BCY7732)

Ac-A-C$_i$IKEGQYC$_{ii}$FADPY(Nle)C$_{iii}$-A; (SEQ ID NO: 33; BCY7733)

Ac-A-C$_i$IEKGQYC$_{ii}$FADPY(Nle)C$_{iii}$-A; (SEQ ID NO: 34; BCY7734)

Ac-A-C$_i$IEE(D-K)QYC$_{ii}$FADPY(Nle)C$_{iii}$-A; (SEQ ID NO: 35; BCY7735)

Ac-A-C$_i$IEEGKYC$_{ii}$FADPY(Nle)C$_{iii}$-A; (SEQ ID NO: 36; BCY7736)

Ac-A-C$_i$IEEGQYC$_{ii}$KADPY(Nle)C$_{iii}$-A; (SEQ ID NO: 37; BCY7737)

Ac-A-C$_i$IEEGQYC$_{ii}$FADKY(Nle)C$_{iii}$-A; (SEQ ID NO: 38; BCY7738)

and

Ac-A-C$_i$IEEGQYCIIFADPYKC$_{iii}$-A; (SEQ ID NO: 39; BCY7739)

or an amino acid sequence selected from:

| Peptide Number | SEQ ID NO: | Sequence |
| --- | --- | --- |
| BCY633 | 42 | [B-Ala]-Sar5-ACIEEGQYCYRDMYMCA |
| BCY634 | 43 | [Ac]ACIEEGQYCYRDMYMCA-Sar6-K(Fl) |
| BCY636 | 44 | ACIEEGQYCYADPYMCA-Sar6-K(Fl) |
| BCY635 | 45 | [B-Ala]-Sar5-ACIEEGQYCYADPYMCA |
| BCY638 | 46 | ACIEEGQYCYADPYYCASar6-K |
| BCY637 | 47 | [B-Ala]-Sar5-ACIEEGQYCYADPYYCA |
| BCY639 | 48 | ACIEEGQYCYSDPYYCA-Sar6-K |
| BCY640 | 49 | ACIEEGQYCFADPYMCA-Sar6-K |
| BCY641 | 50 | G-Sar5-ACIEEGQYCFADPYMCA |
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7244 | 57 | Ac-CIEEGQYCK(Peg12)ADPYMC |
| BCY7245 | 58 | Ac-CIEEGQYCFK(Peg12)DPYMC |
| BCY7247 | 60 | Ac-CIEEGQYCFADK(Peg12)YMC |
| BCY7248 | 61 | Ac-CIEEGQYCFADPK(Peg12)MC |
| BCY7249 | 62 | Ac-CIEEGQYCFADPYK(Peg12)C |

| Peptide Number | SEQ ID NO: | Sequence |
|---|---|---|
| BCY7416 | 63 | [Ac]CIEE[dK(PEG12Fl)]QYCFADPY[Nle]C |
| BCY7519 | 64 | ACIEEGQYCFADPY[Nle]CA |
| BCY7520 | 65 | [Peg12]-ACIEEGQYCFADPY[Nle]CA |
| BCY642 | 66 | ACIEEGQYCYADHQLCA-Sar6-K |
| BCY643 | 67 | ACIEEGQYCHADPYYCA-Sar6-K |
| BCY644 | 68 | ACIEEGQYCHADPYFCA-Sar6-K |
| BCY645 | 69 | ACIEEGQYCYADHYMCA-Sar6-K |
| BCY646 | 70 | ACIEEGQYCYADPYLCA-Sar6-K |
| BCY647 | 71 | ACIEEGQYCYADPYLCSVG-Sar6-K |
| BCY648 | 72 | (Fl)G-Sar5-ACIEEGQYCYADPYLCSVG |
| BCY649 | 73 | ACIEEGQYCYSDPYLCA-Sar6-K |
| BCY650 | 74 | ACIEEGQYCFADPYLCA-Sar6-K |
| BCY652 | 75 | ACIEEGQYCHADPYMCA-Sar6-K |
| BCY653 | 76 | ACIEEGQYCHADPQMCA-Sar6-K |
| BCY655 | 77 | ACDIGPPYCYRDMYMCA-Sar6-K |
| BCY656 | 78 | ADIGPPYCYADPYMCA-Sar6-K |
| BCY7251 | 79 | ACLDPGPFCFADPYMCA-Sar6-K |
| BCY7253 | 80 | ACLDEGPYCFADPYFCA-Sar6-K |
| BCY7255 | 81 | ACINEGPYCFADPYMCA-Sar6-K |
| BCY7257 | 82 | ACIEQGPFCFADPYMCA-Sar6-K |
| BCY7259 | 83 | ACVEEGPFCFADPYYCA-Sar6-K |
| BCY7261 | 84 | ACLDEGPFCFSDPYMCA-Sar6-K |
| BCY657 | 85 | [B-Ala]-Sar5-ACDEWGLFCIPHSDCA |
| BCY659 | 86 | ACDEWGLYCFAHPDCA-Sar6-K |
| BCY7119 | 87 | ACLDPGPYCYADPYMCTFH-Sar6-K |
| BCY660 | 88 | ACIEPGPFCYADPYMCNRV-Sar6-K |
| BCY661 | 89 | G-Sar5-ACIEPGPFCYADPYMCNRV |
| BCY7120 | 90 | ACLEPGPYCYADPYMCTHL-Sar6-K |
| BCY7122 | 91 | ACLPPGPYCFPDPYFCA-Sar6-K |
| BCY7151 | 92 | [PEG3]-ACIEEGQYCFADPY[Nle]CA |
| BCY7152 | 115 | [PEG3]-ACLEEGQYCFADPY[Nle]CA |
| BCY7153 | 116 | [PEG3]-AC[Nle]EEGQYCFADPY[Nle]CA |
| BCY7154 | 117 | [PEG3]-AC-Chg-EEGQYCFADPY[Nle]CA |
| BCY7155 | 118 | [PEG3]-AC-Cha-EEGQYCFADPY[Nle]CA |
| BCY7156 | 119 | [PEG3]-ACEPEGQYCFADPY[Nle]CA |
| BCY7157 | 120 | [PEG3]-ACIDEGQYCFADPY[Nle]CA |
| BCY7158 | 121 | [PEG3]-ACI-Aad-EGQYCFADPY[Nle]CA |
| BCY7159 | 122 | [PEG3]-ACI-Api-EGQYCFADPY[Nle]CA |
| BCY7160 | 123 | [PEG3]-ACIEPGQYCFADPY[Nle]CA |
| BCY7161 | 124 | [PEG3]-ACIEDGQYCFADPY[Nle]CA |
| BCY7162 | 125 | [PEG3]-ACIE-Aad-GQYCFADPY[Nle]CA |
| BCY7163 | 126 | [PEG3]-ACIE-Api-GQYCFADPY[Nle]CA |
| BCY7164 | 127 | [PEG3]-ACIEE-Sar-QYCFADPY[Nle]CA |
| BCY7165 | 128 | [PEG3]-ACIEE-DLys-QYCFADPY[Nle]CA |
| BCY7166 | 129 | [PEG3]-ACIEE-DPhe-QYCFADPY[Nle]CA |
| BCY7167 | 130 | [PEG3]-ACIEE-DGlu-QYCFADPY[Nle]CA |
| BCY7168 | 131 | [PEG3]-ACIEE-DGln-QYCFADPY[Nle]CA |
| BCY7169 | 132 | [PEG3]-ACIEE-DLeu-QYCFADPY[Nle]CA |
| BCY7170 | 133 | [PEG3]-ACIEE-DSer-QYCFADPY[Nle]CA |
| BCY7172 | 134 | [PEG3]-ACIEE-MeDala-QYCFADPY[Nle]CA |
| BCY7173 | 135 | [PEG3]-ACIEE-Aib-QYCFADPY[Nle]CA |
| BCY7174 | 136 | [PEG3]-ACIEEGPYCFADPY[Nle]CA |
| BCY7175 | 137 | [PEG3]-ACIEEGQFCFADPY[Nle]CA |
| BCY7176 | 138 | [PEG3]-ACIEEGQ-2MeF-CFADPY[Nle]CA |
| BCY7177 | 139 | [PEG3]-ACIEEGQ-3MeF-CFADPY[Nle]CA |
| BCY7178 | 140 | [PEG3]-ACIEEGQ-4MeF-CFADPY[Nle]CA |
| BCY7179 | 141 | [PEG3]-ACIEEGQ-4FF-CFADPY[Nle]CA |
| BCY7180 | 142 | [PEG3]-ACIEEGQ-3FF-CFADPY[Nle]CA |

-continued

| Peptide Number | SEQ ID NO: | Sequence |
|---|---|---|
| BCY7181 | 143 | [PEG3]-ACIEEGQYC-2MeF-ADPY[Nle]CA |
| BCY7182 | 144 | [PEG3]-ACIEEGQYC-3MeF-ADPY[Nle]CA |
| BCY7183 | 145 | [PEG3]-ACIEEGQYC-4MeF-ADPY[Nle]CA |
| BCY7184 | 146 | [PEG3]-ACIEEGQYC-PheG-ADPY[Nle]CA |
| BCY7185 | 147 | [PEG3]-ACIEEGQYC-4FF-ADPY[Nle]CA |
| BCY7186 | 148 | [PEG3]-ACIEEGQYCFGDPY[Nle]CA |
| BCY7187 | 149 | [PEG3]-ACIEEGQYCFSDPY[Nle]CA |
| BCY7188 | 150 | [PEG3]-ACIEEGQYCFPDPY[Nle]CA |
| BCY7189 | 151 | [PEG3]-ACIEEGQYCFANPY[Nle]CA |
| BCY7190 | 152 | [PEG3]-ACIEEGQYCFAD-Pip-Y[Nle]CA |
| BCY7191 | 153 | [PEG3]-ACIEEGQYCFAD-MeAla-Y[Nle]CA |
| BCY7192 | 154 | [PEG3]-ACIEEGQYCFAD-Sar-Y[Nle]CA |
| BCY7193 | 155 | [PEG3]-ACIEEGQYCFAD-Aib-Y[Nle]CA |
| BCY7195 | 156 | [PEG3]AC[tBuAla]EEGQYCFADPY[Nle]CA |
| BCY7196 | 157 | [PEG3]AC[HLeu]EEGQYCFADPY[Nle]CA |
| BCY7197 | 158 | [PEG3]ACIEEGQ[2FPhe]CFADPY[Nle]CA |
| BCY7198 | 159 | [PEG3]ACIEEGQYC[2FPhe]ADPY[Nle]CA |
| BCY7199 | 160 | [PEG3]ACIEEGQYCF[CF3G]DPY[Nle]CA |
| BCY7200 | 161 | [PEG3]ACIEEGQYCFADP[pCoPhe][Nle]CA |
| BCY7201 | 162 | [PEG3]ACIEEGQYCFADP[pCaPhe][Nle]CA |
| BCY7202 | 163 | [PEG3]ACEEEGQYCFADPQ[Nle]CA |
| BCY7205 | 164 | [PEG3]ACIEEGQYCFADP[2MePhe][Nle]CA |
| BCY7206 | 165 | [PEG3]ACIEEGQYCFADP[3MePhe][Nle]CA |
| BCY7207 | 166 | [PEG3]ACIEEGQYCFADP[4MePhe][Nle]CA |
| BCY7208 | 167 | [PEG3]ACIEEGQYCFADP[Cit][Nle]CA |
| BCY7209 | 168 | [PEG3]ACIEEGQYCFADP[4FPhe][Nle]CA |
| BCY7210 | 169 | [PEG3]ACIEEGQYCFADPY[tBuAla]CA |
| BCY7211 | 170 | [PEG3]ACIEEGQYCFADPY[HLeu]CA |
| BCY7212 | 171 | [PEG3]ACIEEGQYCFADPYICA |
| BCY7213 | 172 | [PEG3]ACIEEGQYCFADPY[Cha]CA |
| BCY7214 | 173 | [PEG3]ACIEEGQYCFADPYFCA |
| BCY7215 | 174 | [PEG3]ACIEEGQYCFADPY[2MePhe]CA |
| BCY7216 | 175 | [PEG3]ACIEEGQYCFADPY[3MePhe]CA |
| BCY7217 | 176 | [PEG3]ACIEEGQYCFADPY[4MePhe]CA |
| BCY7218 | 177 | [PEG3]A[Pen]IEEGQYCFADPY[Nle]CA |
| BCY7219 | 178 | [PEG3]ACIEEGQY[Pen]FADPY[Nle]CA |
| BCY7220 | 179 | [PEG3]ACIEEGQYCFADPY[Nle][Pen]A |
| BCY7221 | 180 | [PEG3]A[HCys]IEEGQYCFADPY[Nle]CA |
| BCY7222 | 181 | [PEG3]ACIEEGQY[HCys]FADPY[Nle]CA |
| BCY7223 | 182 | [PEG3]ACIEEGQYCFADPY[Nle][HCys]A |
| BCY7224 | 183 | [PEG3]ACIEEGQYC[3FPhe]ADPY[Nle]CA |
| BCY7306 | 184 | [PEG3]-ACI[TetraZ]EGQYCFADPY[Nle]CA |
| BCY7308 | 185 | [PEG3]-ACIEEGQYCFA[TetraZ]PY[Nle]CA |
| BCY7309 | 186 | [PEG3]-ACIEEGQYCFADP[HGln][Nle]CA |
| BCY7310 | 187 | [PEG3]-AC[Ahp]EEGQYCFADPY[Nle]CA |
| BCY7311 | 188 | [PEG3]-ACIEEGQYCFADPY[Ahp]CA |
| BCY592 | 189 | ACIEEGQYCFADPYMCA |
| BCY589 | 190 | HEHCIEEGQYCYADPYMCA |
| BCY599 | 191 | ACIEEGQYCFADPYLCA |
| BCY631 | 192 | ACLPPGPYCFPDPYFCA |
| BCY592 | 189 | ACIEEGQYCFADPYMCA |
| BCY593 | 193 | [Ac]CIEEGQYCFADPYMC |
| BCY3814 | 31 | ACIEEGQYCFADPY(Nle)CA |

| Peptide Number | SEQ ID NO: | Sequence |
|---|---|---|
| BCY7527 | 194 | [Ac]CIEEGQYCFADPY[Nle]C[Dap] |
| BCY7768 | 195 | [PEG3]ACIPE[dF]QYCFADPY[Nle]CA |
| BCY7770 | 196 | [PEG3]ACIPE[dF]PYCFADPY[Nle]CA |
| BCY7772 | 197 | [PEG3]ACIEE[dF]PYCFADPY[Nle]CA |
| BCY7773 | 198 | PEG3]ACIPEGPYCFADPY[Nle]CA |
| BCY7774 | 199 | [PEG3]AC[tBuAla]PE[dF]P[4MePhe]C[4FPhe]ADPY[Nle]CA |
| BCY7775 | 200 | [PEG3]AC[tBuAla]PE[dF]Q[4MePhe]C[4FPhe]ADPY[Nle]CA |
| BCY7776 | 201 | [PEG3]AC[tBuAla]EE[dF]P[4MePhe]C[4FPhe]ADPY[Nle]CA |
| BCY7777 | 202 | [PEG3]AC[tBuAla]EE[dF]Q[4MePhe]C[4FPhe]ADPY[Nle]CA |
| BCY7796 | 203 | [PEG3]ACI[HyP]EGQYCFADPY[Nle]CA |
| BCY7798 | 204 | [PEG3]ACIEE[dW]QYCFADPY[Nle]CA |
| BCY7799 | 205 | [PEG3]ACIEEG[Aze]YCFADPY[Nle]CA |
| BCY7800 | 206 | [PEG3]ACIEEG[Pip]YCFADPY[Nle]CA |
| BCY7801 | 207 | [PEG3]ACIEEGQ[2Nal]CFADPY[Nle]CA |
| BCY7802 | 208 | [PEG3]ACIEEGQ[4MeoPhe]CFADPY[Nle]CA |
| BCY7803 | 209 | [PEG3]ACIEEGQYCYADPY[Nle]CA |
| BCY7804 | 210 | [PEG3]ACIEEGQYCFAD[Aze]Y[Nle]CA |
| BCY7806 | 211 | [PEG3]ACIEEGQYCFADPY[Hse(Me)]CA |
| BCY7923 | 212 | [Ac]AC[NMeIle]EEGQYCFADPY[Nle]CA |
| BCY7924 | 213 | [Ac]ACI[Aze]EGQYCFADPY[Nle]CA |
| BCY7925 | 214 | [Ac]ACI[Pip]EGQYCFADPY[Nle]CA |
| BCY7926 | 215 | [Ac]ACI[NMeGlu]EGQYCFADPY[Nle]CA |
| BCY7927 | 216 | [Ac]ACIE[NMeGlu]GQYCFADPY[Nle]CA |
| BCY7928 | 217 | [Ac]ACIEE[dD]QYCFADPY[Nle]CA |
| BCY7929 | 218 | [Ac]ACEEEG[NMeAla]YCFADPY[Nle]CA |
| BCY7930 | 219 | [Ac]ACIEEGQ[NMeTyr]CFADPY[Nle]CA |
| BCY7931 | 220 | [Ac]ACIEEGQ[HPhe]CFADPY[Nle]CA |
| BCY7933 | 221 | [Ac]ACIEEGQ[2Pal]CFADPY[Nle]CA |
| BCY7934 | 222 | [Ac]ACIEEGQ[3Pal]CFADPY[Nle]CA |
| BCY7936 | 223 | [Ac]ACIEEGQ[44BPA]CFADPY[Nle]CA |
| BCY7937 | 224 | [Ac]ACIEEGQYC[HPhe]ADPY[Nle]CA |
| BCY7939 | 225 | [Ac]ACIEEGQYC[2Pal]ADPY[Nle]CA |
| BCY7940 | 226 | [Ac]ACIEEGQYC[3Pal]ADPY[Nle]CA |
| BCY7941 | 227 | [Ac]ACIEEGQYC[4Pal]ADPY[Nle]CA |
| BCY7942 | 228 | [Ac]ACIEEGQYC[44BPA]ADPY[Nle]CA |
| BCY7943 | 229 | [Ac]ACIEEGQYC[1Nal]ADPY[Nle]CA |
| BCY7944 | 230 | [Ac]ACIEEGQYC[4tBuPhe]ADPY[Nle]CA |
| BCY7945 | 231 | [Ac]ACIEEGQYCF[NMeAla]DPY[Nle]CA |
| BCY7950 | 232 | [Ac]ACIEEG[55DMP]YCFADPY[Nle]CA |
| BCY7953 | 233 | [Ac]ACIEEGQYCFAD[HyP]Y[Nle]CA |
| BCY7954 | 234 | [Ac]ACIEEG[Oic]YCFADPY[Nle]CA |
| BCY7955 | 235 | [Ac]ACIEEGQYCFAD[Oic]Y[Nle]CA |
| BCY7956 | 236 | [Ac]ACI[Oic]EGQYCFADPY[Nle]CA |
| BCY7957 | 237 | [Ac]ACIEEGQYCFAD[Oxa]Y[Nle]CA |
| BCY7958 | 238 | [Ac]ACI[Oxa]EGQYCFADPY[Nle]CA |
| BCY7959 | 239 | [Ac]ACIEEG[Oxa]YCFADPY[Nle]CA |
| BCY7960 | 240 | [Ac]ACIPEGPYCFADPY[Nle]CA |
| BCY7952 | 241 | [Ac]ACIEEG[HyP]YCFADPY[Nle]CA |

-continued

| Peptide Number | SEQ ID NO: | Sequence |
|---|---|---|
| BCY7961 | 242 | [Ac]ACIPE[dA]PYCFADPY[Nle]CA |
| BCY7965 | 243 | [Ac]AC[tBuAla]PE[dA]PYCFADPY[Nle]CA |
| BCY8217 | 244 | ACIEEGQYCF[dA]DPY[Nle]CA |
| BCY8656 | 245 | [Ac]AC[tBuAla]EEGQYCFADPY[Nle]CA |
| BCY8657 | 246 | [Ac]AC[Chg]EEGQYCFADPY[Nle]CA |
| BCY8658 | 247 | [Ac]AC[AC5C]EEGQYCFADPY[Nle]CA |
| BCY8659 | 248 | [Ac]ACIPEGQYCFADPY[Nle]CA |
| BCY8660 | 249 | [Ac]ACIQEGQYCFADPY[Nle]CA |
| BCY8661 | 250 | [Ac]ACIEPGQYCFADPY[Nle]CA |
| BCY8662 | 251 | [Ac]ACIEQGQYCFADPY[Nle]CA |
| BCY8663 | 252 | [Ac]ACIEE[dF]QYCFADPY[Nle]CA |
| BCY8664 | 253 | [Ac]ACIEE[dA]QYCFADPY[Nle]CA |
| BCY8665 | 254 | [Ac]ACIEE[AC5C]QYCFADPY[Nle]CA |
| BCY7939 | 225 | [Ac]ACIEEGQYC[2Pal]ADPY[Nle]CA |
| BCY7940 | 226 | [Ac]ACIEEGQYC[3Pal]ADPY[Nle]CA |
| BCY7941 | 227 | [Ac]ACIEEGQYC[4Pal]ADPY[Nle]CA |
| BCY7942 | 228 | [Ac]ACIEEGQYC[44BPA]ADPY[Nle]CA |
| BCY7943 | 229 | [Ac]ACIEEGQYC[1Nal]ADPY[Nle]CA |
| BCY7944 | 230 | [Ac]ACIEEGQYC[4tBuPhe]ADPY[Nle]CA |
| BCY7945 | 231 | [Ac]ACIEEGQYCF[NMeAla]DPY[Nle]CA |
| BCY7950 | 232 | [Ac]ACIEEG[55DMP]YCFADPY[Nle]CA |
| BCY7953 | 233 | [Ac]ACIEEGQYCFAD[HyP]Y[Nle]CA |
| BCY7954 | 234 | [Ac]ACIEEG[Oic]YCFADPY[Nle]CA |
| BCY7955 | 235 | [Ac]ACIEEGQYCFAD[Oic]Y[Nle]CA |
| BCY7956 | 236 | [Ac]ACI[Oic]EGQYCFADPY[Nle]CA |

-continued

| Peptide Number | SEQ ID NO: | Sequence |
|---|---|---|
| BCY7957 | 237 | [Ac]ACIEEGQYCFAD[Oxa]Y[Nle]CA |
| BCY7958 | 238 | [Ac]ACI[Oxa]EGQYCFADPY[Nle]CA |
| BCY7959 | 239 | [Ac]ACIEEG[Oxa]YCFADPY[Nle]CA |
| BCY7960 | 240 | [Ac]ACIPEGPYCFADPY[Nle]CA |
| BCY7952 | 241 | [Ac]ACIEEG[HyP]YCFADPY[Nle]CA |
| BCY7961 | 242 | [Ac]ACIPE[dA]PYCFADPY[Nle]CA |
| BCY7965 | 243 | [Ac]AC[tBuAla]PE[dA]PYCFADPY[Nle]CA |
| BCY8217 | 244 | ACIEEGQYCF[dA]DPY[Nle]CA |
| BCY8656 | 245 | [Ac]AC[tBuAla]EEGQYCFADPY[Nle]CA |
| BCY8657 | 246 | [Ac]AC[Chg]EEGQYCFADPY[Nle]CA |
| BCY8658 | 247 | [Ac]AC[AC5C]EEGQYCFADPY[Nle]CA |
| BCY8659 | 248 | [Ac]ACIPEGQYCFADPY[Nle]CA |
| BCY8660 | 249 | [Ac]ACIQEGQYCFADPY[Nle]CA |
| BCY8661 | 250 | [Ac]ACIEPGQYCFADPY[Nle]CA |
| BCY8662 | 251 | [Ac]ACIEQGQYCFADPY[Nle]CA |
| BCY8663 | 252 | [Ac]ACIEE[dF]QYCFADPY[Nle]CA |
| BCY8664 | 253 | [Ac]ACIEE[dA]QYCFADPY[Nle]CA |
| BCY8665 | 254 | [Ac]ACIEE[AC5C]QYCFADPY[Nle]CA |
| BCY8667 | 255 | [Ac]ACIEEGAYCFADPY[Nle]CA |
| BCY8668 | 256 | [Ac]ACIEEG[Aib]YCFADPY[Nle]CA |
| BCY8669 | 257 | [Ac]ACIEEG[AC5C]YCFADPY[Nle]CA |
| BCY8670 | 258 | [Ac]ACIEEGQ[4MePhe]CFADPY[Nle]CA |
| BCY8671 | 259 | [Ac]ACIEEGQ[1Nal]CFADPY[Nle]CA |
| BCY8673 | 260 | [Ac]ACIEEGQYC[2Nal]ADPY[Nle]CA |
| BCY8674 | 261 | [Ac]ACIEEGQYC[NO2Phe]ADPY[Nle]CA |

189

-continued

| Peptide Number | SEQ ID NO: | Sequence |
|---|---|---|
| BCY8675 | 262 | [Ac]ACIEEGQYC[4BrPhe]ADPY[Nle]CA |
| BCY8676 | 263 | [Ac]ACIEEGQYCF[Abu]DPY[Nle]CA |
| BCY8677 | 264 | [Ac]ACEEEGQYCFADPY[Ahp]CA |
| BCY9273 | 265 | [Ac]ACIEEGQYCFADPYMCA | wherein $C_i$, $C_{ii}$ and $C_{iii}$ represent first, second and third cysteine residues, respectively, Ac represents an N-terminal acetyl group and Dap represents diaminopropionic acid or a pharmaceutically acceptable salt thereof.

10. The method of claim 9, wherein the molecular scaffold is 1,1',1''-(1,3,5-triazinane-1,3,5-triyl)triprop-2-en-1-one (TATA).

11. A method of treating a cancer or inflammation by inhibiting CD137 in a patient, wherein the method comprising administering to the patient a peptide ligand specific for CD137 comprising a polypeptide comprising at least three cysteine residues, separated by two loop sequences, and a molecular scaffold which forms covalent bonds with the cysteine residues of the polypeptide such that two polypeptide loops are formed on the molecular scaffold, wherein the peptide ligand comprises an amino acid sequence which is:

$$C_i\text{-}X_5\text{-}X_6\text{-}X_7\text{-}X_8\text{-}X_9\text{-}X_{10}\text{-}C_{ii}\text{-}X_{ii}\text{-}X_{12}\text{-}D\text{-}X_{13}\text{-}X_{14}\text{-}X_{15}\text{-}C_{iii};$$
(SEQ ID NO: 266)

wherein $C_i$, $C_{ii}$ and $C_{iii}$ represent first, second and third cysteine residues, respectively;
$X_5$ represents Ile, tBuAla or Chg;
$X_6$ represents Glu, Pro, Asp, Lys, Aad, HyP or Oxa;
$X_7$ represents Glu, Lys or Aad;
$X_8$ represents Gly, D-Lys, D-Ala, L-Ala, D-Phe, D-Glu, D-Gln, D-Leu, D-Ser or D-Trp;
$X_9$ represents Gln, Lys, Ala, Pro, 5,5-dmP, Oic, Oxa, HyP, Aib or Ac5c;
$X_{10}$ represents Tyr, Phe, 3MePhe, 4MePhe, 4FPhe, 2Nal, 4MeOPhe or 4,4-BPA;
$X_{11}$ represents Phe, Lys, 4MePhe, 2FPhe, 4FPhe, 4Pal, 4,4-BPA, 4tBuPhe, NO2Phe or 4BrPhe;
$X_{12}$ represents Ala or Lys;
$X_{13}$ represents Pro or Lys;
$X_{14}$ represents Tyr or Lys; and
$X_{15}$ represents Met, Lys, Nle, HLeu or Ahp.

12. The method of claim 11, wherein the peptide ligand of SEQ ID NO: 266 is selected from the $C_i$ to $C_{ii}$ sequences of the following peptides or the full sequences of the following peptides:

| Peptide Number | SEQ ID NO: | Sequence |
|---|---|---|
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7244 | 57 | Ac-CIEEGQYCK(Peg12)ADPYMC |
| BCY7245 | 58 | Ac-CIEEGQYCFK(Peg12)DPYMC |
| BCY7247 | 60 | Ac-CIEEGQYCFADK(Peg12)YMC |
| BCY7248 | 61 | Ac-CIEEGQYCFADPK(Peg12)MC |
| BCY7249 | 62 | Ac-CIEEGQYCFADPYK(Peg12)C |
| BCY7416 | 63 | [Ac]CIEE[dK(PEG12FL)]QYCFADPY[Nle]C |
| BCY7287 | 97 | [PEG3]-ACIEEGAYCFADPY(Nle)CA |
| BCY7297 | 106 | [PEG3]-ACIEEaQYCFADPY(Nle)CA |
| BCY7154 | 117 | [PEG3]-AC-Chg-EEGQYCFADPY[Nle]CA |
| BCY7156 | 119 | [PEG3]-ACIPEGQYCFADPY[Nle]CA |
| BCY7157 | 120 | [PEG3]-ACIDEGQYCFADPY[Nle]CA |
| BCY7158 | 121 | [PEG3]-ACI-Aad-EGQYCFADPY[Nle]CA |
| BCY7162 | 125 | [PEG3]-ACIE-Aad-GQYCFADPY[Nle]CA |
| BCY7165 | 128 | [PEG3]-ACIEE-DLys-QYCFADPY[Nle]CA |
| BCY7166 | 129 | [PEG3]-ACIEE-DPhe-QYCFADPY[Nle]CA |
| BCY7167 | 130 | [PEG3]-ACIEE-DGlu-QYCFADPY[Nle]CA |
| BCY7168 | 131 | [PEG3]-ACIEE-DGln-QYCFADPY[Nle]CA |
| BCY7169 | 132 | [PEG3]-ACIEE-DLeu-QYCFADPY[Nle]CA |
| BCY7170 | 133 | [PEG3]-ACIEE-DSer-QYCFADPY[Nle]CA |
| BCY7174 | 136 | [PEG3]-ACIEEGPYCFADPY[Nle]CA |
| BCY7175 | 137 | [PEG3]-ACIEEGQFCFADPY[Nle]CA |
| BCY7177 | 139 | [PEG3]-ACIEEGQ-3MeF-CFADPY[Nle]CA |
| BCY7178 | 140 | [PEG3]-ACIEEGQ-4MeF-CFADPY[Nle]CA |
| BCY7179 | 141 | [PEG3]-ACIEEGQ-4FF-CFADPY[Nle]CA |
| BCY7183 | 145 | [PEG3]-ACIEEGQYC-4MeF-ADPY[Nle]CA |
| BCY7185 | 147 | [PEG3]-ACIEEGQYC-4FF-ADPY[Nle]CA |
| BCY7195 | 156 | [PEG3]AC[tBuAla]EEGQYCFAD |

-continued

| Peptide Number | SEQ ID NO: | Sequence |
|---|---|---|
| | | PY[Nle]CA |
| BCY7198 | 159 | [PEG3]ACIEEGQYC[2FPhe]ADPY[Nle]CA |
| BCY7211 | 170 | [PEG3]ACIEEGQYCFADPY[HLeu]CA |
| BCY7311 | 188 | [PEG3]-ACIEEGQYCFADPY[Ahp]CA |
| BCY7768 | 195 | [PEG3]ACIPE[dF]QYCFADPY[Nle]CA |
| BCY7770 | 196 | [PEG3]ACIPE[dF]PYCFADPY[Nle]CA |
| BCY7772 | 197 | [PEG3]ACIEE[dF]PYCFADPY[Nle]CA |
| BCY7773 | 198 | PEG3]ACIPEGPYCFADPY[Nle]CA |
| BCY7774 | 199 | PEG3]AC[tBuAla]PE[dF]P[4MePhe]C[4FPhe]ADPY[Nle]CA |
| BCY7775 | 200 | [PEG3]AC[tBuAla]PE[dF]Q[4MePhe]C[4FPhe]ADPY[Nle]CA |
| BCY7776 | 201 | [PEG3]AC[tBuAla]EE[dF]P[4MePhe]C[4FPhe]ADPY[Nle]CA |
| BCY7796 | 203 | [PEG3]ACI[HyP]EGQYCFADPY[Nle]CA |
| BCY7798 | 204 | [PEG3]ACIEE[dW]QYCFADPY[Nle]CA |
| BCY7801 | 207 | PEG3]ACIEEGQ[2Nal]CFADPY[Nle]CA |
| BCY7802 | 208 | PEG3]ACIEEGQ[4MeoPhe]CFADPY[Nle]CA |
| BCY7936 | 223 | [Ac]ACIEEGQ[44BPA]CFADPY[Nle]CA |
| BCY7941 | 227 | [Ac]ACIEEGQYC[4Pal]ADPY[Nle]CA |
| BCY7942 | 228 | [Ac]ACIEEGQYC[44BPA]ADPY[Nle]CA |
| BCY7944 | 230 | Ac]ACIEEGQYC[4tBuPhe]ADPY[Nle]CA |
| BCY7950 | 232 | [Ac]ACIEEG[55DMP]YCFADPY[Nle]CA |
| BCY7954 | 234 | [Ac]ACIEEG[Oic]YCFADPY[Nle]CA |
| BCY7958 | 238 | [Ac]ACI[Oxa]EGQYCFADPY[Nle]CA |
| BCY7959 | 239 | [Ac]ACIEEG[Oxa]YCFADPY[Nle]CA |
| BCY7960 | 240 | [Ac]ACIPEGPYCFADPY[Nle]CA |
| BCY7952 | 241 | [Ac]ACIEEG[HyP]YCFADPY[Nle]CA |
| BCY7961 | 242 | [Ac]ACIPE[dA]PYCFADPY[Nle]CA |
| BCY8656 | 245 | [Ac]AC[tBuAla]EEGQYCFADPY[Nle]CA |
| BCY8659 | 248 | [Ac]ACIPEGQYCFADPY[Nle]CA |
| BCY8663 | 252 | [Ac]ACIEE[dF]QYCFADPY[Nle]CA |
| BCY8668 | 256 | [Ac]ACIEEG[Aib]YCFADPY[Nle]CA |
| BCY8669 | 257 | [Ac]ACIEEG[AC5C]YCFADPY[Nle]CA |
| BCY8674 | 261 | [Ac]ACIEEGQYC[NO2Phe]ADPY[Nle]CA |
| BCY8675 | 262 | [Ac]ACIEEGQYC[4BrPhe]ADPY[Nle]CA |
| BCY9273 | 265 | [Ac]ACIEEGQYCFADPYIVICA |
| BCY3814 | 31 | ACIEEGQYCFADPY(Nle)CA |
| BCY7527 | 194 | [Ac]CIEEGQYCFADPY[Nle]C[Dap] |
| BCY7965 | 243 | [Ac]AC[tBuAla]PE[dA]PYCFADPY[Nle]CA |

13. The method of claim 11, wherein the peptide ligand comprises three cysteine residues separated by two loop sequences both of which consist of 6 amino acids, and said peptide ligand comprises an amino acid sequence:

$$C_i\text{-}X_5\text{-}X_6\text{-}X_7\text{-}X_8\text{-}X_9\text{-}X_{10}\text{-}C_{ii}\text{-}X_{11}\text{-}A\text{-}D\text{-}P\text{-}Y\text{-}X_{15}\text{-}C_{iii}; \quad (\text{SEQ ID NO: 267})$$

wherein $C_i$, $C_{ii}$ and $C_{iii}$ represent first, second and third cysteine residues, respectively;
$X_5$ represents Ile or tBuAla;
$X_6$ represents Lys, Glu or Pro;
$X_7$ represents Glu or D-Lys;
$X_8$ represents Gly, D-Lys, D-Phe or D-Ala;
$X_9$ represents Gln, Lys or Pro;
$X_{10}$ represents Tyr or 4MePhe;
$X_{11}$ represents Phe or 4FPhe; and
$X_{15}$ represents Met or Nle.

14. The method of claim 13, wherein the peptide ligand of SEQ ID NO: 267 is selected from the $C_i$ to $C_{iii}$ sequences of the following peptides or the full sequences of the following peptides:

| Peptide Number | SEQ ID NO: | Sequence |
|---|---|---|
| BCY7239 | 52 | Ac-CIK(Peg12)EGQYCFADPYMC |
| BCY7240 | 53 | Ac-CIEK(Peg12)GQYCFADPYMC |
| BCY7242 | 55 | Ac-CIEEGK(Peg12)YCFADPYMC |
| BCY7416 | 63 | [Ac]CIEE[dK(PEG12FL)]QYCFADPY[Nle]C |
| BCY7156 | 119 | [PEG3]-ACIPEGQYCFADPY[Nle]CA |

-continued

| Peptide Number | SEQ ID NO: | Sequence |
|---|---|---|
| BCY7166 | 129 | [PEG3]-ACIEE-DPhe-QYCFADPY[Nle]CA |
| BCY7174 | 136 | [PEG3]-ACIEEGPYCFADPY[Nle]CA |
| BCY7774 | 199 | PEG3]AC[tBuAla]PE[dF]P[4MePhe]C[4FPhe]ADPY[Nle]CA |
| BCY9273 | 265 | [Ac]ACIEEGQYCFADPYMCA |
| BCY3814 | 31 | ACIEEGQYCFADPY(Nle)CA |
| BCY7527 | 194 | [Ac]CIEEGQYCFADPY[Nle]C[Dap] |
| BCY7965 | 243 | [Ac]AC[tBuAla]PE[dA]PYCFADPY[Nle]CA. |

15. The method of claim 11, wherein the molecular scaffold is 1,1',1"-(1,3,5-triazinane-1,3,5-triyl)triprop-2-en-1-one (TATA).

16. The method of claim 1, wherein the peptide ligand comprises one or more effector and/or functional groups.

17. The method of claim 1, wherein the peptide ligand comprises one or more cytotoxic agents.

18. The method of claim 9, wherein the peptide ligand comprises one or more effector and/or functional groups.

19. The method of claim 9, wherein the peptide ligand comprises one or more cytotoxic agents.

20. The method of claim 11, wherein the peptide ligand comprises one or more effector and/or functional groups.

21. The method of claim 11, wherein the peptide ligand comprises one or more cytotoxic agents.

22. The method of claim 1, wherein the cancer is selected from adenocarcinoma and squamous cell carcinoma, colorectal carcinoma, Hodgkin's Lymphoma (HL), B chronic lymphocytic leukemia, B acute lymphocytic leukemia (ALL), and T acute lymphocytic leukemia (ALL).

23. The method of claim 9, wherein the cancer is selected from adenocarcinoma and squamous cell carcinoma, colorectal carcinoma, Hodgkin's Lymphoma (HL), B chronic lymphocytic leukemia, B acute lymphocytic leukemia (ALL), and T acute lymphocytic leukemia (ALL).

24. The method of claim 11, wherein the cancer is selected from adenocarcinoma and squamous cell carcinoma, colorectal carcinoma, Hodgkin's Lymphoma (HL), B chronic lymphocytic leukemia, B acute lymphocytic leukemia (ALL), and T acute lymphocytic leukemia (ALL).

* * * * *